United States Patent
Tsuyuki

(10) Patent No.: US 11,172,904 B2
(45) Date of Patent: Nov. 16, 2021

(54) X-RAY CT APPARATUS AND IMAGING PLANNING APPARATUS

(71) Applicant: CANON MEDICAL SYSTEMS CORPORATION, Otawara (JP)

(72) Inventor: Masaharu Tsuyuki, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 10 days.

(21) Appl. No.: 16/599,634

(22) Filed: Oct. 11, 2019

(65) Prior Publication Data

US 2020/0129137 A1    Apr. 30, 2020

(30) Foreign Application Priority Data

Oct. 12, 2018 (JP) .............................. JP2018-193805
Oct. 12, 2018 (JP) .............................. JP2018-193806
Oct. 11, 2019 (JP) .............................. JP2019-187551

(51) Int. Cl.
*A61B 6/00* (2006.01)
*G01T 1/17* (2006.01)
*A61B 6/03* (2006.01)

(52) U.S. Cl.
CPC .............. *A61B 6/542* (2013.01); *A61B 6/032* (2013.01); *A61B 6/482* (2013.01); *G01T 1/17* (2013.01)

(58) Field of Classification Search
CPC ......... A61B 6/542; A61B 6/482; A61B 6/032; A61B 6/488; A61B 6/4035; A61B 6/405;

(Continued)

(56) References Cited

U.S. PATENT DOCUMENTS 8,699,657 B2 * 4/2014 Baeumer .............. A61B 6/4035
378/9
2009/0097611 A1 4/2009 Nishide et al.
(Continued)

FOREIGN PATENT DOCUMENTS

JP    2008-279153 A    11/2008
JP    2009-95405 A    5/2009
(Continued)

*Primary Examiner* — Marcus H Taningco
(74) *Attorney, Agent, or Firm* — Oblon, McClelland, Maier & Neustadt, L.L.P.

(57) ABSTRACT

An X-ray CT apparatus according to an embodiment includes: an X-ray generator configured to generate X-rays; an X-ray detector configured to detect X-rays that have passed through a patient and including first to n-th groups of detecting elements configured to store therein electric charges generated from the detection (where n is an integer of 2 or larger); a Data Acquisition System (DAS) configured to acquire detection data for each view, by repeatedly performing a process of sequentially reading the electric charges stored in the first to the n-th groups of detecting elements in units of groups, starting with the first group of detecting elements; and processing circuitry configured to periodically change energy of X-rays radiated onto the patient and to also control the X-ray generator so that, while the detection data related to one view or a plurality of consecutive views is acquired, an average energy level of the X-rays radiated onto the patient is substantially equal among the groups of detecting elements.

30 Claims, 29 Drawing Sheets

(58) Field of Classification Search
CPC ..... A61B 6/027; A61B 6/0487; A61B 6/4291; G01T 1/17; H04N 5/32
See application file for complete search history.

(56) References Cited

U.S. PATENT DOCUMENTS

| | | | |
|---|---|---|---|
| 2010/0014628 | A1 | 1/2010 | Kadomura et al. |
| 2010/0303196 | A1* | 12/2010 | Zou .................. A61B 6/542 378/5 |
| 2011/0176745 | A1* | 7/2011 | Zamyatin .............. G06T 11/005 382/274 |
| 2013/0053689 | A1* | 2/2013 | Das ..................... A61B 6/5235 600/425 |
| 2014/0321603 | A1 | 10/2014 | Taguchi et al. |
| 2016/0007943 | A1* | 1/2016 | Hoernig ................ A61B 6/482 378/37 |
| 2016/0242704 | A1* | 8/2016 | Yamazaki ............ G01T 1/2018 |
| 2018/0296170 | A1 | 10/2018 | Shirono |

FOREIGN PATENT DOCUMENTS

| | | |
|---|---|---|
| JP | 2012-200555 A | 10/2012 |
| JP | 2014-45896 A | 3/2014 |
| JP | 2014-61286 A | 4/2014 |
| JP | 2017-119002 A | 7/2017 |
| WO | WO 2008/075595 A1 | 6/2008 |

* cited by examiner

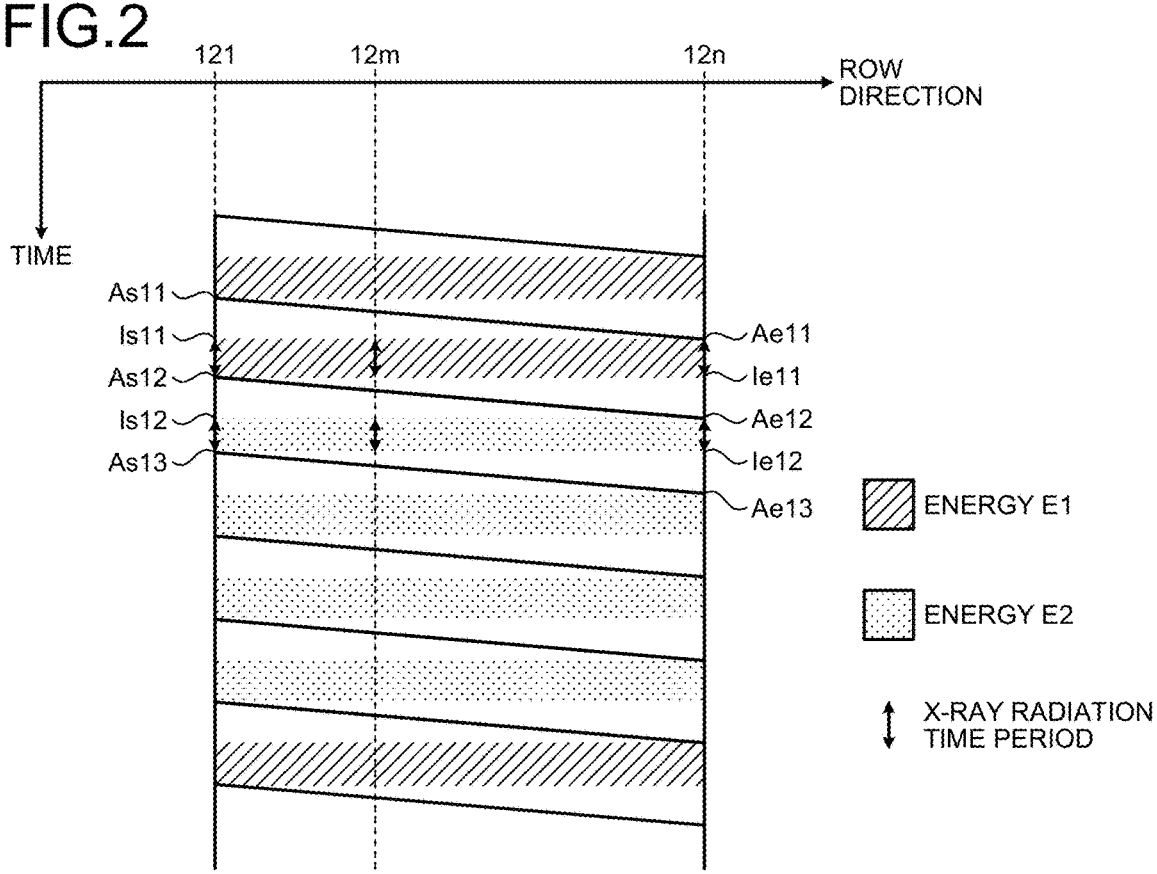
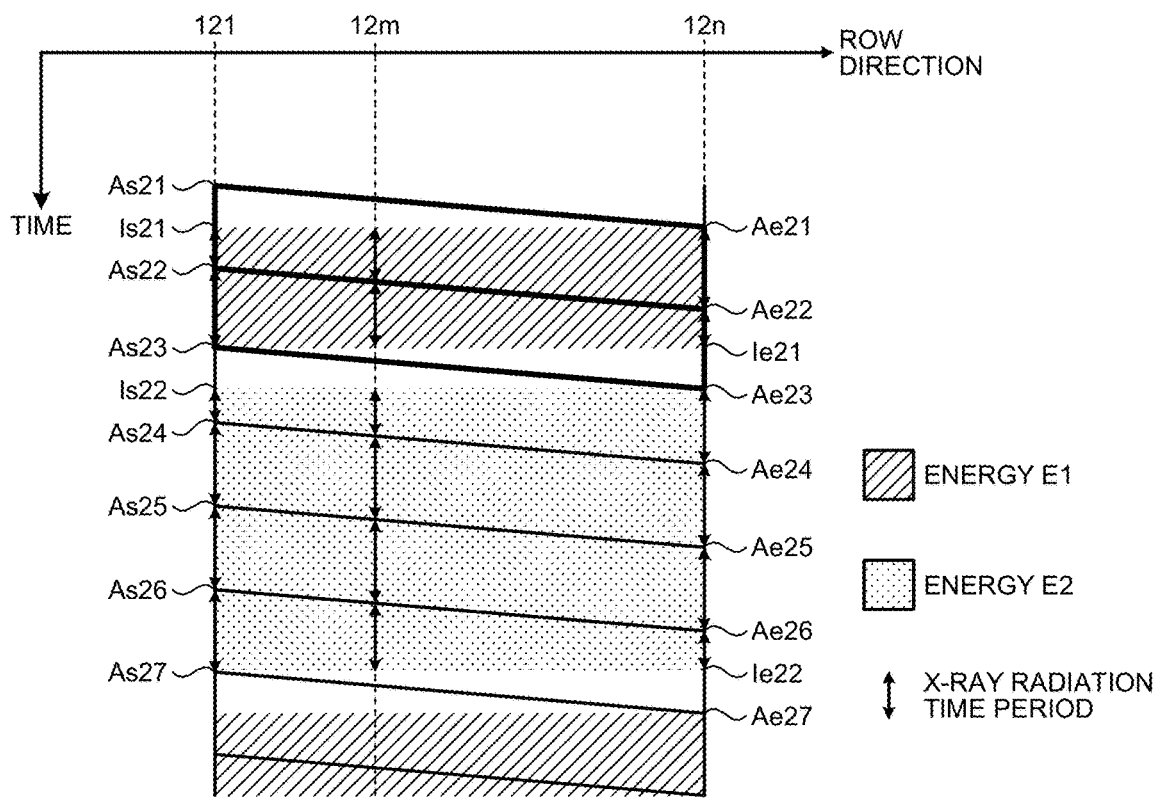

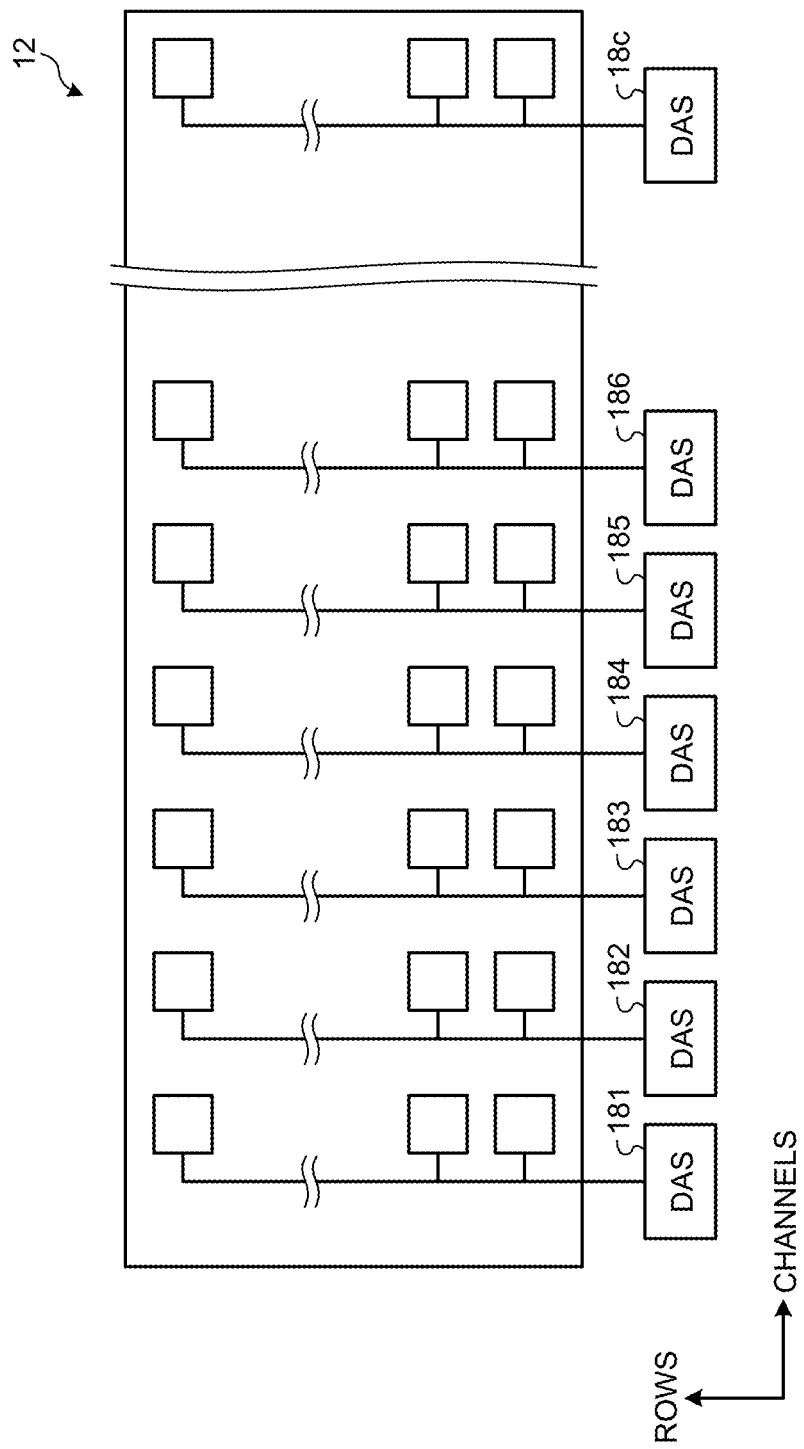

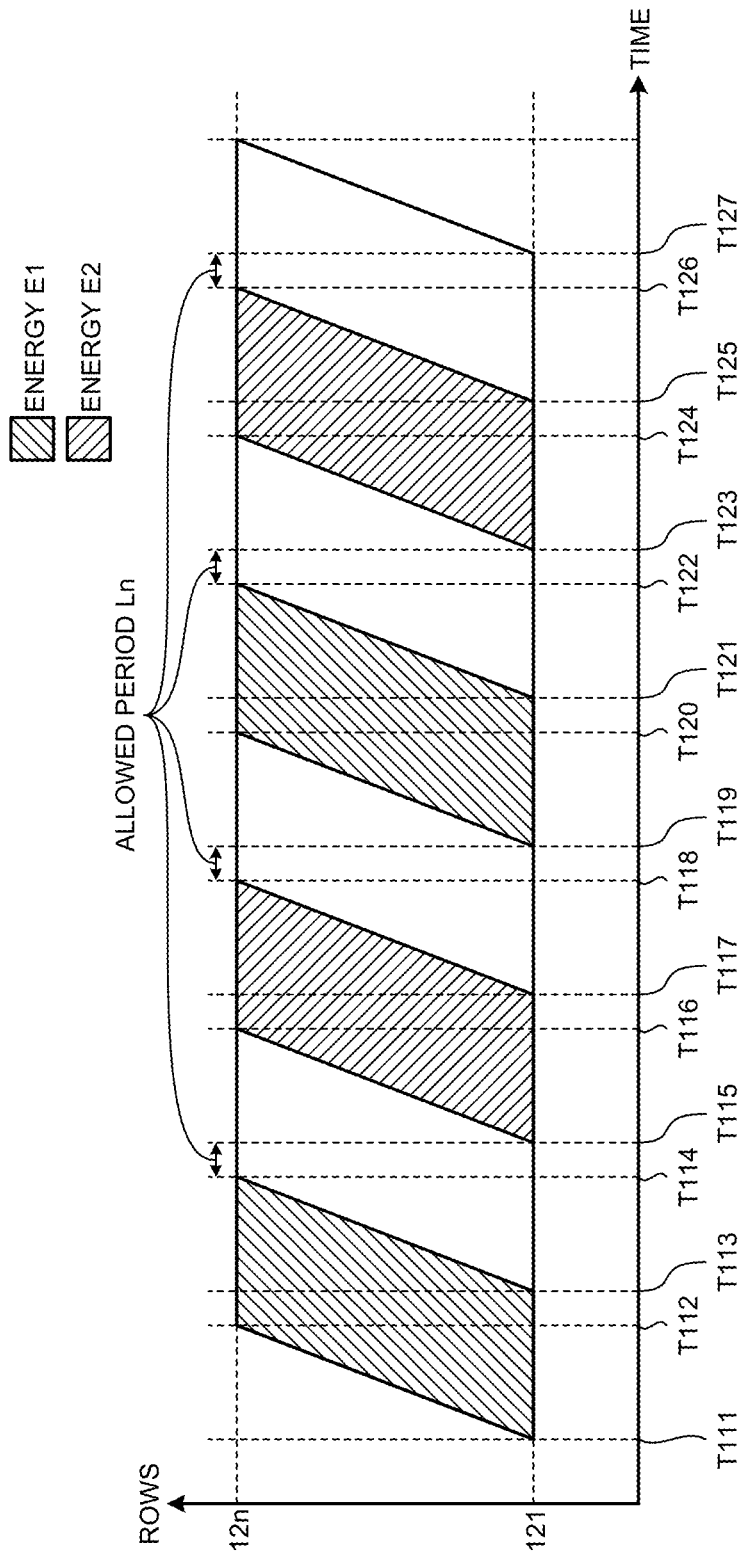

FIG.23

|  | | TUBE CURRENT VALUES | | |
| --- | --- | --- | --- | --- |
|  | | 700 mA | 500 mA | 300 mA |
| kV DIF-FERENCE | 60 kV | n | n/2 | n/4 |
|  | 80 kV | n/2 | n/2 | n/4 |
|  | 100 kV | n/2 | n/4 | n/4 |

| IMAGING RANGE [mm] | 500 | | |
|---|---|---|---|
| PREDETERMINED IMAGING TIME [s] | 10 | | |
| NUMBERS OF ROWS | n | n/2 | n/4 |
| IMAGING TIMES CORRESPONDING TO NUMBERS OF ROWS [s] | 6.25 | 12.5 | 25 |

FIG.27

|  | A | B | C |
|---|---|---|---|
| IMAGING RANGE [mm] | 500 | 300 | 200 |
| PREDETERMINED IMAGING TIME [s] | 10 | | |
| NUMBERS OF ROWS | n | n/2 | n/4 |
| IMAGING TIMES CORRESPONDING TO NUMBERS OF ROWS [s] | 6.25 | 7.5 | 10 |

FIG.29

| IMAGING RANGE [mm] | 500 ||
|---|---|---|
| PREDETERMINED IMAGING TIME [s] | 10 ||
| TUBE CURRENT VALUE [mA] | 500 ||
| FIRST TUBE VOLTAGE VALUE [kV] | 140 ||
| SECOND TUBE VOLTAGE VALUE [kV] | 80 ||
| SELECTABLE NUMBERS OF ROWS | n | n/2 |
| IMAGING TIMES CORRESPONDING TO NUMBERS OF ROWS [s] | 6.25 | 12.5 |

X-RAY CT APPARATUS AND IMAGING PLANNING APPARATUS

CROSS-REFERENCE TO RELATED APPLICATIONS

This application is based upon and claims the benefit of priority from Japanese Patent Application No. 2018-193805, filed on Oct. 12, 2018; Japanese Patent Application No. 2018-193806, filed on Oct. 12, 2018 and Japanese Patent Application No. 2019-187551, filed on Oct. 11, 2019, the entire contents of all of which are incorporated herein by reference.

FIELD

Embodiments described herein relate generally to an X-ray Computed Tomography (CT) apparatus and an imaging planning apparatus.

BACKGROUND

In recent years, as the precision levels of X-ray detectors are getting higher, Data Acquisition Systems (DASs) based on a sequential acquisition method have popularly been used in Computed Tomography (CT) scans. A DAS using a sequential acquisition method is configured to sequentially acquire signals of X-rays detected by a plurality of detecting elements, while shifting the timing for each detecting element. For example, the DAS using the sequential acquisition method has an Analog/Digital (A/D) converter shared among a plurality of elements, so as to sequentially perform an A/D conversion. As a result, because the single DAS is able to acquire the signals from the plurality of detecting elements, it is possible to keep small the number of DASs in relation to the number of detecting elements.

Further, for CT scans, a technique is known by which a Dual-Energy (DE) acquisition is performed by using X-rays having two mutually-different types of energy. Also, for CT scans, another technique is known by which a Multi-Energy (ME) acquisition is performed by using X-rays having three or more mutually-different types of energy. By using these techniques, it is possible to acquire projection data corresponding to the different types of energy, so as to discriminate the types, the atomic numbers, the density levels, and the like of substances included in an examined subject, on the basis of the notion that different substances have different X-ray absorption characteristics. The DE acquisition and the ME acquisition are each performed by using a fast switching method by which the energy of the X-rays is changed in correspondence with, for example, radiation angles of the X-rays with respect to the examined subject. According to the fast switching method, for example, the energy of the X-rays is changed for every one or more views. When the DE acquisition or the ME acquisition is performed by using the fast switching method, one or more DASs using a simultaneous acquisition method are usually employed. A DAS using the simultaneous acquisition method is provided for each of the detecting elements and is configured to read an electric charge at the same time as the electric charge is stored in a corresponding one of the detecting elements.

BRIEF DESCRIPTION OF THE DRAWINGS

FIG. 2 is a chart for explaining control over energy of X-rays according to the first embodiment;

FIG. 3 is another chart for explaining the control over the energy of the X-rays according to the first embodiment;

FIG. 13B is a diagram illustrating examples of DASs according to the fifth embodiment;

FIG. 14 is a chart illustrating an example of a dual-energy acquisition employing a DAS that uses a sequential acquisition method according to the fifth embodiment;

FIG. 23 is a table for explaining an example of control over an allowed time period according to a sixth embodiment;

FIG. 27 is a table for explaining another example of the control over the allowed time period according to the seventh embodiment;

FIG. 29 is a table for explaining an example of control over an allowed time period according to an eighth embodiment;

DETAILED DESCRIPTION

An X-ray CT apparatus comprises an X-ray generator, an X-ray detector, a Data Acquisition System (DAS), and processing circuitry. The X-ray generator is configured to generate X-rays. The X-ray detector is configured to detect X-rays that have passed through a patient and including first to n-th groups of detecting elements configured to store therein electric charges generated from the detection (where n is an integer of 2 or larger). The DAS is configured to acquire detection data for each view, by repeatedly performing a process of sequentially reading the electric charges stored in the first to the n-th groups of detecting elements in units of groups, starting with the first group of detecting elements. The processing circuitry is configured to periodically change energy of X-rays radiated onto the patient and to also control the X-ray generator so that, while the detection data related to one view or a plurality of consecutive views is acquired, an average energy level of the X-rays radiated onto the patient is substantially equal among the groups of detecting elements.

Exemplary embodiments of the X-ray CT apparatus and an imaging planning apparatus will be explained in detail below, with reference to the accompanying drawings.

Figure 1:
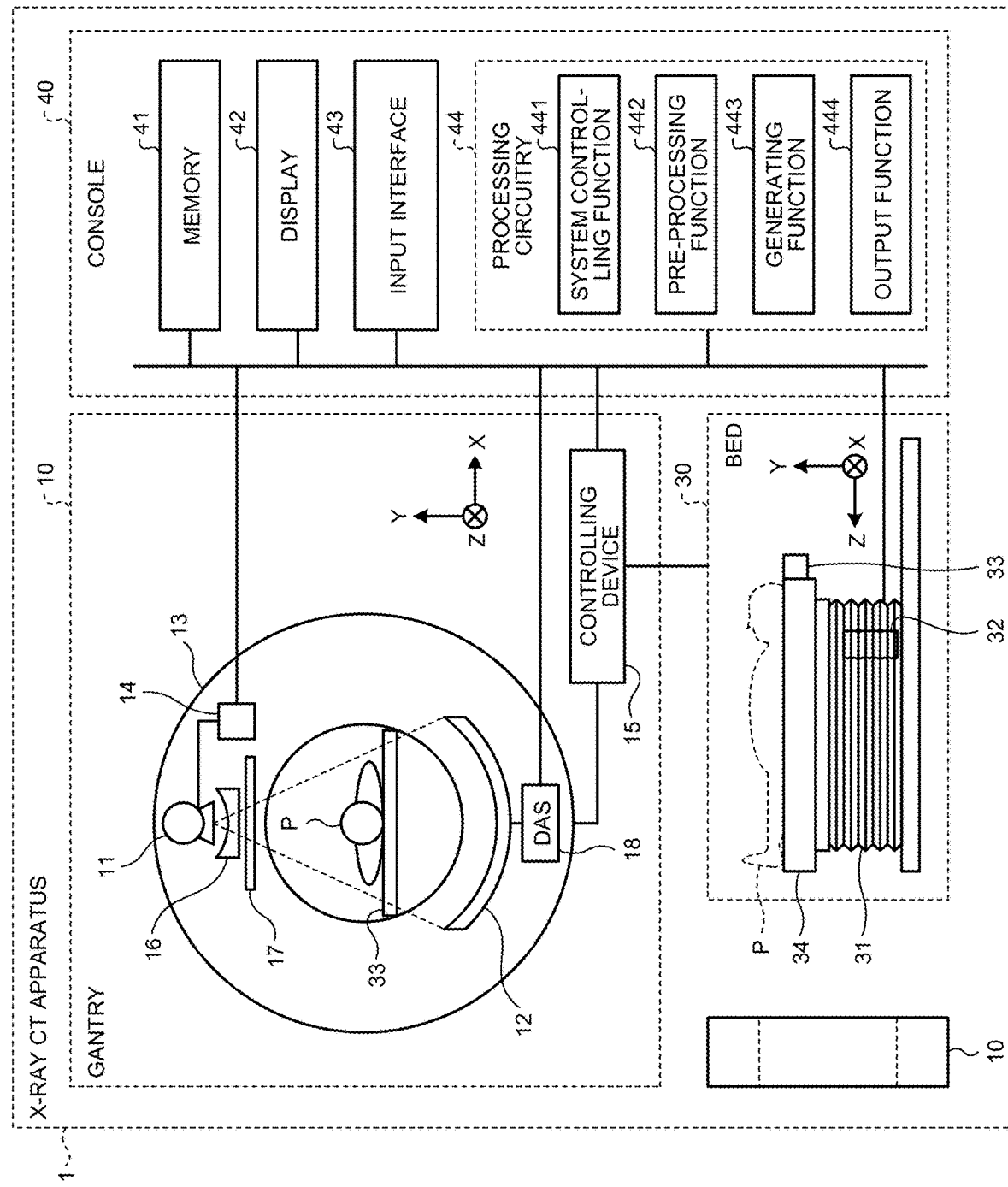
FIG. 1 is a block diagram illustrating an exemplary configuration of an X-ray CT apparatus 1 according to the first embodiment.

A configuration of an X-ray CT apparatus 1 according to a first embodiment will be explained with reference to FIG. 1. FIG. 1 is a block diagram illustrating the exemplary configuration of the X-ray CT apparatus 1 according to the first embodiment. As illustrated in FIG. 1, the X-ray CT apparatus 1 includes a gantry 10, a bed 30, and a console 40.

In FIG. 1, the rotation axis of a rotating frame 13 in a non-tilted state or the longitudinal direction of a tabletop 33 of the bed 30 corresponds to a Z-axis direction. Further, the axial direction orthogonal to the Z-axis direction and parallel to the floor surface corresponds to an X-axis direction. The axial direction orthogonal to the Z-axis direction and perpendicular to the floor surface corresponds to a Y-axis direction. In FIG. 1, the gantry 10 is drawn as viewed from multiple directions for the sake of convenience in the explanation. FIG. 1 illustrates the example in which the X-ray CT apparatus 1 includes the one gantry 10.

The gantry 10 includes an X-ray tube 11, an X-ray detector 12, the rotating frame 13, an X-ray high-voltage device 14, a controlling device 15, a wedge 16, a collimator 17, and one or more DASs 18.

The X-ray tube 11 is a vacuum tube including a negative pole (a filament) configured to generate thermo electrons and a positive pole (a target) configured to generate X-rays in response to collisions of the thermo electrons. With high voltage being applied thereto from the X-ray high-voltage device 14, the X-ray tube 11 is configured to generate the X-rays to be radiated onto an examined subject (hereinafter, "patient") P, by radiating the thermo electrons from the negative pole toward the positive pole. For example, the X-ray tube 11 may be an X-ray tube of a rotating anode (positive pole) type configured to generate X-rays by radiating thermo electrons on a rotating anode. The X-ray tube 11 is an example of the X-ray generator.

The X-ray detector 12 is configured to detect X-rays that were radiated from the X-ray tube 11 and have passed through the patient P and to output a signal corresponding to the detected X-ray amount to the one or more DASs 18. The X-ray detector 12 includes, for example, a plurality of rows of detecting elements in each of which a plurality of detecting elements are arranged in a channel direction along an arc centered on a focal point of the X-ray tube 11. For example, the X-ray detector 12 has a structure in which the plurality of rows in each of which the plurality of detecting elements are arranged in the channel direction are arranged in the row direction (a slice direction). Further, the X-ray detector 12 is, for example, a detector of an indirect conversion type including a grid, a scintillator array, and an optical sensor array. The scintillator array includes a plurality of scintillators. Each of the scintillators includes a scintillator crystal that outputs light having a photon quantity corresponding to the amount of X-rays that have become incident thereto. The grid is disposed on the surface of the scintillator array positioned on the X-ray incident side and includes an X-ray blocking plate that absorbs scattered X-rays. The grid may be referred to as a collimator (a one-dimensional collimator or a two-dimensional collimator). The optical sensor array has a function of converting outputs from the scintillators into electric signals corresponding to the amounts of light and may include, for example, optical sensors such as photodiodes.

Alternatively, the X-ray detector 12 may be a detector of a direct conversion type including semiconductor elements configured to convert incident X-rays into electric signals. Further, the X-ray detector 12 is an example of the X-ray detector.

The rotating frame 13 is an annular frame configured to support the X-ray tube 11 and the X-ray detector 12 so as to oppose each other and to rotate the X-ray tube 11 and the X-ray detector 12 via the controlling device 15. For example, the rotating frame 13 is cast by using aluminum. In addition to supporting the X-ray tube 11 and the X-ray detector 12, the rotating frame 13 is also capable of further supporting the X-ray high-voltage device 14, the wedge 16, the collimator 17, the one or more DASs 18, and the like. Also, the rotating frame 13 is capable of further supporting various types of structures that are not illustrated in FIG. 1. In the gantry 10, the rotating frame 13 and the part that rotates and moves together with the rotating frame 13 may hereinafter be referred to as a rotating part.

The X-ray high-voltage device 14 includes: a high-voltage generating device including electric circuitry such as a transformer, a rectifier, and the like and configured to generate the high voltage to be applied to the X-ray tube 11;

and an X-ray controlling device configured to control the output voltage in accordance with the X-rays to be generated by the X-ray tube 11. The high-voltage generating device may be of a transformer type or of an inverter type. Further, the X-ray high-voltage device 14 may be provided for the rotating frame 13 or for a fixed frame (not illustrated).

The controlling device 15 includes: processing circuitry having a Central Processing Unit (CPU) or the like; and a driving mechanism configured with a motor, an actuator, and the like. The controlling device 15 is configured to receive an input signal from an input interface 43 and to control operations of the gantry 10 and the bed 30. For example, the controlling device 15 exercises control over the rotating of the rotating frame 13, the tilting of the gantry 10, operations of the bed 30 and the tabletop 33, and the like. In one example, as the control over the tilting of the gantry 10, the controlling device 15 rotates the rotating frame 13 being centered on an axis extending parallel to the X-axis direction by using tilting angle (tilt angle) information input thereto. The controlling device 15 may be provided for the gantry 10 or for the console 40.

The wedge 16 is a filter used for adjusting the amount of X-rays radiated from the X-ray tube 11. More specifically, the wedge 16 is a filter configured to pass and attenuate the X-rays radiated from the X-ray tube 11, so that the X-rays radiated from the X-ray tube 11 onto the patient P have a predetermined distribution. For example, the wedge 16 may be a wedge filter or a bow-tie filter and is a filter obtained by processing aluminum or the like so as to have a predetermined target angle and a predetermined thickness.

The collimator 17 is structured with lead plates or the like used for narrowing down the radiation range of the X-rays that have passed through the wedge 16 and is configured to form a slit with a combination of the plurality of lead plates or the like. The collimator 17 may be referred to as an X-ray limiter. Further, although FIG. 1 illustrates the example in which the wedge 16 is arranged between the X-ray tube 11 and the collimator 17, the collimator 17 may be arranged between the X-ray tube 11 and the wedge 16. In that situation, the wedge 16 is configured to pass and attenuate the X-rays which were radiated from the X-ray tube 11 and of which the radiation range has been limited by the collimator 17.

The DAS 18 is configured to acquire the signals of the X-rays detected by the detecting elements included in the X-ray detector 12. For example, the DAS 18 includes an amplifier configured to perform an amplifying process on the electric signals output from the detecting elements; and an A/D converter configured to convert the electric signals into digital signals. The DAS 18 is configured to generate detection data. The DAS 18 may be realized by using a processor, for example. The DAS 18 is an example of an acquiring unit.

In the present example, the DAS 18 is configured to sequentially acquire the signals of the X-rays detected by the plurality of detecting elements, for each view. For example, the DAS 18 is connected to a plurality of detecting elements via a switch and is configured to sequentially read electric charges integrated by the detecting elements, while switching from one detecting element to another to turn on the connection therewith.

Next, an example of the sequential acquisition performed by the DAS 18 will be explained. For the sake of convenience in the explanation, a sequential acquisition using four detecting elements will be explained; however, the number of detecting elements to be connected to the DAS 18 is not limited to that in this example. In one example, the DAS 18 is connected, via the switch, to four detecting elements, namely, a detecting element 12a, a detecting element 12b, a detecting element 12c, and a detecting element 12d. In that situation, at first, the DAS 18 turns on the connection to the detecting element 12a and reads an electric charge integrated by the detecting element 12a as an X-ray signal S11.

Subsequently, the DAS 18 turns off the connection to the detecting element 12a and turns on the connection to the detecting element 12b so as to read an electric charge integrated by the detecting element 12b as an X-ray signal S12. As the connection thereof to the DAS 18 is turned off, the detecting element 12a starts integrating an electric charge.

After that, the DAS 18 turns off the connection to the detecting element 12b and turns on the connection to the detecting element 12c so as to read an electric charge integrated by the detecting element 12c as an X-ray signal S13. As the connection thereof to the DAS 18 is turned off, the detecting element 12b starts integrating an electric charge.

After that, the DAS 18 turns off the connection to the detecting element 12c and turns on the connection to the detecting element 12d so as to read an electric charge integrated by the detecting element 12d as an X-ray signal S14. As the connection thereof to the DAS 18 is turned off, the detecting element 12c starts integrating an electric charge. Further, after reading the signal S14, the DAS 18 turns off the connection to the detecting element 12d. As a result, the detecting element 12d starts integrating an electric charge.

In this manner, from the four detecting elements, namely, the detecting element 12a, the detecting element 12b, the detecting element 12c, and the detecting element 12d, the DAS 18 sequentially acquires the four signals (the signals S11, S12, S13, and S14) with respect to one view. Similarly, the DAS 18 sequentially acquires four signals from the four detecting elements with respect to the following view. In other words, the DAS 18 is configured to sequentially acquire four signals of the X-rays detected by the four detecting elements, for each view.

The example with the detecting elements 12a, 12b, 12c, and 12d is explained above; however, the quantity of the plurality of detecting elements corresponding to the DAS 18 is not limited to "4". For example, the DAS 18 may be configured to sequentially acquire the signals of the X-rays detected by all of the detecting elements included in the X-ray detector 12, for each view. In that situation, for example, the X-ray CT apparatus 1 includes one DAS 18.

Alternatively, for example, the DAS 18 may be configured to sequentially acquire, for each view, the signals of the X-rays detected by the plurality of detecting elements (a row of detecting elements) arranged along the channel direction in the X-ray detector 12. Alternatively, the DAS 18 may be configured to sequentially acquire, for each view, the signals of the X-rays detected by the plurality of detecting elements (rows of detecting elements) arranged along the row direction in the X-ray detector 12. In this situation, for example, the X-ray CT apparatus 1 includes DASs 18 of which the quantity is equal to the quantity of rows of detecting elements included in the X-ray detector 12.

In the following sections, in the X-ray detector 12, the plurality of detecting elements corresponding to one DAS 18 may be referred to as a family of detecting elements. In other words, the X-ray detector 12 includes one or more families of detecting elements. Further, the X-ray CT apparatus 1 includes one or more DASs 18 each configured to sequentially acquire, for each view, the signals of the X-rays detected by a family of detecting elements.

The data generated by the DAS 18 is transmitted, via optical communication, from a transmitter provided for the rotating frame 13 and including a Light Emitting Diode (LED) to a receiver provided in a non-rotating part (e.g., a fixed frame, which is not illustrated in FIG. 1) of the gantry 10 and including a photodiode and is further transferred to the console 40. In this situation, the non-rotating part may be, for example, the fixed frame or the like configured to rotatably support the rotating frame 13. The method for transmitting the data from the rotating frame 13 to the non-rotating part of the gantry 10 does not necessarily have to be optical communication and may be any contactless data transfer method or any contact-type data transfer method.

The bed 30 is a device configured to have the patient P who is to be scanned placed thereon and to move the patient P. The bed 30 includes a base 31, a bed driving device 32, the tabletop 33, and a supporting frame 34. The base 31 is a casing configured to support the supporting frame 34 so as to be movable in the vertical direction. The bed driving device 32 is a driving mechanism configured to move the tabletop 33 on which the patient P is placed, along the longitudinal direction of the tabletop 33 and includes a motor, an actuator, and the like. The tabletop 33 provided on the top face of the supporting frame 34 is a board on which the patient P is placed. In addition to moving the tabletop 33, the bed driving device 32 may also be configured to move the supporting frame 34 along the longitudinal direction of the tabletop 33.

The console 40 includes a memory 41, a display 42, an input interface 43, and processing circuitry 44. Although the console 40 is described as being separate from the gantry 10, the gantry 10 may include either the console 40 or one or more constituent elements of the console 40.

The memory 41 is realized by using, for example, a semiconductor memory element such as a Random Access Memory (RAM) or a flash memory, or a hard disk, an optical disk, or the like. For example, the memory 41 is configured to store therein projection data and reconstructed image data. Further, for example, the memory 41 is configured to store therein a computer program (hereinafter, "program") that enables the circuits included in the X-ray CT apparatus 1 to realize the functions thereof. Alternatively, the memory 41 may be realized with a group of servers (a cloud) connected to the X-ray CT apparatus 1 via a network.

The display 42 is configured to display various types of information. For example, the display 42 is configured to display image data generated by the processing circuitry 44 and to display a Graphical User Interface (GUI) or the like used for receiving various types of operations from an operator. For example, the display 42 may be a liquid crystal display monitor or a Cathode Ray Tube (CRT) display monitor. The display 42 may be of a desktop type or may be configured with a tablet terminal or the like capable of wirelessly communicating with the main body of the console 40.

The input interface 43 is configured to receive various types of input operations from the operator, to convert the received input operations into electric signals, and to output the electric signals to the processing circuitry 44. For example, the input interface 43 receives, from the operator, an acquisition condition used when the projection data is acquired, a reconstruction condition used when CT image data is reconstructed, an image processing condition used when a post-processing image is generated from the CT image data, and the like. For example, the input interface 43 is realized by using a mouse, a keyboard, a trackball, a switch, a button, a joystick, a touchpad on which an input operation can be performed by touching the operation surface thereof, a touch screen in which a display screen and a touchpad are integrally formed, a contactless input circuit using an optical sensor, an audio input circuit, and/or the like. The input interface 43 may be provided for the gantry 10. Alternatively, the input interface 43 may be configured by using a tablet terminal or the like capable of wirelessly communicating with the main body of the console 40. Further, the input interface 43 does not necessarily have to include one or more physical operation component parts such as a mouse and a keyboard. For instance, possible examples of the input interface 43 include electric signal processing circuitry configured to receive an electric signal corresponding to an input operation from an external input device provided separately from the console 40 and to output the electric signal to the processing circuitry 44.

The processing circuitry 44 is configured to control operations of the entirety of the X-ray CT apparatus 1. The processing circuitry 44 does not necessarily have to be included in the console 40. For example, the processing circuitry 44 may be included in a consolidated server configured to collectively perform processes on detection data obtained by a plurality of medical image diagnosis apparatuses.

For example, the processing circuitry 44 is configured to execute a system controlling function 441, a pre-processing function 442, a generating function 443, and an output function 444. The system controlling function 441 is an example of a controlling unit. For example, by reading and executing a program corresponding to the system controlling function 441 from the memory 41, the processing circuitry 44 controls various types of functions of the processing circuitry 44 on the basis of input operations received from the operator via the input interface 43.

Further, the system controlling function 441 is configured to execute a position determining imaging process by controlling the X-ray CT apparatus 1. For example, the system controlling function 441 executes the position determining imaging process by causing X-rays to be radiated onto the patient P from the X-ray tube 11, by moving the tabletop 33 along the Z-direction while the position of the X-ray tube 11 is fixed at a predetermined rotation angle. Further, by reading and executing a program corresponding to the generating function 443 from the memory 41, the processing circuitry 44 is configured to generate position determining image data on the basis of signals of the X-rays acquired in the position determining imaging process. The position determining image data may be referred to as scanogram image data or scout image data.

Further, the system controlling function 441 is configured to execute a main scan by controlling the X-ray CT apparatus 1. For example, on the basis of the position determining image data, the system controlling function 441 sets scan conditions (e.g., a scan range and an X-ray tube current) of the main scan. Subsequently, by controlling the bed driving device 32, the system controlling function 441 moves the patient P to the inside of an opening of the gantry 10. Further, the system controlling function 441 is configured to adjust the opening degree and the position of the collimator 17. Further, the system controlling function 441 is configured to rotate the rotating part by controlling the controlling device 15.

Further, the system controlling function 441 is configured to arrange the high voltage to be supplied to the X-ray tube 11, by controlling the X-ray high-voltage device 14. Accordingly, the X-ray tube 11 generates the X-rays to be radiated onto the patient P. In this situation, the system controlling function 441 performs either a dual-energy acquisition or a multi-energy acquisition. In other words, the system controlling function 441 changes the energy of the X-rays generated by the X-ray tube 11 for every one or more views. For example, by controlling the X-ray tube voltage (hereinafter, simply "tube voltage") to be supplied to the X-ray tube 11, the system controlling function 441 changes the energy of the X-rays generated by the X-ray tube 11. The control over the energy of the X-rays exercised by the system controlling function 441 will be explained later.

While the main scan is performed by the system controlling function 441, the DAS 18 generates the detection data by sequentially acquiring, for each view, the signals of the X-rays detected by the plurality of detecting elements. Further, by reading and executing a program corresponding to the pre-processing function 442 from the memory 41, the processing circuitry 44 is configured to perform a pre-processing process on the detection data output from the DAS 18. For example, the pre-processing function 442 performs the pre-processing process such as a logarithmic converting process, an offset correcting process, a sensitivity correcting process between the channels, a beam hardening correcting process, and/or the like, on the detection data output from the DAS 18. The data resulting from the pre-processing process may be referred to as raw data. Further, the detection data before performing the pre-processing process and the raw data resulting from the pre-processing process may collectively be referred to as projection data.

Further, the generating function 443 is configured to generate CT image data on the basis of the raw data having been corrected. More specifically, the generating function 443 generates the CT image data by performing a reconstructing process on the corrected raw data, by implementing a filter correction back projection method, a successive approximation reconstruction method, or the like. Further, on the basis of an input operation received from the operator via the input interface 43 or the like, the generating function 443 is configured to convert the generated CT image data into tomographic image data on an arbitrary cross-section or three-dimensional image data, by using a publicly-known method. Further, the generating function 443 is configured to store the tomographic image data and/or the three-dimensional image data resulting from the conversion, into the memory 41.

Further, by reading and executing a program corresponding to the output function 444 from the memory 41, the processing circuitry 44 is configured to output tomographic image data, three-dimensional image data, CT image data, and/or the like. For example, the processing circuitry 44 causes the display 42 to display the tomographic image data and/or the three-dimensional image data. Further, for example, the processing circuitry 44 outputs the tomographic image data, the three-dimensional image data, and/or the CT image data to an external apparatus (e.g., a server apparatus that stores therein image data) connected to the X-ray CT apparatus 1 via a network.

In the X-ray CT apparatus 1 illustrated in FIG. 1, the processing functions are stored in the memory 41 in the form of computer-executable programs. The processing circuitry 44 is a processor configured to realize the functions corresponding to the programs, by reading and executing the programs from the memory 41. In other words, the processing circuitry 44 that has read the programs has the functions corresponding to the read programs. Further, although FIG. 1 illustrates the example in which the processing functions, namely, the system controlling function 441, the pre-processing function 442, the generating function 443, and the output function 444, are realized by the single processing circuit (i.e., the processing circuitry 44), possible embodiments are not limited to this example. For instance, the processing circuitry 44 may be structured by combining together a plurality of independent processors so that the processing functions are realized as a result of the processors executing the programs. Further, the processing functions included in the processing circuitry 44 may be realized as being distributed among, or integrated together into, one or more processing circuits, as appropriate.

An exemplary configuration of the X-ray CT apparatus 1 has thus been explained. The X-ray CT apparatus 1 configured as described above makes it possible to perform one selected from between the dual-energy acquisition and the multi-energy acquisition, by using a fast switching method while employing the one or more DASs 18 that use the sequential acquisition method. More specifically, the one or more DAS 18 included in the X-ray CT apparatus 1 are configured to sequentially acquire, for each view, the signals of the X-rays detected by the plurality of detecting elements included in the X-ray detector 12. Further, the system controlling function 441 included in the X-ray CT apparatus 1 is configured to change the energy of X-rays for every one or more views, so that the energy at the time of the generation of the X-rays detected by each of the plurality of detecting elements is constant among the detecting elements in correspondence with the one or more views. In the following sections, processes performed by the X-ray CT apparatus 1 according to the first embodiment will be explained in detail.

Further, in the present embodiment, an example will be explained in which the dual-energy acquisition is performed. Further, as an example in the present embodiment, the situation will be explained in which the X-ray CT apparatus 1 includes a plurality of DASs 18, while each of the DASs 18 is configured to sequentially acquire the signals of the X-rays detected by detecting elements of which the quantity is equal to n (detecting elements 121, ..., 12m, ..., and 12n) and which are arranged along the row direction.

Further, among the plurality of detecting elements, a plurality of detecting elements 121 from which the signals of the X-rays are acquired substantially simultaneously by the plurality of DASs 18 may be referred to as a first group of detecting elements. Further, among the plurality of detecting elements, a plurality of detecting elements 12n from which the signals of the X-rays are acquired substantially simultaneously by the plurality of DASs 18 may be referred to as an n-th group of detecting elements, where n is an integer of 2 or larger.

During a CT scan, under control of the system controlling function 441, the X-ray tube 11 is configured to generate the X-rays, by rotating while opposing the X-ray detector 12. In this situation, the detecting elements included in the X-ray detector 12 are configured to detect X-rays that have passed through the patient P. Further, the DASs 18 are configured to acquire the signals of the X-rays detected by the detecting elements.

Next, the acquisition of the signals by the DASs 18 and the control over the energy of the X-rays exercised by the system controlling function 441 will be explained, with reference to FIG. 2. In FIG. 2, the horizontal axis corresponds to the row direction, whereas the vertical axis corresponds to time. The energy E1 and the energy E2 illustrated in FIG. 2 are energy levels at the time of generating the X-rays. The energy E1 and the energy E2 are expressed with mutually-different values. Further, the X-ray radiation time periods illustrated in FIG. 2 indicate the time periods during which the detecting elements are radiated by X-rays. FIG. 2 is a chart for explaining the control over the energy of the X-rays according to the first embodiment. As illustrated in FIG. 2, the DAS 18 is configured to sequentially acquire, for each view, n signals of the X-rays detected by the n detecting elements. More specifically, the DAS 18 sequentially acquires the signals of the X-rays in the time period from the time As11 to the time Ae11. Further, with respect to the following view, the DAS 18 sequentially acquires the signals of the X-rays in the time period from the time As12 to the time Ae12. Further, with respect to the subsequent following view, the DAS 18 sequentially acquires the signals of the X-rays in the time period from the time As13 to the time Ae13.

More specifically, at the time As11, the DAS 18 reads and amplifies an electric charge integrated by the detecting element 121 that is among the n detecting elements arranged along the row direction and further performs an A/D conversion. In other words, at the time As11, the DAS 18 acquires the signal of the X-rays detected by the detecting element 121. Further, after the time As11, the DAS 18 sequentially acquires the signals of the X-rays detected by the detecting elements such as the detecting element 12m. Further, at the time Ae11, the DAS 18 acquires the signal of the X-rays detected by the detecting element 12n.

As explained above, the DAS 18 acquires the signals of the X-rays in the time period from the time As11 to the time Ae11. For example, in the time period from the time As11 to the time Ae11, the DAS 18 reads the electric charge from each of the detecting elements. Alternatively, in the time period from the time As11 to the time Ae11, the DAS 18 performs an amplifying process on each of the detecting elements. Alternatively, in the time period from the time As11 to the time Ae11, the DAS 18 performs an A/D conversion on each of the detecting elements. In this situation, as illustrated in FIG. 2, while the DAS 18 is acquiring the signals of the X-rays (in the time period from the time As11 to the time Ae11), the system controlling function 441 stops the generation of X-rays.

Further, at the time Is11 later than the time Ae11, the system controlling function 441 causes X-rays having the energy E1 to be generated. After that, in the time period from the time Is11 to the time Ie11, the system controlling function 441 causes X-rays having the energy E1 to be generated and subsequently stops the generation of X-rays. For example, in the time period from the time Is11 to the time Ie11, the system controlling function 441 causes pulse X-rays having the energy E1 to be generated. In other words, while the DAS 18 is acquiring no signals of X-rays, the system controlling function 441 causes the X-rays in a pulse form to be generated. For example, while the DAS 18 is performing no A/D conversion, the system controlling function 441 causes the X-rays in the pulse form to be generated.

For example, before the scan is started, the system controlling function 441 obtains timing of the signal acquisitions of the DAS 18. In one example, as the timing of the signal acquisitions performed by the DAS 18, the system controlling function 441 obtains time information such as the times As11, Ae11, As12, Ae12, As13, Ae13, and so on illustrated in FIG. 2. In another example, as the timing of the signal acquisitions performed by the DAS 18, the system controlling function 441 obtains the length of time during which the DAS 18 acquires the signals of the X-rays with respect to one view (the length of the time period from the time As11 to the time Ae11) and the cycle in which the DAS 18 acquires the signals of the X-rays (the length of the time period from the time As11 to the time As12). Further, in accordance with the timing of the signal acquisitions performed by the DAS 18, the system controlling function 441 causes the X-rays to be generated or stops the generation of X-rays.

Subsequently, the DAS 18 acquires the signals of the X-rays in the time period from the time As12, which is later than the time Ie11, to the time Ae12. In this situation, while the DAS 18 is acquiring the signals of the X-rays (in the time period from the time As12 to the time Ae12), the system controlling function 441 stops the generation of X-rays. For example, while the DAS 18 is performing an A/D conversion on each of the detecting elements, the system controlling function 441 stops the generation of X-rays. Further, at the time Is12, which is later than the time Ae12, the system controlling function 441 causes X-rays having the energy E2 to be generated. For example, while the generation of X-rays is stopped (e.g., in the time period from the time Ie11 to the time Is12), the system controlling function 441 changes the setting of the energy of the X-rays generated from the X-ray tube 11 from the energy E1 to the energy E2. Further, by controlling the X-ray high-voltage device 14, the system controlling function 441 arranges tube voltage corresponding to the changed setting to be applied to the X-ray tube 11. Further, at the time Is12, the X-ray tube 11 generates X-rays having the energy E2. Further, the system controlling function 441 causes X-rays having the energy E2 to be generated in the time period from the time Is12 to the time Ie12 and subsequently stops the generation of X-rays. Further, in the time period from the time As13, which is later than the time Ie12, to the time Ae13, the DAS 18 performs an A/D conversion on each of the detecting elements.

As illustrated in FIG. 2, for each view, while the DAS 18 is performing an A/D conversion on each of the detecting elements, the system controlling function 441 stops the generation of X-rays. In other words, the system controlling function 441 causes the X-rays to be generated only in the time period during which all the detecting elements (the detecting elements 121, . . . , 12m, . . . , and 12n) are integrating the electric charges for mutually the same view. As a result, it is possible to arrange the energy at the time of the generation of the X-rays detected by the detecting elements to be constant among the detecting elements, for each view.

For example, for the view (a view V11) corresponding to the time As11 to the time Ae12, the generation of X-rays is stopped in the time period from the time As11 to the time Is11 and in the time period from the time Ie11 and the time Ae12, so that none of the plurality of detecting elements is radiated by X-rays. In contrast, in the time period from the time Is11 to the time Ie11, all of the plurality of detecting elements are radiated by the X-rays having the energy E1.

In this situation, the energy at the time of the generation of the X-rays detected by the plurality of detecting elements can be calculated, for each of the detecting elements, as the product of the X-ray radiation time period (the time period from the time Is11 to the Ie11) and the energy E1. In other words, for the view V11, the energy at the time of the generation of the X-rays detected by each of the plurality of detecting elements is constant among the detecting elements.

Similarly, for the view (hereinafter, "view V12") corresponding to the time period from the time As12 to the time Ae13, the generation of X-rays is stopped in the time period from the time As12 to the time Is12 and in the time period from the time Ie12 and the time Ae13, so that none of the plurality of detecting elements is radiated by X-rays. In contrast, in the time period from the time Is12 to the time Ie12, all of the plurality of detecting elements are radiated by the X-rays having the energy E2.

In this situation, the energy at the time of the generation of the X-rays detected by the plurality of detecting elements can be calculated, for each of the detecting elements, as the product of the X-ray radiation time period (the time period from the time Is12 to the Ie12) and the energy E2. In other words, for the view V12, the energy at the time of the generation of the X-rays detected by each of the plurality of detecting elements is constant among the detecting elements.

As illustrated in FIG. 2, the system controlling function 441 is configured to change the energy of the X-rays for each view, while ensuring that the energy at the time of the generation of the X-rays detected by each of the plurality of detecting elements is constant among the detecting elements for each view. For example, as illustrated in FIG. 2, the system controlling function 441 causes the X-rays having the energy E1 or the X-rays having the energy E2 to be generated for each view. In other words, by changing the energy of the X-rays as illustrated in FIG. 2, the system controlling function 441 is able to perform the dual-energy acquisition by using the fast switching method, while employing the DAS 18 that uses the sequential acquisition method.

Further, on the basis of the signals of the X-rays acquired in the dual-energy acquisition, the DAS 18 is configured to generate the detection data and to output the generated detection data to the processing circuitry 44. Subsequently, the pre-processing function 442 is configured to perform the pre-processing process on the detection data. Further, on the basis of the projection data on which the pre-processing process has been performed, the generating function 443 is configured to generate CT image data and to also perform a process (hereinafter, "discriminating process") of discriminating the types, the atomic numbers, the density levels, and the like of the substances included in the patient P, by using the notion that different substances have different X-ray absorption characteristics. Alternatively, the discriminating process may be performed by an external apparatus. For example, the output function 444 may output the projection data (either the detection data before the pre-processing process is performed or the raw data after the pre-processing process is performed) to the external apparatus connected to the X-ray CT apparatus 1 via a network so that the external apparatus performs the discriminating process.

Although FIG. 2 indicates that the time Ie11 and the time As12 are approximately the same time as each other, the time Ie11 may be earlier than the time As12. Further, although FIG. 2 indicates that the time Is12 and the time Ae12 are approximately the same time as each other, the time Is12 may be later than the time Ae12. For example, the system controlling function 441 may be configured to stop the generation of X-rays for a time period longer than the time period in which the DAS 18 is performing an A/D conversion on each of the detecting elements. Further, instead of stopping the generation of X-rays, the system controlling function 441 may block the X-rays to be radiated onto the X-ray detector 12, by controlling the collimator 17. In other words, at least while the DAS 18 is performing the A/D conversion on each of the detecting elements, the system controlling function 441 stops the radiation of the X-rays onto the X-ray detector 12.

Further, in consideration of the possibility that a residual component from the X-rays becoming incident may be detected by the detecting elements even after the radiation of the X-rays is stopped, the system controlling function 441 may be configured to stop the radiation of the X-rays onto the X-ray detector 12 even before the DAS 18 starts the A/D conversion. In that situation, the system controlling function 441, at first, obtains the length of the time period during which the residual component from the X-rays becoming incident is detected by the detecting elements.

For example, when the X-ray detector 12 is a detector of an indirect-conversion type, the X-ray detector 12 includes a scintillator configured to convert X-rays into light and a photodiode configured to detect the light resulting from the conversion. In this situation, while the X-rays are being radiated, an electric charge generated within the photodiode may be trapped at a trap level on the inside. Further, after the radiation of the X-rays is stopped, the electric charge trapped at the trap level may be detected as a residual component of the incident X-rays.

In one example, during a calibration process, the system controlling function 441 measures the length L1 of the time period during which the residual component from the incident X-ray is detected by the detecting elements after the radiation of the X-rays is stopped and further stores the measured length L1 into the memory 41. Further, before the scan is started, the system controlling function 441 obtains the length L1 of the time period from the memory 41. After that, in addition to the time period during which the DAS 18 is performing the A/D conversion on each of the detecting elements, the system controlling function 441 stops the radiation of the X-rays also during the time period from the point in time earlier, by the time length L1 or longer, than the time when the DAS 18 starts the A/D conversion, to the time when the DAS 18 starts the A/D conversion.

FIG. 2 illustrates the example in which, for each view, the radiation of the X-rays onto the X-ray detector 12 is stopped at least while the DAS 18 is performing the A/D conversion on each of the detecting elements; however, possible embodiments are not limited to this example. For instance, as illustrated in FIG. 3, for each view, the system controlling function 441 may stop the radiation of the X-rays onto the X-ray detector 12 or maintain the energy of the X-rays to be constant, at least while the DAS 18 is performing the A/D conversion on each of the detecting elements. FIG. 3 is another chart for explaining the control over the energy of the X-rays according to the first embodiment.

For example, in the time period from the time As21 to the time Ae21, the DAS 18 sequentially performs the A/D conversion. In this situation, while the DAS 18 is performing the A/D conversion on each of the detecting elements (in the time period from the time As21 to the time Ae21), the system controlling function 441 stops the generation of X-rays.

Further, at the time Is21, which is later than the time Ae21, the system controlling function 441 causes X-rays having the energy E1 to be generated. Subsequently, in the time period from the time As22 to the time Ae22, the DAS 18 sequentially performs the A/D conversion. In this situation, while the DAS 18 is performing the A/D conversion on each of the detecting elements (in the time period from the time As22 to the time Ae22), the system controlling function 441 maintains the energy of the X-rays to be constant at the energy E1.

After that, at the time Ie21, which is earlier than the time As23, the system controlling function 441 stops the generation of the X-rays having the energy E1. In other words, in the time period from the time Is21 to the time Ie21, the system controlling function 441 causes X-rays having the energy E1 to be generated. Subsequently, in the time period from the time As23 to the time Ae23, the DAS 18 sequentially performs the A/D conversion. In this situation, while the DAS 18 is performing the A/D conversion on each of the detecting elements (in the time period from the time As23 to the time Ae23), the system controlling function 441 stops the generation of X-rays.

In this situation, for the view (hereinafter, "view V21") corresponding to the time period from the time As21 to the time Ae22, the energy at the time of the generation of the X-rays detected by each of the plurality of detecting elements is not constant among the detecting elements. For example, for the view V21, the energy at the time of the generation of the X-rays detected by the detecting element 121 can be calculated as the product of the X-ray radiation time period (the time period from the time Is21 to the time As22) and the energy E1. In contrast, the energy at the time of the generation of the X-rays detected by the detecting element 12n can be calculated as the product of the X-ray radiation time period (the time period from the time Is21 to the time Ae22) and the energy E1. In this situation, because the length of the time period from the time Is21 to the time As22 is different from the length of the time period from the time Is21 to the time Ae22, the energy at the time of the generation of the X-rays detected by the detecting element 121 has a different value from the energy at the time of the generation of the X-rays detected by the detecting element 12n. Similarly, for the view (hereinafter, "view V22") corresponding to the time period from the time As22 to the time Ae23, the energy at the time of the generation of the X-rays detected by each of the plurality of detecting elements is not constant among the detecting elements.

However, in FIG. 3, when a focus is placed on the two views (the views V21 and V22), the energy at the time of the generation of the X-rays detected by each of the plurality of detecting elements is constant among the detecting elements.

For example, the energy at the time of the generation of the X-rays detected by the detecting element 121 can be calculated as the product of the time period from the time Is21 to the time As22 and the energy E1 for the view V21 and calculated as the product of the time period from the time As22 to the time Ie21 and the energy E1 for the view V22. Accordingly, for the two views (the views V21 and V22), the energy at the time of the generation of the X-rays detected by the detecting element 121 is equal to the product of the time period from the time Is21 to the time Ie21 and the energy E1.

Similarly, for the two views (the views V21 and V22), the energy at the time of the generation of the X-rays detected by each of the plurality of detecting elements can be calculated as the product of the time period from the time Is21 to the time Ie21 and the energy E1, for any of the detecting elements. In other words, for the two views (the views V21 and V22), the energy at the time of the generation of the X-rays detected by each of the plurality of detecting elements is constant among the detecting elements.

After that, at the time Is22, which is later than the time Ae23, the system controlling function 441 causes X-rays having the energy E2 to be generated. Further, the DAS 18 sequentially performs the A/D conversion in the time period from the time As24 to the time Ae24. Further, the DAS 18 sequentially performs the A/D conversion in the time period from the time As25 to the time Ae25. Further, the DAS 18 sequentially performs the A/D conversion in the time period from the time As26 to the time Ae26. In this situation, while the DAS 18 is performing the A/D conversion on each of the detecting elements (i.e., in the time period from the time As24 to the time Ae24, the time period from the time As25 to the time Ae25, and the time period from the time As26 to the time Ae26), the system controlling function 441 maintains the energy of the X-rays to be constant at the energy E2.

After that, at the time Ie22, which is earlier than the time As27, the system controlling function 441 stops the generation of the X-rays having the energy E2. In other words, in the time period from the time Is22 to the time Ie22, the system controlling function 441 causes the X-rays having the energy E2 to be generated. Subsequently, the DAS 18 sequentially performs the A/D conversion in the time period from the time As27 to the time Ae27. In this situation, while the DAS 18 is performing the A/D conversion on each of the detecting elements (in the time period from the time As27 to the time Ae27), the system controlling function 441 stops the generation of X-rays.

In the following sections, the view corresponding to the time period from the time As23 to the time Ae24 will be referred to as a view V23. Further, the view corresponding to the time period from the time As24 to the time Ae25 will be referred to as a view V24. Further, the view corresponding to the time period from the time As25 to the time Ae26 will be referred to as a view V25. Also, the view corresponding to the time period from the time As26 to the time Ae27 will be referred to as a view V26. As illustrated in FIG. 3, for the view V23, the energy at the time of the generation of the X-rays detected by each of the plurality of detecting elements is not constant among the detecting elements. Also, for the view V26, the energy at the time of the generation of the X-rays detected by each of the plurality of detecting elements is not constant among the detecting elements.

However, in FIG. 3, when a focus is placed on the four views (the views V23, V24, V25, and V26), the energy at the time of the generation of the X-rays detected by each of the plurality of detecting elements is constant among the detecting elements. More specifically, for the four views, the energy at the time of the generation of the X-rays detected by each of the plurality of detecting elements is calculated as the product of the time period from the time Is22 to the time Ie22 and the energy E2 for any of the detecting elements. In other words, for the four views, the energy at the time of the generation of the X-rays detected by each of the plurality of detecting elements is constant among the detecting elements.

As illustrated in FIG. 3, the system controlling function 441 changes the energy of the X-rays for every two or more views, while ensuring that the energy at the time of the generation of the X-rays detected by each of the plurality of detecting elements is constant among the detecting elements in correspondence with the two or more views. For example, the system controlling function 441 causes the X-rays having the energy E1 to be generated for the views V21 and V22 and causes the X-rays having the energy E2 to be generated for the views V23, V24, V25, and V26.

For example, the DAS 18 generates the detection data by performing an adding process on the signals of the X-rays for every two or more views, so that the energy at the time of the generation of the X-rays detected by each of the plurality of detecting elements is constant among the detecting elements. Alternatively, the DAS 18 may generate the detection data on the basis of the signals of the X-rays acquired for each view. In that situation, either the processing circuitry 44 or the external apparatus configured to perform the discriminating process performs, as a preprocessing process of the discriminating process, the adding process on the signals of the X-rays for every two or more views, so that the energy at the time of the generation of the X-rays detected by each of the plurality of detecting elements is constant among the plurality of detecting elements. In other words, by changing the energy of the X-rays as illustrated in FIG. 3, the system controlling function 441 is able to perform the dual-energy acquisition by using the fast switching method, while employing the DAS 18 that uses the sequential acquisition method.

FIG. 3 illustrates the example in which the differences in the timing of the integration are small among the detecting elements. As a result, in the example in FIG. 3, after the A/D conversion of the DAS 18 is finished for any one of the views, there is a certain time period (e.g., the time period from the time Ae21 to the time As22) before the DAS 18 starts the A/D conversion for the following view. However, possible embodiments are not limited to this example.

Figure 4:
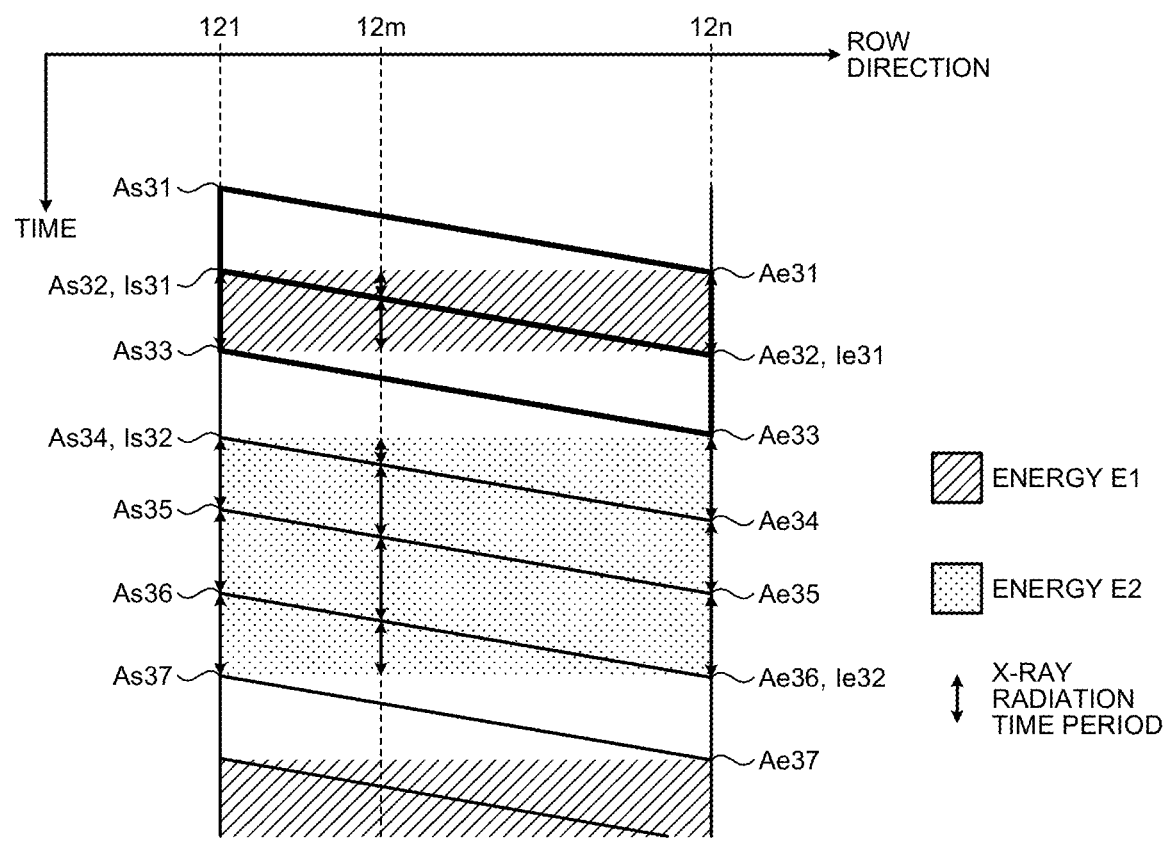
FIG. 4 is yet another chart for explaining the control over the energy of the X-rays according to the first embodiment.

In other words, the differences in the timing of the integration among the detecting elements may be larger than those illustrated in FIG. 3. For example, as illustrated in FIG. 4, after finishing the A/D conversion for one view, the DAS 18 may start the A/D conversion for the following view, without any time lapse. FIG. 4 is yet another chart for explaining the control over the energy of the X-rays according to the first embodiment.

For example, in the time period from the time As31 to the time Ae31, the DAS 18 sequentially performs the A/D conversion. In this situation, while the DAS 18 is performing the A/D conversion on each of the detecting elements (the time period from the time As31 to the time Ae31), the system controlling function 441 stops the generation of X-rays.

Further, at the time Is31, which is the same time as the time Ae31, the system controlling function 441 causes X-rays having the energy E1 to be generated. Further, in the time period from the time As32, which is the same time as the times Ae31 and Is31, to the time Ae32, the DAS 18 sequentially performs the A/D conversion. In this situation, while the DAS 18 is performing the A/D conversion on each of the detecting elements (in the time period from the time As32 to the time Ae32), the system controlling function 441 maintains the energy of the X-rays to be constant at the energy E1.

Subsequently, at the time Ie31, which is the same time as the time Ae32, the system controlling function 441 stops the generation of the X-rays having the energy E1. In other words, in the time period from the time Is31 to the time Ie31, the system controlling function 441 causes the X-rays having the energy E1 to be generated. Further, in the time period from the time As33, which is the same time as the times Ae32 and Ie31, to the time Ae33, the DAS 18 sequentially performs the A/D conversion. In this situation, while the DAS 18 is performing the A/D conversion on each of the detecting elements (in the time period from the time As33 to the time Ae33), the system controlling function 441 stops the generation of X-rays.

After that, at the time Is32, which is the same time as the time Ae33, the system controlling function 441 causes X-rays having the energy E2 to be generated. Further, in the time period from the time As34, which is the same time as the times Ae33 and Is32, to the time Ae34, the DAS 18 sequentially performs the A/D conversion. Further, in the time period from the time As35, which is the same time as the time Ae34, to the time Ae35, the DAS 18 sequentially performs the A/D conversion. Also, in the time period from the time As36, which is the same time as the time Ae35, to the time Ae36, the DAS 18 sequentially performs the A/D conversion. In this situation, while the DAS 18 is performing the A/D conversion on each of the detecting elements (in the time period from the time As34 to the time Ae36), the system controlling function 441 maintains the energy of the X-rays to be constant at the energy E2.

Subsequently, at the time Ie32, which is the same time as the time Ae36, the system controlling function 441 stops the generation of the X-rays having the energy E2. In other words, in the time period from the time Is32 to the time Ie32, the system controlling function 441 causes X-rays having the energy E2 to be generated. After that, in the time period from the time As37, which is the same time as the times Ae36 and Ie32, to the time Ae37, the DAS 18 sequentially performs the A/D conversion. In this situation, while the DAS 18 is performing the A/D conversion on each of the detecting elements (in the time period from the time As37 to the time Ae37), the system controlling function 441 stops the generation of X-rays.

In the following sections, the view corresponding to the time period from the time As31 to the time Ae32 will be referred to as a view V31. Further, the view corresponding to the time period from the time As32 to the time Ae33 will be referred to as a view V32. Also, the view corresponding to the time period from the time As33 to the time Ae34 will be referred to as a view V33. Further, the view corresponding to the time period from the time As34 to the time Ae35 will be referred to as a view V34. Also, the view corresponding to the time period from the time As35 to the time Ae36 will be referred to as a view V35. In addition, the view corresponding to the time period from the time As36 to the time Ae37 will be referred to as a view V36. As illustrated in FIG. 4, for the view V31, the energy at the time of the generation of the X-rays detected by each of the plurality of detecting elements is not constant among the detecting elements. Similarly, for the view V32, the energy at the time of the generation of the X-rays detected by each of the plurality of detecting elements is not constant among the detecting elements. Similarly, for the view V33, the energy at the time of the generation of the X-rays detected by each of the plurality of detecting elements is not constant among the detecting elements. Also, for the view V36, the energy at the time of the generation of the X-rays detected by each of the plurality of detecting elements is not constant among the detecting elements.

However, in FIG. 4, when a focus is placed on the two views (the views V31 and V32), the energy at the time of the generation of the X-rays detected by each of the plurality of detecting elements is constant among the detecting elements. Similarly, when a focus is placed on the four views (the views V33, V34, V35, and V36), the energy at the time of the generation of the X-rays detected by each of the plurality of detecting elements is constant among the detecting elements.

As illustrated in FIG. 4, the system controlling function 441 changes the energy of the X-rays for every two or more views, while ensuring that the energy at the time of the generation of the X-rays detected by each of the plurality of detecting elements is constant among the plurality of detecting elements in correspondence with the two or more views. For example, the system controlling function 441 causes the X-rays having the energy E1 to be generated for the views V31 and V32 and causes the X-rays having the energy E2 to be generated for the views V33, V34, V35, and V36. In other words, even when there are large differences in the timing of the integration among the detecting elements, the system controlling function 441 is able to perform the dual-energy acquisition by using the fast switching method, while employing the DASs 18 that use the sequential acquisition method.

Figure 5:
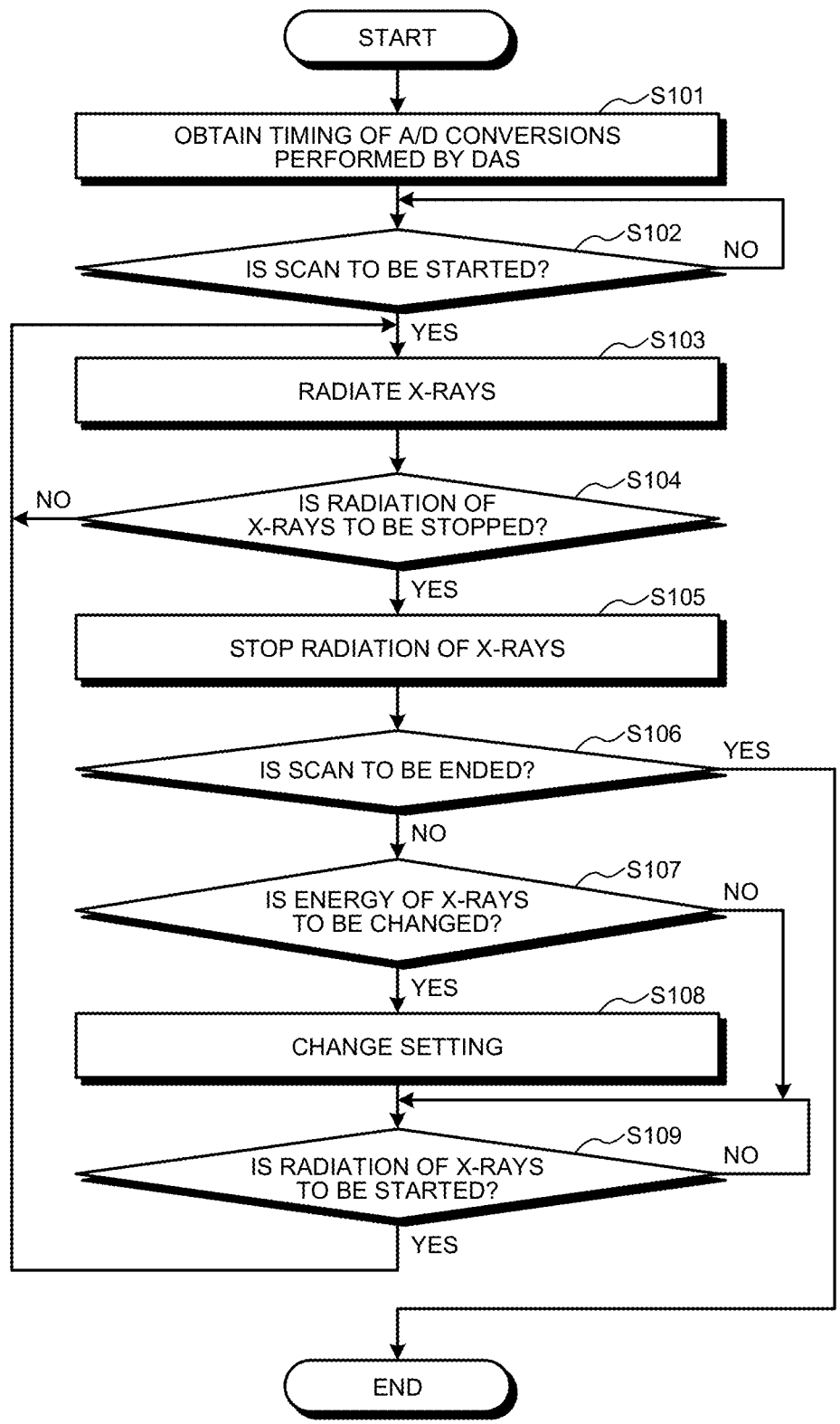
FIG. 5 is a flowchart for explaining a flow in a series of processes performed by the X-ray CT apparatus according to the first embodiment.

Next, an example of a procedure in processes performed by the X-ray CT apparatus 1 will be explained, with reference to FIG. 5. FIG. 5 is a flowchart for explaining the flow in the series of processes performed by the X-ray CT apparatus 1 according to the first embodiment. Steps S101, S102, S103, S104, S105, S106, S107, S108, and S109 are steps corresponding to the system controlling function 441.

First, before the scan is started, the processing circuitry 44 obtains the timing of the A/D conversions performed by the DAS 18 (step S101). Subsequently, the processing circuitry 44 judges whether or not an instruction to start the scan has been received from the operator (step S102). When the instruction to start the scan has not been received (step S102: No), the processing circuitry 44 goes into a stand-by state.

On the contrary, when the instruction to start the scan has been received (step S102: Yes), the processing circuitry 44 rotates the rotating part around the patient P, and also, controls the X-ray high-voltage device 14 so as to supply high voltage to the X-ray tube 11, so that X-rays are radiated (step S103). For example, the processing circuitry 44 causes X-rays having the energy E1 or E2 to be radiated onto the patient P.

Subsequently, the processing circuitry 44 judges whether or not the radiation of the X-rays is to be stopped (step S104). For example, on the basis of the timing of the A/D conversions obtained at step S101, the processing circuitry 44 judges whether or not the radiation of the X-rays is to be stopped before the DAS 18 starts the A/D conversion. For example, the processing circuitry 44 performs the judging process at step S104 once per view.

When it is determined that the radiation of the X-rays is not to be stopped (step S104: No), the processing circuitry 44 returns to step S103 so as to continue the radiation of the X-rays. In other words, the processing circuitry 44 maintains the energy of the X-rays to be constant. On the contrary, when it is determined that the radiation of the X-rays is to be stopped (step S104: Yes), the processing circuitry 44 stops the radiation of the X-rays (step S105). In this situation, the processing circuitry 44 judges whether or not the scan is to be ended (step S106).

When the scan is not to be ended (step S106: No), the processing circuitry 44 judges whether or not the energy of the X-rays is to be changed (step S107). When the energy of the X-rays is to be changed (step S107: Yes), the processing circuitry 44 changes the setting of the energy of the X-rays generated from the X-ray tube 11 (step S108). When the energy of the X-rays is not to be changed (step S107: No) or after step S108 is performed, the processing circuitry 44 judges whether or not the radiation of the X-rays is to be started (step S109). When it is determined that the radiation of the X-rays is not to be started (step S109: No), the processing circuitry 44 goes into a stand-by state. On the contrary, when it is determined that the radiation of the X-rays is to be started (step S109: Yes), the processing circuitry 44 returns to step S103, so that the tube voltage corresponding to the setting is applied to the X-ray tube 11, and the X-rays are radiated. In the situation where it was determined at step S107 that the energy of the X-rays is to be changed, the processing circuitry 44 causes X-rays having energy different from the energy for the preceding view to be radiated. On the contrary, in the situation where it was determined at step S107 that the energy of the X-rays is not to be changed, the processing circuitry 44 causes X-rays having the same energy as the energy for the preceding view to be radiated. Further, when it is determined that the scan is to be ended (step S107: Yes), the processing circuitry 44 ends the process.

As explained above, in the first embodiment, the X-ray tube 11 is configured to generate the X-rays. The X-ray detector 12 includes the one or more families of detecting elements each including the plurality of detecting elements configured to detect the X-rays. Each of the DASs 18 is configured to sequentially acquire, for each view, the signals of the X-rays detected by the plurality of detecting elements. The system controlling function 441 is configured to change the energy of the X-rays for every one or more views, while ensuring that the energy at the time of the generation of the X-rays detected by each of the plurality of detecting elements is constant among the detecting elements in correspondence with the one or more views. Consequently, the X-ray CT apparatus 1 according to the first embodiment is able to perform the dual-energy acquisition by using the fast switching method, while employing the DASs 18 that use the sequential acquisition method.

In other words, the system controlling function 441 is configured to periodically change the energy of the X-rays radiated onto the patient P and to also control the X-ray tube 11 in such a manner that, while the detection data related to one view or a plurality of consecutive views is acquired, an average energy level of the X-rays radiated onto the patient P is substantially equal among the first to the n-th groups of detecting elements. With this arrangement, the X-ray CT apparatus 1 is able to perform the dual-energy acquisition by using the fast switching method, while employing the DASs 18 that use the sequential acquisition method.

Figure 6:
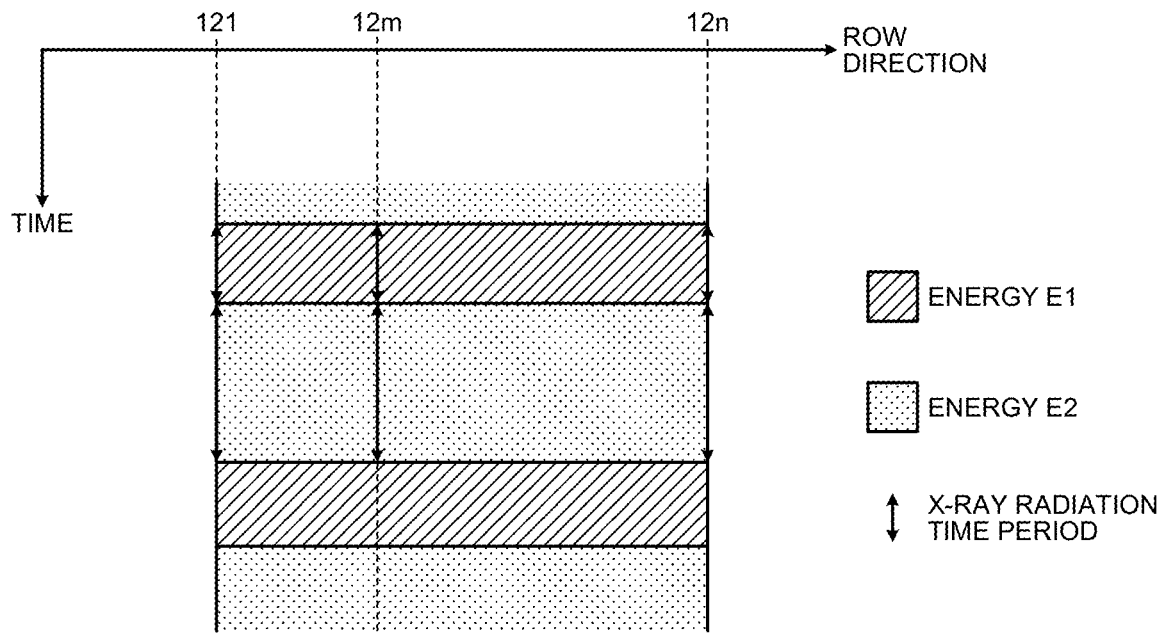
FIG. 6 is a chart for explaining DASs that use a simultaneous acquisition method according to the first embodiment.

Alternatively, it is also possible to perform the dual-energy acquisition by using the fast switching method, while employing DASs that use a simultaneous acquisition method. For example, as illustrated in FIG. 6, by employing the DASs that use the simultaneous acquisition method, it is possible to simultaneously acquire the signals of the X-rays from the n detecting elements (the detecting elements 121, . . . 12m, . . . , and 12n), while ensuring that the X-ray radiation time period at the same energy level within the integration time period is constant among the detecting elements. In other words, by using the n DASs, it is possible to arrange the energy at the time of the generation of the X-rays detected by each of the n detecting elements to be constant among the detecting elements. FIG. 6 is a chart for explaining the DASs that use the simultaneous acquisition method according to the first embodiment.

However, as explained above, when the DASs that use the simultaneous acquisition method are employed, it is necessary to have the DASs in a quantity corresponding to the number of detecting elements included in the X-ray detector 12. For example, when the X-ray detector 12 includes detecting elements arranged in the formation of "1,000" (the channel direction) by "200" (the row direction), it would be necessary to have "200,000" DASs that use the simultaneous acquisition method. Further, when a large number of DASs is used, not only the number of amplifiers and A/D converters provided in the DASs, but also the number of wires used for connecting the DASs to the detecting elements would increase, which would enlarge the scale of the circuit. As a result, when the DASs that use the simultaneous acquisition method were employed, the cost would increase, or restrictions related to space would make the installation difficult.

In contrast, the X-ray CT apparatus 1 makes it possible to perform the dual-energy acquisition by using the fast switching method, while employing the DASs 18 that use the sequential acquisition method. For example, when each of the DASs 18 is configured to sequentially acquire the signals of the X-rays detected by the plurality of detecting elements arranged along the row direction (the detecting elements in one row), it is sufficient when the X-ray CT apparatus 1 includes DASs 18 in a quantity equal to the quantity of rows (hereinafter "the number of rows") (the number of detecting elements arranged in the channel direction) in the X-ray detector 12. In one example, when the X-ray detector 12 includes detecting elements arranged in the formation of "1,000" (the channel direction) by "200" (the row direction), it is sufficient when the X-ray CT apparatus 1 includes "1,000" DASs 18. Accordingly, while making it possible to perform the dual-energy acquisition by using the fast switching method, the X-ray CT apparatus 1 is able to keep the scale of the circuit small by employing the DASs 18 that use the sequential acquisition method and to thus reduce the cost.

Further, as illustrated in FIG. 4, even when there are large differences in the timing of the integration among the detecting elements, the system controlling function 441 is able to perform the dual-energy acquisition by using the fast switching method, while employing the DASs 18 that use the sequential acquisition method. In this situation, "when there are large differences in the timing of the integration among the detecting elements" denotes the situation where, for example, a large number of detecting elements is connected to each of the DASs 18. Accordingly, when a large number of detecting elements is connected to each of the DASs 18 so as to keep the scale of the circuit even smaller, the system controlling function 441 is able to perform the dual-energy acquisition by using the fast switching method.

In the first embodiment described above, the example is explained in which the energy of the X-rays is changed for each view, by varying the energy of the X-rays between before and after stopping the radiation of the X-rays. For example, with reference to FIGS. 2, 3, and 4, the examples were explained in which the X-rays having the energy E1 are radiated, and after the radiation of the X-rays is stopped, the X-rays having the energy E2 are radiated. In contrast, as a second embodiment, an example will be explained in which the energy of the X-rays is changed for each view, by changing the energy of the X-rays while the X-rays are being radiated.

The X-ray CT apparatus 1 according to the second embodiment has a configuration similar to that of the X-ray CT apparatus 1 illustrated in FIG. 1, while a part of the processes performed by the system controlling function 441 is different. In the following sections, some of the constituent elements having the same configurations as those explained in the first embodiment will be referred to by using the same reference characters as in FIG. 1, and the explanations thereof will be omitted.

Figure 7:
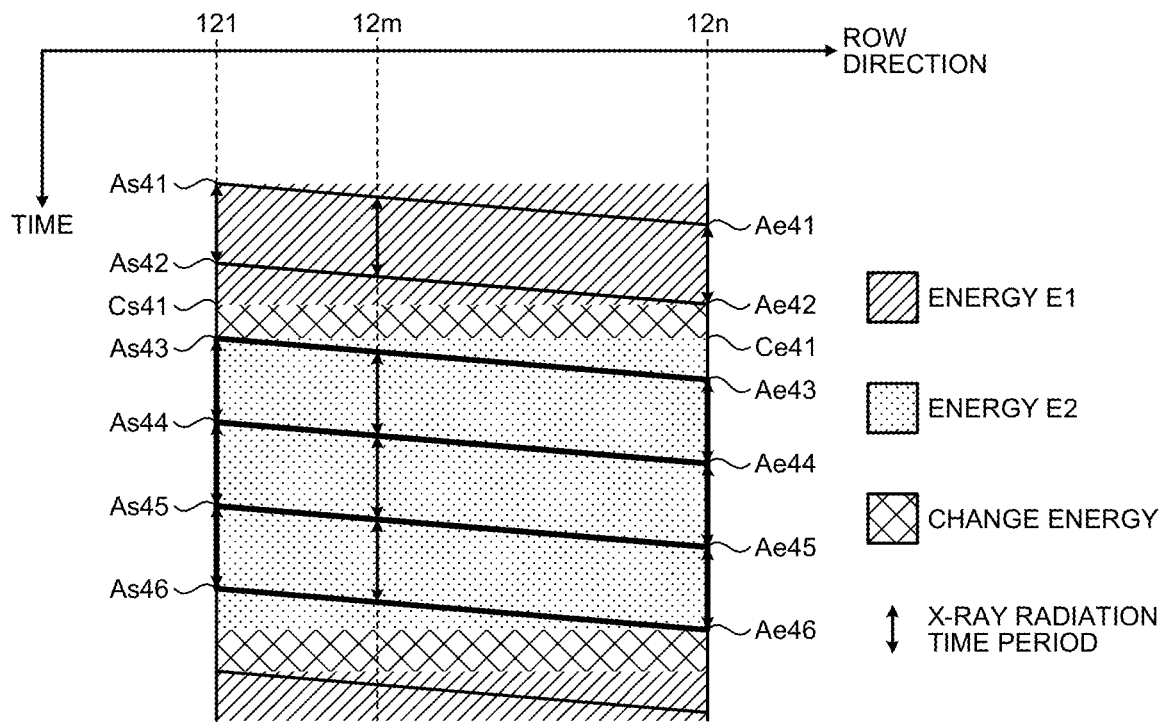
FIG. 7 is a chart for explaining control over energy of X-rays according to a second embodiment.

For example, as illustrated in FIG. 7, the system controlling function 441 is configured to change the energy of the X-rays between the energy E1 and the energy E2, while having the X-rays radiated. FIG. 7 is a chart for explaining the control over the energy of the X-rays according to the second embodiment.

For example, in the time period from the time As41 to the time Ae41, a DAS 18 sequentially performs the A/D conversion. Further, in the time period from the time As42 to the time Ae42, the DAS 18 sequentially performs the A/D conversion. In this situation, at least while the DAS 18 is performing the A/D conversion on each of the detecting elements, the system controlling function 441 maintains the energy of the X-rays to be constant at the energy E1. The view corresponding to the time period from the time As41 to the time Ae42 will hereinafter be referred to as a view V41. In this situation, the view V41 is an example of the first view.

Further, in the time period from the time Cs41, which is later than the time Ae42, to the time Ce41, which is earlier than the time As43, the system controlling function 441 changes the energy of the X-rays from the energy E1 to the energy E2. In other words, after the DAS 18 has finished the A/D conversion for the view V41, the system controlling function 441 changes the energy of the X-rays, before the DAS 18 starts the A/D conversion for the following view V42 (the view corresponding to the time period from the time As42 to the time Ae43). In this situation, the view V42 is an example of the second view.

After that, in the time period from the time As43 to the time Ae43, the DAS 18 sequentially performs the A/D conversion. Further, in the time period from the time As44 to the time Ae44, the DAS 18 sequentially performs the A/D conversion. Also, in the time period from the time As45 to the time Ae45, the DAS 18 sequentially performs the A/D conversion. Further, in the time period from the time As46 to the time Ae46, the DAS 18 sequentially performs the A/D conversion. In this situation, at least while the DAS 18 is performing the A/D conversion on each of the detecting elements, the system controlling function 441 maintains the energy of the X-rays to be constant at the energy E2. The view (the view V45) corresponding to the time period from the time As45 to the time Ae46 is an example of the third view.

As illustrated in FIG. 7, for the view (the view V41) corresponding to the time period from the time As41 to the time Ae42, the X-ray radiation time period with the radiation of the X-rays having the energy E1 is constant among the detecting elements. In other words, for the view V41, the energy at the time of the generation of the X-rays detected by each of the plurality of detecting elements is constant among the detecting elements. Similarly, for the view (the view V43) corresponding to the time period from the time As43 to the time Ae44, the view (the view V44) corresponding to the time period from the time As44 to the time Ae45, and the view V45, the energy at the time of the generation of the X-rays detected by each of the plurality of detecting elements is constant among the detecting elements, for each view. In other words, by changing the energy of the X-rays as illustrated in FIG. 7, the system controlling function 441 is able to perform the dual-energy acquisition by using the fast switching method, while employing the DASs 18 that use the sequential acquisition method.

Figure 8:
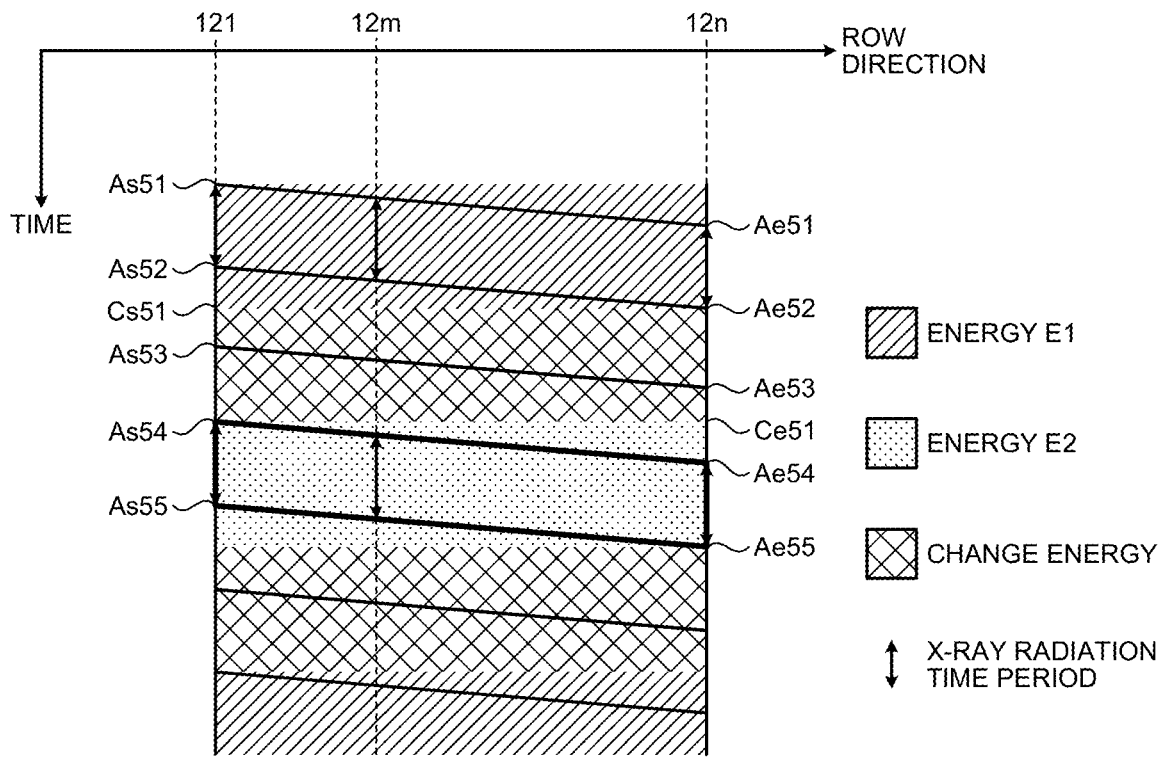
FIG. 8 is another chart for explaining the control over the energy of the X-rays according to the second embodiment.

As for the time period required by changing the energy of the X-rays, there may be a situation where the changing of the energy of the X-rays cannot be completed in the time period after the time when the DAS 18 finishes the A/D conversion for the first view and before the time when the DAS 18 starts the A/D conversion for the following view. In that situation, as illustrated in FIG. 8, the system controlling function 441 changes the energy of the X-rays in the time period after the time when the DAS 18 finishes the A/D conversion for one view and before the time when the DAS 18 starts the A/D conversion for a view later than the following view. FIG. 8 is another chart for explaining the control over the energy of the X-rays according to the second embodiment.

For example, in the time period from the time As51 to the time Ae51, the DAS 18 sequentially performs the A/D conversion. Further, in the time period from the time As52 to the time Ae52, the DAS 18 sequentially performs the A/D conversion. In this situation, at least while the DAS 18 is performing the A/D conversion on each of the detecting elements, the system controlling function 441 maintains the energy of the X-rays to be constant at the energy E1. The view corresponding to the time period from the time As51 to the time Ae52 will hereinafter be referred to as a view V51. In this situation, the view V51 is an example of the first view.

Subsequently, at the time Cs51, which is later than the time Ae52, the system controlling function 441 starts changing the energy of the X-rays from the energy E1 toward the energy E2. After that, in the time period from the time As53 to the time Ae53, the DAS 18 sequentially performs the A/D conversion. Further, at the time Ce51, which is earlier than the time As54, the DAS 18 changes the energy of the X-rays to the energy E2. In other words, the system controlling function 441 changes the energy of the X-rays in the time period after the DAS 18 finishes the A/D conversion for the view V51 and before the DAS 18 starts the A/D conversion for the view V53 (the view corresponding to the time period from the time As53 to the time Ae54), which is later than the following view V52 (the view corresponding to the time period from the time As52 to the time Ae53). In this situation, the view V53 is an example of the second view.

After that, in the time period from the time As54 to the time Ae54, the DAS 18 sequentially performs the A/D conversion. Further, in the time period from the time As55 to the time Ae55, the DAS 18 sequentially performs the A/D conversion. In this situation, at least while the DAS 18 is performing the A/D conversion on each of the detecting elements, the system controlling function 441 maintains the energy of the X-rays to be constant at the energy E2. In this situation, the view (the view V54) corresponding to the time period from the time As54 to the time Ae55 is an example of the third view.

As illustrated in FIG. 8, for the view (the view V51) corresponding to the time period from the time As51 to the time Ae52, the radiation time period with the radiation of the X-rays having the energy E1 is constant among the detecting elements. In other words, for the view V51, the energy at the time of the generation of the X-rays detected by each of the plurality of detecting elements is constant among the detecting elements. Similarly, for the view V54 also, the energy at the time of the generation of the X-rays detected by each of the plurality of detecting elements is constant among the detecting elements. In other words, by changing the energy of the X-rays as illustrated in FIG. 8, the system controlling function 441 is able to perform the dual-energy acquisition by using the fast switching method, while employing the DAS 18 that uses the sequential acquisition method.

Figure 9:
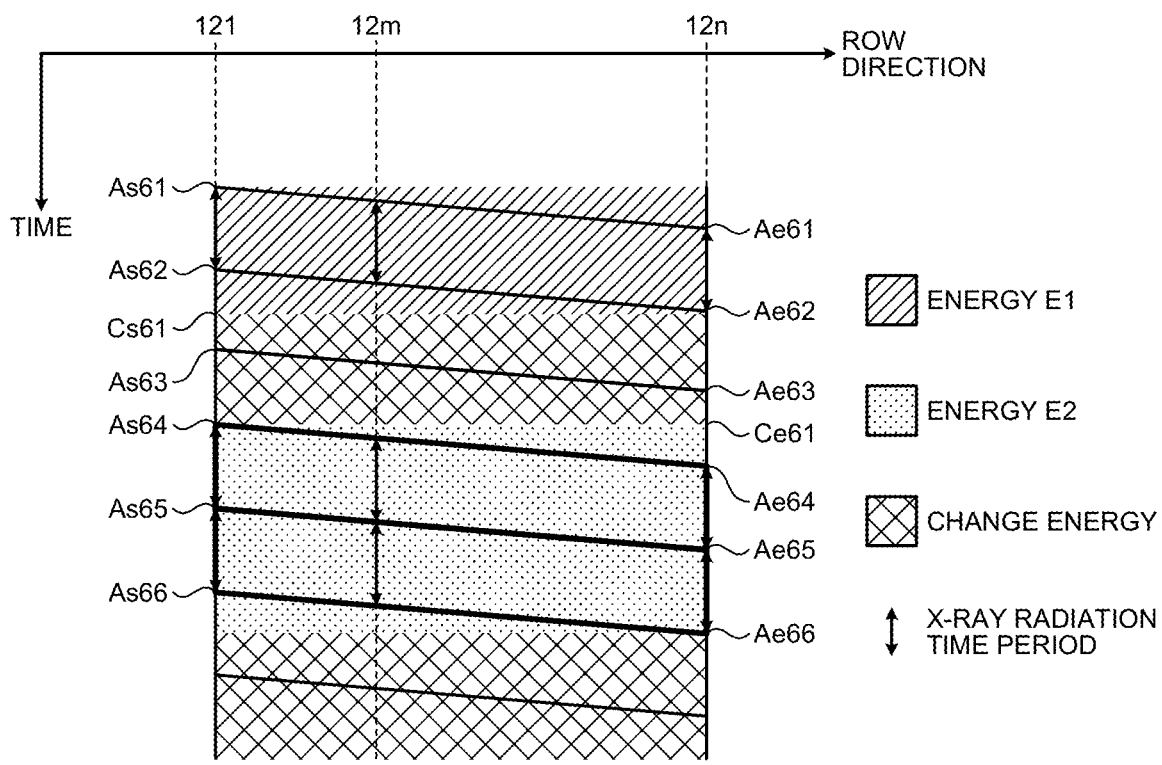
FIG. 9 is yet another chart for explaining the control over the energy of the X-rays according to the second embodiment.

With reference to FIG. 8, the example was explained in which the view (e.g., the view V51) for which the signals are acquired by using the X-rays having the energy E1 and the view (e.g., the view V54) for which the signals are acquired by using the X-rays having the energy E2 repeatedly alternate, one view at a time. However, possible embodiments are not limited to this example. For instance, as illustrated in FIG. 9, the system controlling function 441 may repeatedly alternate one view for which signals are acquired by using the X-rays having the energy E1 and two views for which signals are acquired by using the X-rays having the energy E2. FIG. 9 is yet another chart for explaining the control over the energy of the X-rays according to the second embodiment.

For example, in the time period from the time As61 to the time Ae61, the DAS 18 sequentially performs the A/D conversion. Further, in the time period from the time As62 to the time Ae62, the DAS 18 sequentially performs the A/D conversion. In this situation, at least while the DAS 18 is performing the A/D conversion on each of the detecting elements, the system controlling function 441 maintains the energy of the X-rays to be constant at the energy E1. The view corresponding to the time period from the time As61 to the time Ae62 will hereinafter be referred to as a view V61. In this situation, the view V61 is an example of the first view.

Subsequently, at the time Cs61, which is later than the time Ae62, the system controlling function 441 starts changing the energy of the X-rays from the energy E1 toward the energy E2. After that, in the time period from the time As63 to the time Ae63, the DAS 18 sequentially performs the A/D conversion. Further, at the time Ce61, which is earlier than the time As64, the DAS 18 changes the energy of the X-rays to the energy E2. In other words, the system controlling function 441 changes the energy of the X-rays in the time period after the DAS 18 finishes the A/D conversion for the view V61 and before the DAS 18 starts the A/D conversion for the view V63 (the view corresponding to the time period from the time As63 to the time Ae64), which is later than the following view V62 (the view corresponding to the time period from the time As62 to the time Ae63). In this situation, the view V63 is an example of the second view.

After that, in the time period from the time As64 to the time Ae64, the DAS 18 sequentially performs the A/D conversion. Further, in the time period from the time As65 to the time Ae65, the DAS 18 sequentially performs the A/D conversion. Also, in the time period from the time As66 to the time Ae66, the DAS 18 sequentially performs the A/D conversion. In this situation, at least while the DAS 18 is performing the A/D conversion on each of the detecting elements, the system controlling function 441 maintains the energy of the X-rays to be constant at the energy E2. The view (the view V65) corresponding to the time period from the time As65 to the time Ae66 is an example of the third view.

As illustrated in FIG. 9, for the view (the view V61) corresponding to the time period from the time As61 to the time Ae62, the radiation time period with the radiation of the X-rays having the energy E1 is constant among the detecting elements. In other words, for the view V61, the energy at the time of the generation of the X-rays detected by each of the plurality of detecting elements is constant among the detecting elements. Similarly, also for the view (the view V64) corresponding to the time period from the time As64 to the time Ae65 and the view V65, the energy at the time of the generation of the X-rays detected by each of the plurality of detecting elements is constant among the detecting elements for each view. In other words, by changing the energy of the X-rays as illustrated in FIG. 9, the system controlling function 441 is able to perform the dual-energy acquisition by using the fast switching method, while employing the DAS 18 that uses the sequential acquisition method.

Further, by changing the number of views for which the signals are acquired by using the X-rays having the energy E1 and the number of views for which the signals are acquired by using the X-rays having the energy E2, the system controlling function 441 is able to keep small the difference in the level of precision between the pieces of data corresponding to the different levels of energy. In other words, with respect to a view (hereinafter, a high energy view) for which the signals are acquired by using X-rays having a higher level of energy, the acquired projection data has high image quality, and it is possible to obtain the data with a high level of precision. On the contrary, with respect to a view (hereinafter, a low energy view) for which the signals are acquired by using X-rays having a lower level of energy, the level of precision of the data is relatively low.

To cope with this situation, by arranging the number of low energy views to be larger than the number of high energy views, the system controlling function 441 is able to make the level of precision of the projection data corresponding to the low energy views close to the level of precision of the projection data corresponding to the high energy views. For example, when the energy E1 is higher than the energy E2, the system controlling function 441 is able to make the difference in the level of precision small between the projection data corresponding to the energy E1 and the projection data corresponding to the energy E2, as illustrated in FIG. 9, by repeatedly alternating one view for which the signals are acquired by using the X-rays having the energy E1 and two views for which the signals are acquired by using the X-rays having the energy E2.

In other words, by increasing or decreasing the number of view in accordance with the levels of energy, the system controlling function 441 is able to make small the difference in the level of precision of the data caused by the difference in the levels of energy. Similarly, with the control illustrated in FIGS. 2, 3, 4, 7, and so on, the system controlling function 441 may increase or decrease the number of views in accordance with the levels of energy.

As explained above, the system controlling function 441 according to the second embodiment is configured to change the energy of the X-rays in the time period after the DAS 18 finishes the A/D conversion for the first view and before the DAS 18 starts the A/D conversion for the second view, which is later than the first view. Further, with respect to the plurality of views from the second view to the third view that is later than the second view, the system controlling function 441 maintains the energy of the X-rays to be constant, at least while the DAS 18 is performing the A/D conversion on each of the detecting elements. Consequently, the X-ray CT apparatus 1 according to the second embodiment is able to perform the dual-energy acquisition by using the fast switching method, by changing the energy of the X-rays while radiating the X-rays.

In regard to the above, generally speaking, the generation of the X-rays by the X-ray tube 11 does not stop at the moment when the supply of the tube voltage to the X-ray tube 11 is stopped. Accordingly, stopping the radiation of the X-rays onto the X-ray detector 12 may require cutting off the X-rays. For example, the system controlling function 441 may cut off the X-rays to stop the radiation of the X-rays onto the X-ray detector 12, by controlling the tube voltage of the X-ray tube 11 or by blocking the X-rays with the use of the collimator 17, while taking into consideration the time period it takes for the generation of the X-rays to be stopped after the supply of the tube voltage is stopped.

To cope with this situation, the system controlling function 441 according to the second embodiment changes the energy of the X-rays while having the X-rays radiated. Consequently, by changing the energy of the X-rays for every one or more views, the system controlling function 441 is able to perform the dual-energy acquisition by using the fast switching method, without the need to cut off the X-rays.

In the first and the second embodiments described above, the examples are explained in which the energy at the time of the generation of the X-rays detected by each of the plurality of detecting elements is arranged to be constant among the detecting elements, by using the X-rays having one of the energy levels E1 and E2, with respect to each view. In contrast, as a third embodiment, an example will be explained in which the energy at the time of the generation of the X-rays detected by each of the plurality of detecting elements is arranged to be constant among the detecting elements, by changing the energy of the X-rays within any single view.

The X-ray CT apparatus 1 according to the third embodiment has a configuration similar to that of the X-ray CT apparatus 1 illustrated in FIG. 1, while a part of the processes performed by the system controlling function 441 is different. In the following sections, some of the constituent elements having the same configurations as those explained in the first embodiment will be referred to by using the same reference characters as in FIG. 1, and the explanations thereof will be omitted.

Figure 10:
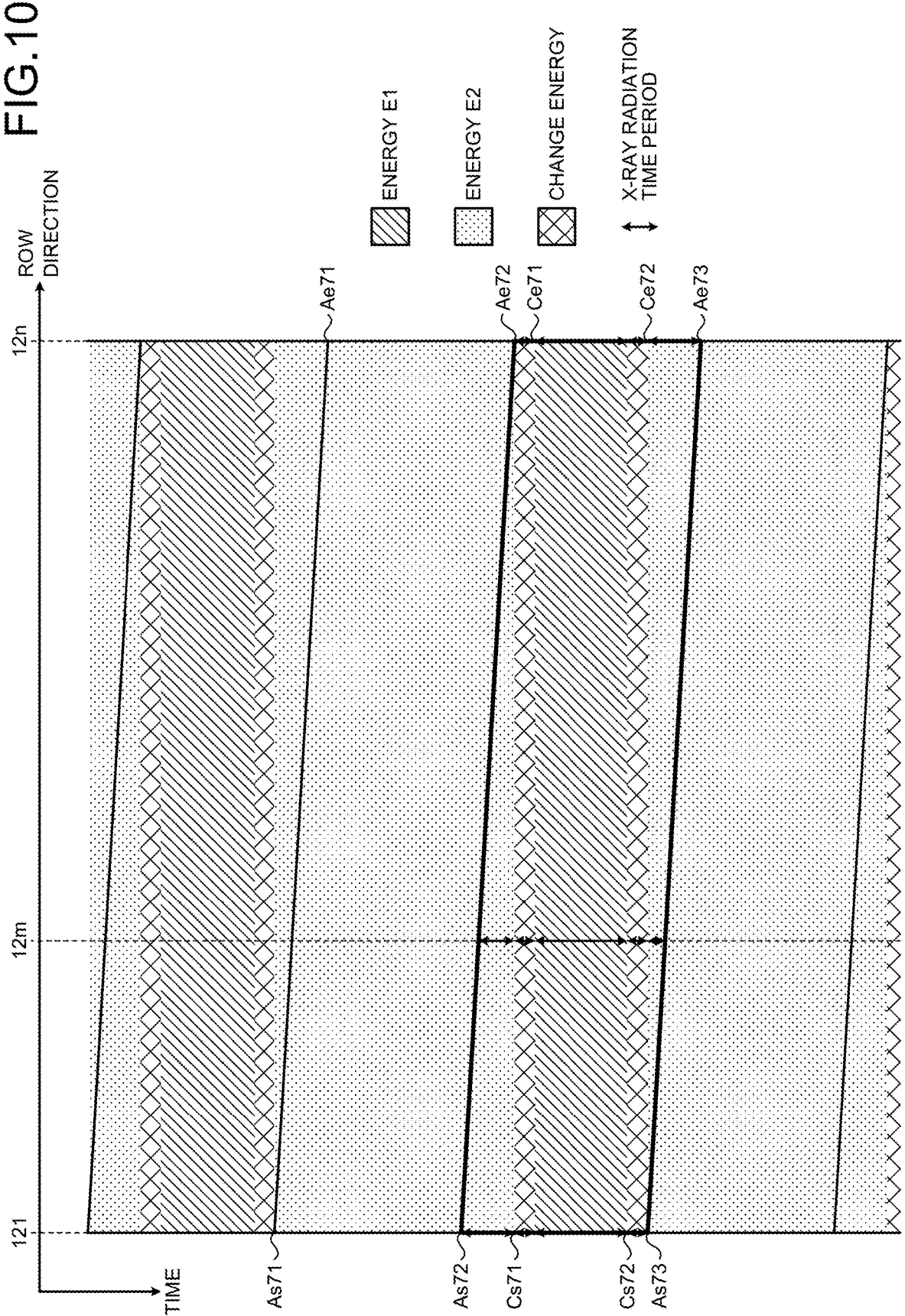
FIG. 10 is a chart for explaining control over energy of X-rays according to a third embodiment.

For example, as illustrated in FIG. 10, the DAS 18 sequentially performs the A/D conversion in the time period from the time As71 to the time Ae71. Subsequently, in the time period from the time As72 to the time Ae72, the DAS 18 sequentially performs the A/D conversion. In this situation, at least while the DAS 18 is performing the A/D conversion on each of the detecting elements, the system controlling function 441 maintains the energy of the X-rays to be constant at the energy E2. FIG. 10 is a chart for explaining the control over the energy of X-rays according to the third embodiment. In the following sections, the view corresponding to the time period from the time As71 to the time Ae72 will be referred to as a view V71. In this situation, the view V71 is an example of the first view.

Subsequently, in the time period from the time Cs71, which is later than the time Ae72, to the time Ce71, the system controlling function 441 changes the energy of the X-rays from the energy E2 to the energy E1. After that, in the time period from the time Ce71 to the time Cs72, the system controlling function 441 maintains the energy of the X-rays to be constant at the energy E1. Subsequently, in the time period from the time Cs72 to the time Ce72, which is earlier than the time As73, the system controlling function 441 changes the energy of the X-rays from the energy E1 to the energy E2. After that, in the time period from the time As73 to the time Ae73, the DAS 18 sequentially performs the A/D conversion. In this situation, at least while the DAS 18 is performing the A/D conversion on each of the detecting elements, the system controlling function 441 maintains the energy of the X-rays to be constant at the energy E2. The view corresponding to the time period from the time As72 to the time Ae73 will hereinafter be referred to as a view V72. In this situation, the view V72 is an example of the second view.

As illustrated in FIG. 10, in the time period after the time Ae72 and before the time As73, the system controlling function 441 changes the energy of the X-rays from the energy E2 to the energy E1, and subsequently, changes the energy of the X-rays from the energy E1 to the energy E2. In other words, in the time period after the DAS 18 finishes the A/D conversion for the view V71 and before the DAS 18 starts the A/D conversion for the view V72 following the view V71, the system controlling function 441 changes the energy of the X-rays from the energy E2 to the energy E1, and subsequently, changes the energy of the X-rays from the energy E1 to the energy E2. With these arrangements, the energy at the time of the generation of the X-rays detected by the plurality of detecting elements is arranged to be constant among the detecting elements, for each view.

At first, for the view V71, the X-ray radiation time period with the radiation of the X-rays having the energy E2 is constant among the detecting elements. In other words, for the view V71, the energy at the time of the generation of the X-rays detected by each of the plurality of detecting elements is constant among the detecting elements.

Subsequently, for the view V72, the X-ray radiation time period with the radiation of the X-rays having the energy E2 is constant among the detecting elements. More specifically, for the view V72, the X-ray radiation time period with the radiation of the X-rays having the energy E2 is, for any of the detecting elements, equal to the length of the time period during which the DAS 18 performs the A/D conversion (the length of the time period from the time As73 to the time Ae73). Alternatively, when there is a time lag from the time Ae72 to the time Cs71 or a time lag from the time Ce72 to the time As73, the X-ray radiation time period with the radiation of the X-rays having the energy E2 is, for any of the detecting elements, equal to the sum of the length of the time period during which the DAS 18 performs the A/D conversion and the these time lags.

Further, while the energy of the X-rays is changing (the time period from the time Cs71 to the time Ce71 and the time period from the time Cs72 to the time Ce72), all of the plurality of detecting elements are radiated by the X-rays. Further, in the time period from the time Ce71 to the time Cs72, all of the plurality of detecting elements are radiated by the X-rays having the energy E1. As a result, for the view V72, the energy at the time of the generation of the X-rays detected by each of the plurality of detecting elements is constant among the detecting elements.

As illustrated in FIG. 10, the system controlling function 441 is configured to change the energy of the X-rays for each view, while ensuring that the energy at the time of the generation of the X-rays detected by each of the plurality of detecting elements is constant among the detecting elements for each view. In other words, by changing the energy of the X-rays as illustrated in FIG. 10, the system controlling function 441 is able to perform the dual-energy acquisition by using the fast switching method, while employing the DAS 18 that uses the sequential acquisition method.

With reference to FIG. 10, the example was explained in which the energy of the X-rays is changed from the energy E2 to the energy E1, in the time period after the DAS 18 finishes the A/D conversion for the first view and before the DAS 18 starts the A/D conversion for the view following the first view, and is subsequently changed from the energy E1 to the energy E2; however, possible embodiments are not limited to this example.

Figure 11:
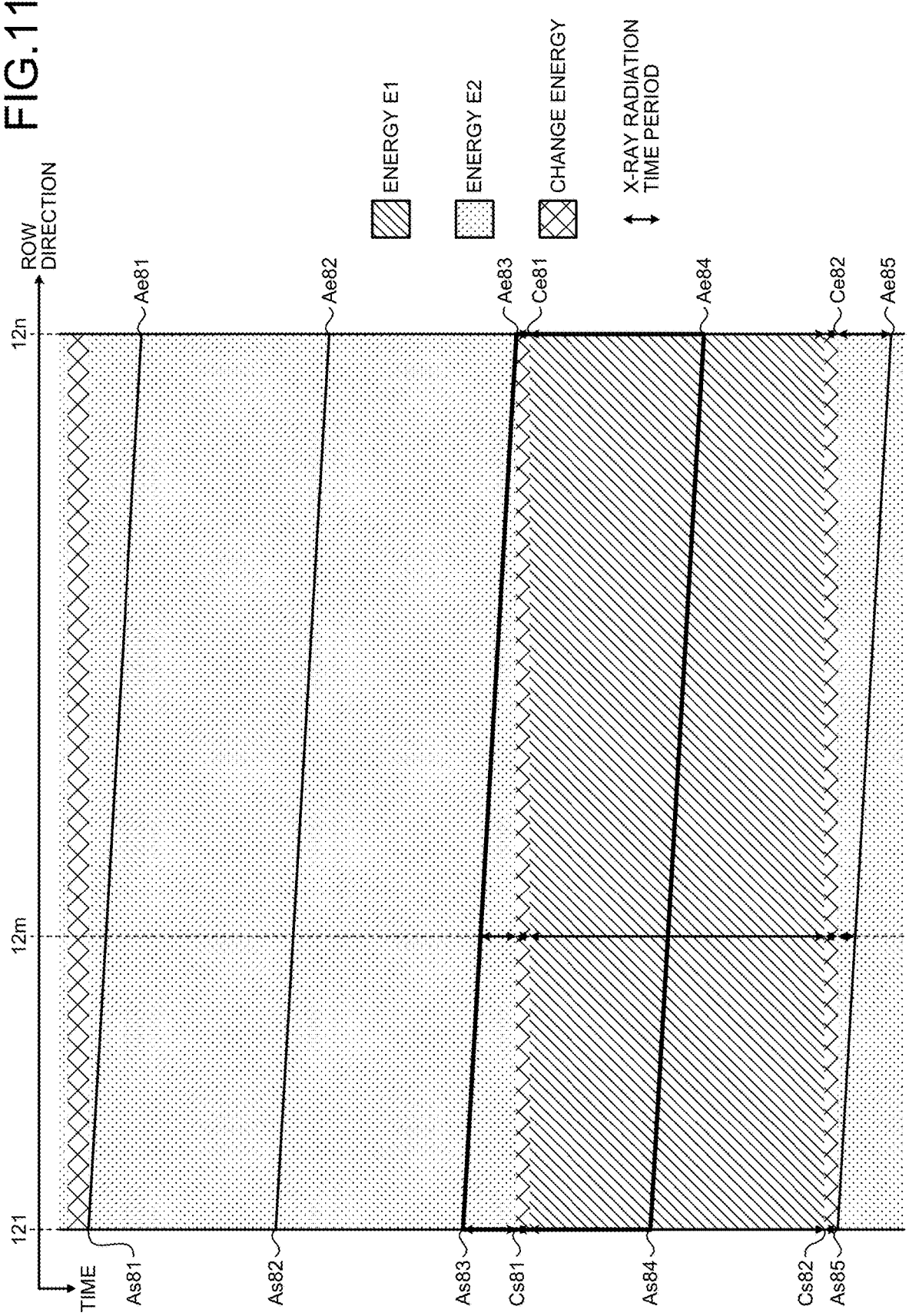
FIG. 11 another chart for explaining the control over the energy of the X-rays according to the third embodiment.

For instance, as illustrated in FIG. 11, in the time period after the DAS 18 finishes the A/D conversion for the first view and before the DAS 18 starts the A/D conversion for a view later than the view following the first view, the system controlling function 441 may change the energy of the X-rays from the energy E2 to the energy E1 and may subsequently change the energy of the X-rays from the energy E1 to the energy E2. FIG. 11 is another chart for explaining the control over the energy of the X-rays according to the third embodiment.

For example, as illustrated in FIG. 11, in the time period from the time As81 to the time Ae81, the DAS 18 sequentially performs the A/D conversion. After that, in the time period from the time As82 to the time Ae82, the DAS 18 sequentially performs the A/D conversion. Subsequently, in the time period from the time As83 to the time Ae83, the DAS 18 sequentially performs the A/D conversion. In this situation, at least while the DAS 18 is performing the A/D conversion on each of the detecting elements, the system controlling function 441 maintains the energy of the X-rays to be constant at the energy E2. The view corresponding to the time period from the time As81 to the time Ae82 will hereinafter be referred to as a view V81. Further, the view corresponding to the time period from the time As82 to the time Ae83 will hereinafter be referred to as a view V82. In this situation, the view V82 is an example of the first view.

Subsequently, in the time period from the time Cs81, which is later than the time Ae83, to the time Ce81, the system controlling function 441 changes the energy of the X-rays from the energy E2 to the energy E1.

After that, in the time period from the time As84 to the time Ae84, the DAS 18 sequentially performs the A/D conversion. In this situation, in the time period from the time Ce81 to the time Cs82, the system controlling function 441 maintains the energy of the X-rays to be constant at the energy E1. The view corresponding to the time period from the time As83 to the time Ae84 will hereinafter be referred to as a view V83.

After that, in the time period from the time Cs82 to the time Ce82, which is earlier than the time As85, the system controlling function 441 changes the energy of the X-rays from the energy E1 to the energy E2. After that, in the time period from the time As85 to the Ae85, the DAS 18 sequentially performs the A/D conversion. In this situation, at least while the DAS 18 is performing the A/D conversion on each of the detecting elements, the system controlling function 441 maintains the energy of the X-rays to be constant at the energy E2. The view corresponding to the time period from the time As84 to the time Ae85 will hereinafter be referred to as a view V84. In this situation, the view V84 is an example of the second view.

As illustrated in FIG. 11, in the time period after the time Ae83 and before the time As85, the system controlling function 441 changes the energy of the X-rays from the energy E2 to the energy E1, and subsequently changes the energy of the X-rays from the energy E1 to the energy E2. In other words, in the time period after the DAS 18 finishes the A/D conversion for the view V82 and before the DAS 18 starts the A/D conversion for the view V84 later than the view V82, the system controlling function 441 changes the energy of the X-rays from the energy E2 to the energy E1, and subsequently changes the energy of the X-rays from the energy E1 to the energy E2. As a result, the energy at the time of the generation of the X-rays detected by the detecting elements is constant among the detecting elements for each view.

First, for the view V81, the X-ray radiation time period with the radiation of the X-rays having the energy E2 is constant among the detecting elements. Similarly, for the view V82, the X-ray radiation time period with the radiation of the X-rays having the energy E2 is constant among the detecting elements. In other words, for the views V81 and V82, the energy at the time of the generation of the X-rays detected by each of the plurality of detecting elements is constant among the detecting elements for each view.

Next, when a focus is placed on the two views, namely the views V83 and V84, the X-ray radiation time period with the radiation of the X-rays having the energy E2 is constant among the detecting elements. More specifically, with respect to the two views, the X-ray radiation time period with the radiation of the X-rays having the energy E2 is, for any of the detecting elements, equal to the length of the time period during which the DAS 18 performs the A/D conversion. Alternatively, when there is a time lag from the time Ae83 to the time Cs81 or a time lag from the time Ce82 to the time As85, the X-ray radiation time period with the radiation of the X-rays having the energy E2 is, for any of the detecting elements, equal to the sum of the length of the time period during which the DAS 18 performs the A/D conversion and the these time lags.

Further, while the energy of the X-rays is changing (the time period from the time Cs81 to the time Ce81 and the time period from the time Cs82 to the time Ce82), all of the plurality of detecting elements are radiated by the X-rays. Further, in the time period from the time Ce81 to the time Cs82, all of the plurality of detecting elements are radiated by the X-rays having the energy E1. As a result, for the two views V83 and V84, the energy at the time of the generation of the X-rays detected by each of the plurality of detecting elements is constant among the detecting elements.

As illustrated in FIG. 11, the system controlling function 441 is configured to change the energy of the X-rays for every one or more views, while ensuring that the energy at the time of the generation of the X-rays detected by each of the plurality of detecting elements is constant among the detecting elements in correspondence with the one or more views. In other words, by changing the energy of the X-rays as illustrated in FIG. 11, the system controlling function 441 is able to perform the dual-energy acquisition by using the fast switching method, while employing the DAS 18 that uses the sequential acquisition method.

The first to the third embodiments have thus been explained. The present disclosure, however, may be carried out in various different modes other than those described in the first to the third embodiments.

In the first to the third embodiments above, as an example of the time period during which the DAS 18 acquires the signals of the X-rays, the time period during which the DAS 18 performs the A/D conversion on each of the detecting elements was explained; however, possible embodiments are not limited to this example. For instance, the system controlling function 441 may control the energy of the X-rays by using, as the time period during which the DAS 18 acquires the signals of the X-rays, the time period during which the DAS 18 reads an electric charge from each of the detecting elements or the time period during which the DAS 18 performs the amplifying process on each of the detecting elements. In one example, for each view, the system controlling function 441 stops the radiation of the X-rays onto the X-ray detector 12, at least while the DAS 18 is reading an electric charge from each of the detecting elements. In another example, for each view, the system controlling function 441 stops the radiation of the X-rays onto the X-ray detector 12, at least while the DAS 18 is performing the amplifying process on each of the detecting elements.

Further, in the first to the third embodiments above, the examples were explained in which the dual-energy acquisition is performed; however, the multi-energy acquisition may be performed by using X-rays having three or more mutually-different types of energy. For example, at least while the DAS 18 is acquiring the signals of the X-rays, the system controlling function 441 stops the radiation of the X-rays onto the X-ray detector 12 and also causes X-rays having the energy E1, X-rays having the energy E2, or X-rays having energy E3, which is different from the energy E1 or the energy E2, to be generated for each view. With these arrangements, the system controlling function 441 is able to perform the multi-energy acquisition by using the fast switching method, while using the X-rays having the three mutually-different types of energy.

Further, in the first to the third embodiments above, the X-ray CT apparatus of a single-tube type was explained as an example of the X-ray CT apparatus 1; however, possible embodiments are not limited to this example. The X-ray CT apparatus 1 may be an X-ray CT apparatus of a so-called multi-tube type in which a plurality of pairs each made up of an X-ray tube and an X-ray detector are installed on a rotating ring.

For example, the X-ray CT apparatus 1 may include a pair made up of a first X-ray tube and a first X-ray detector and another pair made up of a second X-ray tube and a second X-ray detector. Further, the X-ray CT apparatus 1 includes: a first DAS configured to sequentially acquire, for each view, signals of the X-rays detected by the plurality of detecting elements included in the first X-ray detector; and a second DAS configured to sequentially acquire, for each view, signals of the X-rays detected by the plurality of detecting elements included in the second X-ray detector.

In this situation, for example, at least while the first DAS is acquiring the signals of the X-rays, the system controlling function 441 stops the radiation of the X-rays onto the first X-ray detector and also causes X-rays having the energy E1 or E2 to be generated for each view. Further, at least while the second DAS is acquiring the signals of the X-rays, the system controlling function 441 stops the radiation of the X-rays onto the second X-ray detector and also causes X-rays having the energy E3 or E4, which is different from any of the energy E1, the energy E2, and the energy E3, to be generated for each view. With these arrangements, the system controlling function 441 is able to perform the multi-energy acquisition by using the fast switching method, while employing the X-rays having the four mutually-different types of energy.

When a Dual-Energy (DE) acquisition or a Multi-Energy (ME) acquisition is performed by using the fast switching while employing a DAS that uses the sequential acquisition method, a time period allowed (hereinafter, "allowed period") for switching the tube voltage value to be supplied to the X-ray tube tends to be shorter than that in the situation where the DE acquisition or the ME acquisition is performed by using the fast switching while employing a DAS that uses the simultaneous acquisition method. As a result, when the DE acquisition or the ME acquisition is performed by using the fast switching while employing a DAS that uses the sequential acquisition method, imaging conditions (e.g., a tube voltage value, a tube current value, etc.) that can be set may be limited in some situations.

To cope with those situations, by performing the processes described below, the X-ray CT apparatus 1 according to a fifth embodiment is configured to enhance the degree of freedom of the imaging conditions, when performing either a dual-energy acquisition or a multi-energy acquisition by using the fast switching, while employing a DAS that uses the sequential acquisition method.

Figure 12:
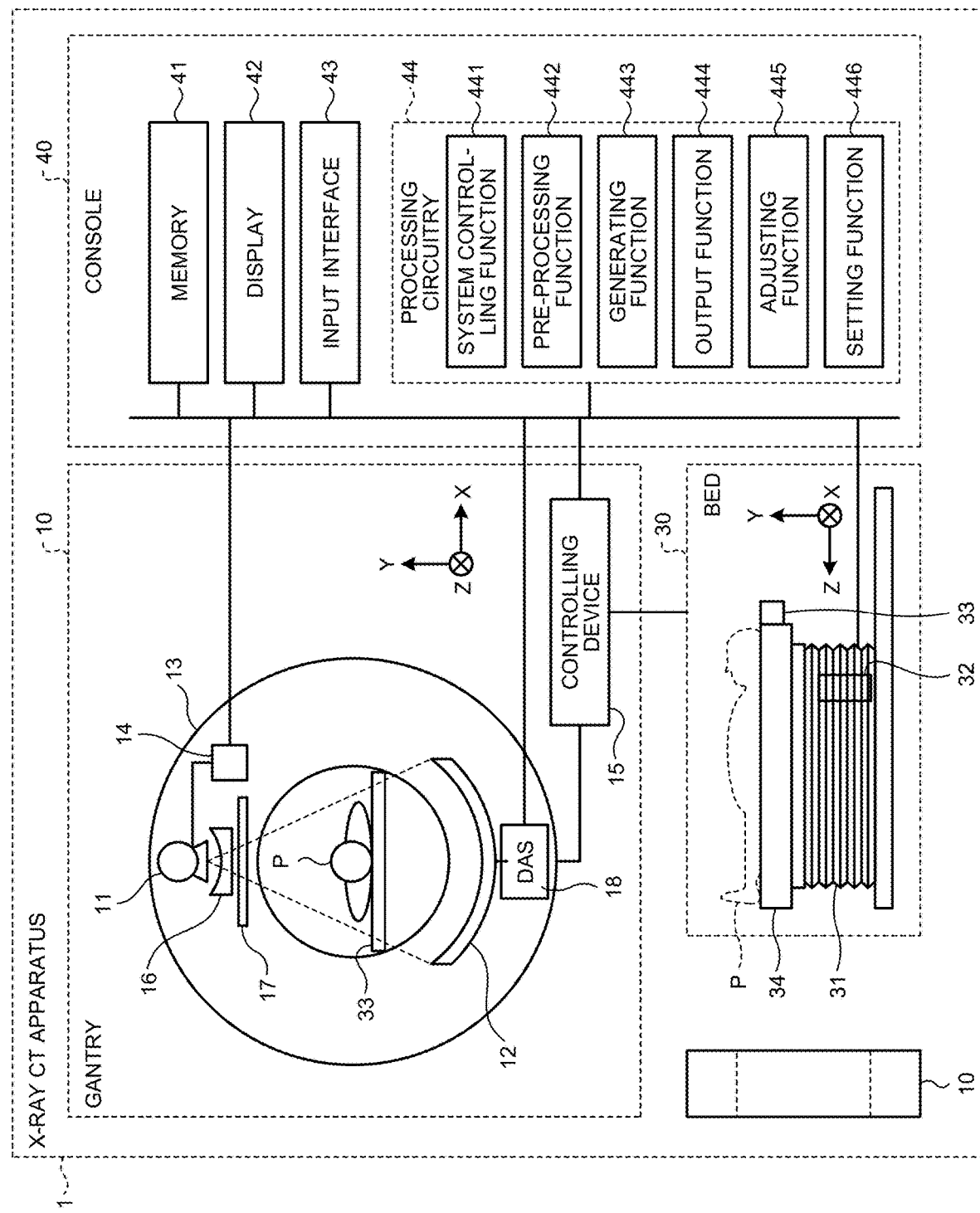
FIG. 12 is a block diagram illustrating an exemplary configuration of an X-ray CT apparatus according to a fifth embodiment.

For example, the processing circuitry 44 included in the X-ray CT apparatus 1 according to the fifth embodiment is configured to further execute an adjusting function 445 and a setting function 446, as illustrated in FIG. 12. The adjusting function 445 is an example of an adjusting unit. The setting function 446 is an example of a setting unit.

For example, by reading and executing a program corresponding to the system controlling function 441 from the memory 41, the processing circuitry 44 controls various types of functions of the processing circuitry 44 on the basis of input operations received from the operator via the input interface 43.

Further, the system controlling function 441 is configured to execute a position determining imaging process by controlling the X-ray CT apparatus 1. For example, the system controlling function 441 executes the position determining imaging process by causing X-rays to be radiated onto the patient P from the X-ray tube 11, by moving the tabletop 33 along the Z-direction while the position of the X-ray tube 11 is fixed at a predetermined rotation angle. Further, by reading and executing a program corresponding to the generating function 443 from the memory 41, the processing circuitry 44 is configured to generate position determining image data on the basis of signals of the X-rays acquired in the position determining imaging process. The position determining image data may be referred to as scanogram image data or scout image data.

Further, the system controlling function 441 is configured to execute a main scan by controlling the X-ray CT apparatus 1. The main scan may simply be referred to an imaging process. For example, by controlling the X-ray high-voltage device 14, the system controlling function 441 supplies the high voltage to the X-ray tube 11. As a result, the X-ray tube 11 generates the X-rays to be radiated onto the patient P. In this situation, by switching the tube voltage value to be supplied to the X-ray tube 11, the system controlling function 441 changes the energy of the X-rays generated by the X-ray tube 11 for every one or more views. In other words, the system controlling function 441 performs either the dual-energy acquisition or the multi-energy acquisition by using the fast switching. The control over the energy of the X-rays exercised by the system controlling function 441 will be explained later. Further, by controlling the bed driving device 32, the system controlling function 441 moves the patient P to the inside of the opening of the gantry 10. Further, the system controlling function 441 is configured to adjust the opening degree and the position of the collimator 17. Further, the system controlling function 441 is configured to rotate the rotating part by controlling the controlling device 15.

Further, by reading and executing a program corresponding to the adjusting function 445 from the memory 41, the processing circuitry 44 is configured to control the allowed period for switching the tube voltage value to be supplied to the X-ray tube 11. Further, for example, by reading and executing a program corresponding to the setting function 446 from the memory 41, the processing circuitry 44 is configured to set imaging conditions. The control over the allowed period and the setting of the imaging conditions will be explained later.

While the imaging process is performed by the system controlling function 441, the DAS 18 generates detection data, by sequentially acquiring the signals of the X-rays in correspondence with each family of detecting elements included in the X-ray detector 12. Further, by reading and executing a program corresponding to the pre-processing function 442 from the memory 41, the processing circuitry 44 is configured to perform a pre-processing process on the detection data output from the DAS 18. For example, the pre-processing function 442 performs the pre-processing process such as a logarithmic converting process, an offset correcting process, a sensitivity correcting process between the channels, a beam hardening correcting process, and/or the like, on the detection data output from the DAS 18. The data resulting from the pre-processing process may be referred to as raw data. Further, the detection data before performing the pre-processing process and the raw data resulting from the pre-processing process may collectively be referred to as projection data.

Further, the generating function 443 is configured to generate CT image data on the basis of the raw data having been corrected. More specifically, the generating function 443 generates the CT image data by performing a reconstructing process on the corrected raw data, by implementing a filter correction back projection method, a successive approximation reconstruction method, or the like. Further, on the basis of an input operation received from the operator via the input interface 43 or the like, the generating function 443 is configured to convert the generated CT image data into a display-purpose CT image (e.g., tomographic image data on an arbitrary cross-section or three-dimensional image data), by using a publicly-known method. Further, the generating function 443 is configured to store the display-purpose CT image resulting from the conversion, into the memory 41.

Further, by reading and executing a program corresponding to the output function 444 from the memory 41, the processing circuitry 44 is configured to output tomographic image data, three-dimensional image data, CT image data, and/or the like. For example, the processing circuitry 44 causes the display 42 to display the tomographic image data and/or the three-dimensional image data. Further, for example, the processing circuitry 44 outputs the tomographic image data, the three-dimensional image data, and/or the CT image data to an external apparatus (e.g., a server apparatus that stores therein image data) connected to the X-ray CT apparatus 1 via a network.

In the X-ray CT apparatus 1 illustrated in FIG. 12, the processing functions are stored in the memory 41 in the form of computer-executable programs. The processing circuitry 44 is a processor configured to realize the functions corresponding to the programs, by reading and executing the programs from the memory 41. In other words, the processing circuitry 44 that has read the programs has the functions corresponding to the read programs.

Further, although FIG. 12 illustrates the example in which the processing functions, namely, the system controlling function 441, the adjusting function 445, the setting function 446, the pre-processing function 442, the generating function 443, and the output function 444, are realized by the single processing circuit (i.e., the processing circuitry 44), possible embodiments are not limited to this example. For instance, the processing circuitry 44 may be structured by combining together a plurality of independent processors so that the processing functions are realized as a result of the processors executing the programs. Further, the processing functions included in the processing circuitry 44 may be realized as being distributed among, or integrated together into, one or more processing circuits, as appropriate.

Figure 13A:
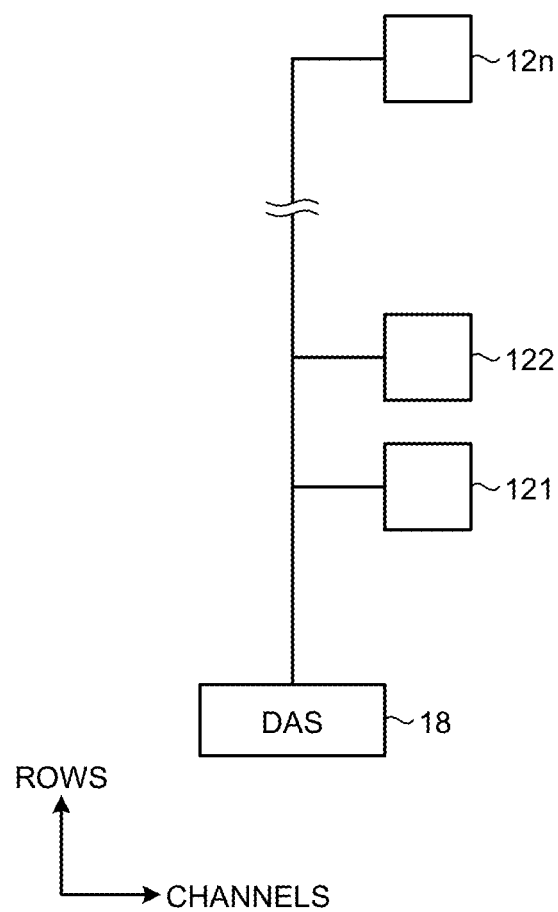
FIG. 13A is a diagram illustrating an example of a DAS according to the fifth embodiment.

Next, the DAS 18 using the sequential acquisition method will be explained. FIG. 13A is a chart illustrating an example of the DAS 18 using the sequential acquisition method according to the fifth embodiment. FIG. 13A illustrates the example in which the DAS 18 sequentially acquires the signals of the X-rays from a family of detecting elements including the n detecting elements (the detecting elements 121 to 12*n*) arranged along the row direction of the X-ray detector 12. In this situation, the X-ray CT apparatus 1 includes, for example, the DAS 18 illustrated in FIG. 13A in a quantity equal to the quantity of channels (hereinafter, "the number of channels") included in the X-ray detector 12. In one example, when the number of channels included in the X-ray detector 12 is "c", the X-ray CT apparatus 1 includes, as illustrated in FIG. 13B, DASs 18 (namely, DASs 181 to 18*c*) of which the quantity is equal to c. The DASs 181, 182, 183, 184, 185, 186, and 18*c* illustrated in FIG. 13B form an example of the DASs 18. Further, FIG. 13B is a chart illustrating the example of the DASs 18 that use the sequential acquisition method according to the fifth embodiment.

In FIG. 13A, among the n detecting elements, the detecting element positioned closest to the DAS 18 is referred to as the detecting element 121; and the detecting element positioned second closest to the DAS 18 is referred to as a detecting element 122. Similarly, in FIG. 13A, the detecting element that is in the n-th closest position to the DAS 18 (i.e., the detecting element positioned farthest from the DAS 18) will be referred to as the detecting element 12$n$.

For example, each of the DASs 18 is connected to each of the detecting elements 121 to 12$n$ via a switch and is configured to sequentially acquire the signals of the X-rays detected by the detecting elements 121 to 12$n$ while the X-ray tube 11 is generating the X-rays. More specifically, at first, the DAS 18 turns on the connection to the detecting element 121 and reads an electric charge integrated by the detecting element 121 as a signal of the X-rays.

Subsequently, the DAS 18 turns off the connection to the detecting element 121, and also, turns on the connection to the detecting element 122 and reads an electric charge integrated by the detecting element 122 as a signal of the X-rays. As the connection thereof to the DAS 18 is turned off, the detecting element 121 starts integrating an electric charge. Similarly, from the detecting elements up to the detecting element 12$n$, the DAS 18 sequentially reads the electric charges integrated by the detecting elements, as signals of the X-rays.

In one example, the DAS 18 sequentially acquires n signals with respect to one view, from the family of detecting elements including the detecting elements 121 to 12$n$. Similarly, the DAS 18 sequentially acquires n signals with respect to the following view, from the family of detecting elements. Although the example was explained in which the signals of the X-rays are sequentially acquired for each view, the DAS 18 may be configured to sequentially acquire the signals of the X-rays for every two or more views.

Further, the example was explained in which the reading is sequentially performed from the detecting element 121 toward the detecting element 12$n$; however, the order of the reading is not limited to that in this example. For instance, the DAS 18 may be configured to read the electric charge integrated by the detecting element 12$n$ at first and to sequentially perform the reading toward the detecting element 121.

Further, for example, the DAS 18 may be configured to read, at first, the electric charge integrated by one of the n detecting elements in an intermediate position and to sequentially perform the reading toward the detecting element 121 and toward the detecting element 12$n$. In other words, the DAS 18 may be configured to sequentially perform the reading from the center of the X-ray detector 12 toward the outside.

In one example, when "n" is an even number, the DAS 18 at first reads the electric charge integrated by the detecting element in the (n/2)-th closest position to the DAS 18. Subsequently, the DAS 18 reads the electric charge integrated by the detecting element in the ((n/2)−1)-th closest position to the DAS 18. After that, the DAS 18 reads the electric charge integrated by the detecting element in the ((n/2)+1)-th closest position to the DAS 18. Further, the DAS 18 reads the electric charge integrated by the detecting element in the ((n/2)−2)-th closest position to the DAS 18. Similarly, from the detecting elements, namely, up to the detecting element 121 and the detecting element 12$n$, the DAS 18 sequentially reads the electric charges integrated by the detecting elements as signals of the X-rays.

Further, although the example was explained in which the signals of the X-rays are sequentially acquired from the family of detecting elements including the n detecting elements arranged along the row direction of the X-ray detector 12, possible embodiments are not limited to this example. For instance, the DAS 18 may be configured to sequentially acquire the signals of the X-rays from a family of detecting elements including a plurality of detecting elements arranged along the channel direction of the X-ray detector 12. In that situation, the X-ray CT apparatus 1 includes, for example, the DASs 18 in a quantity equal to the number of rows included in the X-ray detector 12.

Alternatively, for example, the DAS 18 may be configured to sequentially acquire the signals of the X-rays from a family of detecting elements including all the detecting elements in the X-ray detector 12. In that situation, for example, the X-ray CT apparatus 1 includes only one DAS 18. In other words, the X-ray detector 12 includes one or more families of detecting elements. Further, the X-ray CT apparatus 1 includes one or more DASs 18 configured to sequentially acquire the signals of the X-rays in correspondence with each family of detecting elements.

The exemplary configuration of the X-ray CT apparatus 1 has thus been explained. The X-ray CT apparatus 1 structured as described above is configured to enhance the degree of freedom of the imaging conditions, when performing either the dual-energy acquisition or the multi-energy acquisition by using the fast switching, while employing the one or more DASs 18 that use the sequential acquisition method.

More specifically, the system controlling function 441 is configured to change the energy of the X-rays for every one or more views, by switching the tube voltage value to be supplied to the X-ray tube 11. In other words, the system controlling function 441 performs the dual-energy acquisition or the multi-energy acquisition by using the fast switching. Further, the DAS 18 is configured to sequentially acquire the signals of the X-rays, in correspondence with each family of detecting elements included in the X-ray detector 12. Further, the adjusting function 445 is configured to enhance the degree of freedom of the imaging conditions by controlling the allowed period for switching the tube voltage value, by adjusting one or both of the number of rows and the number of channels included in the family of detecting elements from which the DAS 18 acquires the signals.

Next, processes performed by the X-ray CT apparatus 1 according to the fifth embodiment will be explained in detail. In the present embodiment, as an example, situations with the dual-energy acquisition will be explained. Further, in the present embodiment, as an example, the situation will be explained in which the X-ray CT apparatus 1 includes a plurality of DASs 18, while each of the DASs 18 is connected to the n detecting elements (the detecting elements 121 to 12$n$) arranged along the row direction.

First, an example of the dual-energy acquisition performed by employing a DAS 18 will be explained, with reference to FIG. 14. FIG. 14 is a chart illustrating an example of the dual-energy acquisition employing the DAS 18 that uses the sequential acquisition method according to the fifth embodiment. In FIG. 14, the horizontal axis corresponds to time, whereas the vertical axis corresponds to the row direction of the X-ray detector 12. Further, the energy E1 and the energy E2 illustrated in FIG. 14 are energy levels at the time of generating the X-rays. The energy E1 and the energy E2 are expressed with mutually-different values. In the following sections, an example will be explained in which the energy E1 is higher than the energy E2.

When an imaging process is to be performed, the system controlling function 441 causes X-rays to be generated by supplying the high voltage to the X-ray tube 11 while rotating the rotating part. For example, at least in the time period from the time T111 to the time T114, the system controlling function 441 causes X-rays having the energy E1 to be generated, by supplying a first tube voltage value V1 to the X-ray tube 11. Further, in the time period from the time T114 to the time T115, the system controlling function 441 switches the tube voltage value to be supplied to the X-ray tube 11 from the first tube voltage value V1 to a second tube voltage value V2, which is smaller than the first tube voltage value V1.

Subsequently, at least in the time period from the time T115 to the time T118, the system controlling function 441 causes X-rays having the energy E2 to be generated by supplying the second tube voltage value V2 to the X-ray tube 11. Further, in the time period from the time T118 to the time T119, the system controlling function 441 switches the tube voltage value to be supplied to the X-ray tube 11 from the second tube voltage value V2 to the first tube voltage value V1.

After that, at least in the time period from the time T119 to the time T122, the system controlling function 441 causes X-rays having the energy E1 to be generated, by supplying the first tube voltage value V1 to the X-ray tube 11. Further, in the time period from the time T122 to the time T123, the system controlling function 441 switches the tube voltage value to be supplied to the X-ray tube 11 from the first tube voltage value V1 to the second tube voltage value V2.

Subsequently, at least in the time period from the time T123 to the time T126, the system controlling function 441 causes X-rays having the energy E2 to be generated, by supplying the second tube voltage value V2 to the X-ray tube 11. Further, in the time period from the time T126 to the time T127, the system controlling function 441 switches the tube voltage value to be supplied to the X-ray tube 11 from the second tube voltage value V2 to the first tube voltage value V1.

As explained above, in the example illustrated in FIG. 14, the system controlling function 441 switches the energy of the X-rays for every two views, by switching the tube voltage value supplied to the X-ray tube 11. In that situation, the detecting elements included in the X-ray detector 12 detect the X-rays that have passed through the patient P. Further, each of the plurality of DASs 18 sequentially acquires the signals from the family of detecting elements including the n detecting elements.

More specifically, in the time period from the time T111 to the time T112, each of the DASs 18 is configured to sequentially acquire the n signals from the family of detecting elements. Further, in the time period from the time T113 to the time T114, the DAS 18 is configured to sequentially acquire n signals from the family of detecting elements. Further, in the time period from the time T115 to the time T116, the DAS 18 is configured to sequentially acquire n signals from the family of detecting elements. Further, in the time period from the time T117 to the time T118, the DAS 18 is configured to sequentially acquire n signals from the family of detecting elements. Also, in the time period from the time T119 to the time T120, the DAS 18 is configured to sequentially acquire n signals from the family of detecting elements. Further, in the time period from the time T121 to the time T122, the DAS 18 is configured to sequentially acquire n signals from the family of detecting elements. In addition, in the time period from the time T123 to the time T124, the DAS 18 is configured sequentially acquire n signals from the family of detecting elements. Furthermore, in the time period from the time T125 to the time T126, the DAS 18 is configured to sequentially acquire n signals from the family of detecting elements.

Even more specifically, at the time T111, the DAS 18 reads and amplifies the electric charge integrated by the detecting element 121 that is among the n detecting elements arranged along the row direction and further performs an A/D conversion. In other words, at the time T111, the DAS 18 acquires the signal of the X-rays detected by the detecting element 121. Further, after the time T111, the DAS 18 sequentially acquires the signals of the X-rays detected by the detecting elements. After that, at the time T112, the DAS 18 acquires the signal of the X-rays detected by the detecting element 12n.

Subsequently, in the time period from the time T113 to the time T114, the DAS 18 sequentially acquires the signals of the X-rays from the detecting elements, namely the detecting elements 121 to 12n. In this situation, the energy at the time of the generation of the X-rays detected by the detecting elements, namely the detecting elements 121 to 12n, is constant among the detecting elements.

For example, the energy at the time of the generation of the X-rays detected by the detecting element 121 at the time T113 can be calculated as the product of the time period from the time T111 to the time T113 and the energy E1. Further, the energy at the time of the generation of the X-rays detected by the detecting element 12n at the time T114 can be calculated as the product of the time period from the time T112 to the time T114 and the energy E1. In this situation, as illustrated in FIG. 14, the time period from the time T111 to the time T113 is equal to the time period from the time T112 to the time T114. Accordingly, the energy at the time of the generation of the X-rays detected by the detecting elements 121 and 12n is constant between the detecting elements.

Similarly, with respect to the following view (the view corresponding to the time period from the time T115 to the time T118), the energy at the time of the generation of the X-rays detected by the detecting elements, namely the detecting elements 121 to 12n, is constant among the detecting elements. For example, the energy at the time of the generation of the X-rays detected by the detecting element 121 at the time T117 can be calculated as the product of the time period from the time T115 to the time T117 and the energy E2. Further, the energy at the time of the generation of the X-rays detected by the detecting element 12n at the time T118 can be calculated as the product of the time period from the time T116 to the time T118 and the energy E2. In this situation, as illustrated in FIG. 14, the time period from the time T115 to the time T117 is equal to the time period from the time T116 to the time T118. Accordingly, the energy at the time of the generation of the X-rays detected by the detecting elements 121 and 12n is constant between the detecting elements.

In this situation, as explained above, to ensure that the energy at the time of the generation of the X-rays is constant among the detecting elements for the view corresponding to the time period from the time T115 to the time T118, it is necessary to change the energy at the time of the generation of the X-rays from the energy E1 to the energy E2 in the time period from the time T114 to the time T115 indicated in FIG. 14. In other words, the system controlling function 441 needs to switch the tube voltage value to be supplied to the X-ray tube 11 from the first tube voltage value V1 to the second tube voltage value V2 in the time period from the time T114 to the time T115. The time period allowed for switching the tube voltage value (e.g., the time period from the time T114 to the time T115) may be referred to as an allowed period. Further, as illustrated in FIG. 14, the allowed period used when the signals are sequentially acquired from the family of detecting elements including n detecting elements may be referred to as an allowed period Ln.

Similarly, for the view corresponding to the time period from the time T119 to the time T122, to ensure that the energy at the time of the generation of the X-rays is constant among the detecting elements, it is necessary to switch the tube voltage value to be supplied to the X-ray tube 11 from the second tube voltage value V2 to the first tube voltage value V1 within the allowed period (i.e., the time period from the time T118 to the time T119). Similarly, for the view corresponding to the time period from the time T123 to the time T126, to ensure that the energy at the time of the generation of the X-rays is constant among the detecting elements, it is necessary to switch the tube voltage value to be supplied to the X-ray tube 11 from the first tube voltage value V1 to the second tube voltage value V2 within the allowed period (i.e., the time period from the time T122 to the time T123).

In this situation, when the dual-energy acquisition is performed by using the fast switching while employing the DAS 18 that uses the sequential acquisition method, the allowed period tends to be shorter than that in the situation where the dual-energy acquisition is performed by using the fast switching while employing a DAS that uses the simultaneous acquisition method. In the following sections, the DAS that uses the simultaneous acquisition method will be referred to as a DAS 18a.

Figure 15:
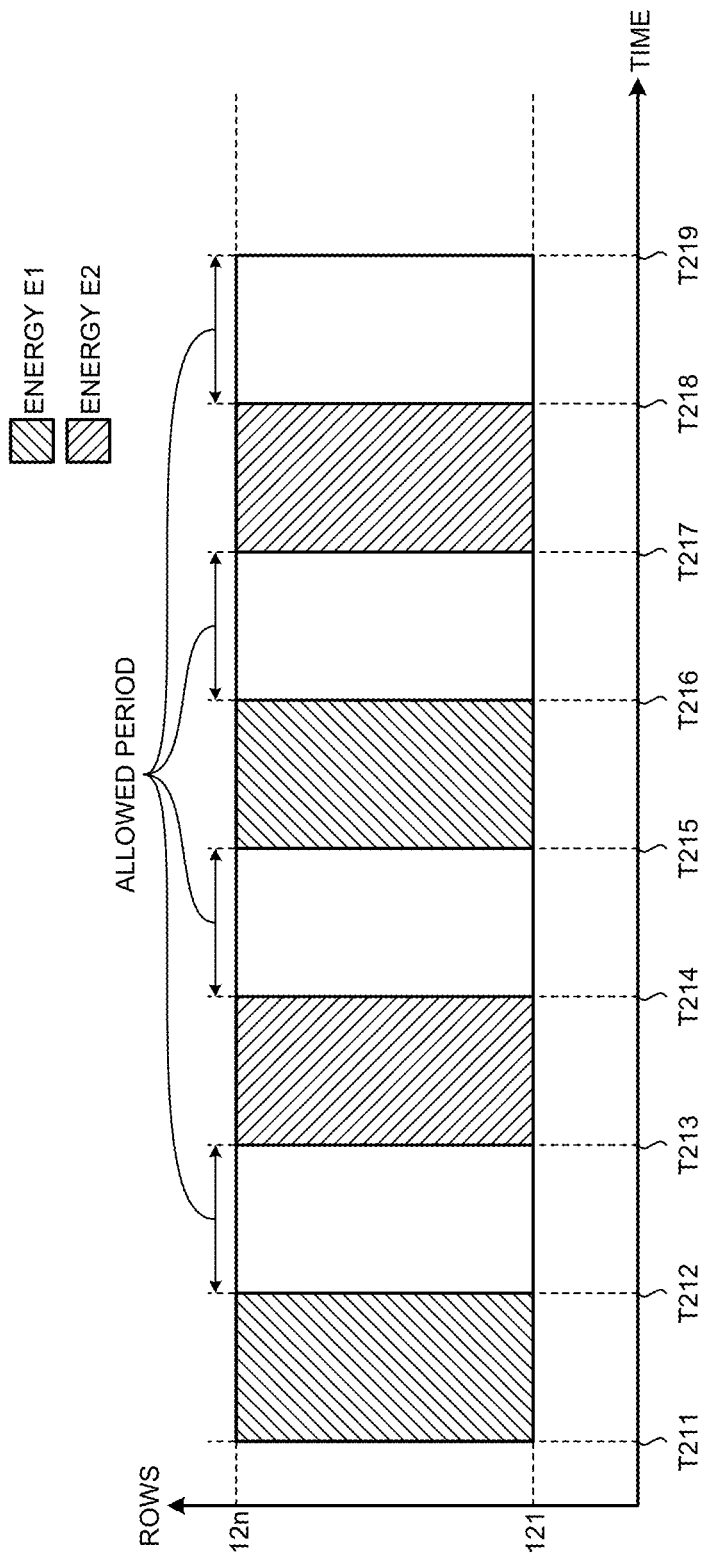
FIG. 15 is a chart illustrating an example of a dual-energy acquisition employing DASs that use a simultaneous acquisition method according to the fifth embodiment.

For example, when the dual-energy acquisition is performed by using the fast switching, while employing DASs 18a that use the simultaneous acquisition method, at least in the time period from the time T211 to the time T212 indicated in FIG. 15, the system controlling function 441 causes X-rays having the energy E1 to be generated by supplying the first tube voltage value V1 to the X-ray tube 11. Further, in the time period from the time T212 to the time T213, the system controlling function 441 switches the tube voltage value to be supplied to the X-ray tube 11 from the first tube voltage value V1 to the second tube voltage value V2. FIG. 15 is a chart illustrating the example of the dual-energy acquisition employing the DASs 18a that use the simultaneous acquisition method according to the fifth embodiment.

Subsequently, at least in the time period from the time T213 to the time T214, the system controlling function 441 causes X-rays having the energy E2 to be generated by supplying the second tube voltage value V2 to the X-ray tube 11. Further, in the time period from the time T214 to the time T215, the system controlling function 441 switches the tube voltage value to be supplied to the X-ray tube 11 from the second tube voltage value V2 to the first tube voltage value V1.

After that, at least in the time period from the time T215 to the time T216, the system controlling function 441 causes X-rays having the energy E1 to be generated by supplying the first tube voltage value V1 to the X-ray tube 11. Further, in the time period from the time T216 to the time T217, the system controlling function 441 switches the tube voltage value to be supplied to the X-ray tube 11 from the first tube voltage value V1 to the second tube voltage value V2.

After that, at least in the time period from the time T217 to the time T218, the system controlling function 441 causes X-rays having the energy E2 to be generated by supplying the second tube voltage value V2 to the X-ray tube 11. Further, in the time period from the time T218 to the time T219, the system controlling function 441 switches the tube voltage value to be supplied to the X-ray tube 11 from the second tube voltage value V2 to the first tube voltage value V1.

As illustrated in FIG. 15, by switching the tube voltage value to be supplied to the X-ray tube 11, the system controlling function 441 switches the energy of the X-rays for every two views. In this situation, the detecting elements included in the X-ray detector 12 detect the X-rays that have passed through the patient P. In this situation, one DAS 18a using the simultaneous acquisition method is provided for each of the detecting elements so as to acquire signals from the corresponding detecting element. For example, for the n detecting elements, namely the detecting elements 121 to 12n, the DASs 18a which use the simultaneous acquisition method and of which the quantity is n are provided. Further, the n DASs 18a are configured to simultaneously acquire the signals from the n detecting elements.

More specifically, in the example illustrated in FIG. 15, for the view corresponding to the time period from the time T211 to the time T212, the n DASs 18a simultaneously acquire the signals from the n detecting elements in the time period from the time T211 to the time T212. Further, for the view corresponding to the time period from the time T213 to the time T214, the n DASs 18a simultaneously acquire the signals from the n detecting elements in the time period from the time T213 to the time T214. Also, for the view corresponding to the time period from the time T215 to the time T216, the n DASs 18a simultaneously acquire the signals from the n detecting elements in the time period from the time T215 to the time T216. Further, for the view corresponding to the time period from the time T217 to the time T218, the n DASs 18a simultaneously acquire the signals from the n detecting elements in the time period from the time T217 to the time T218.

In this situation, the energy at the time of the generation of the X-rays detected by the detecting elements, namely the detecting elements 121 to 12n, is constant among the detecting elements. For example, for the view corresponding to the time period from the time T211 to the time T212, the energy at the time of the generation of the X-rays detected by the n detecting elements can be calculated, for any of the detecting elements, as the product of the time period from the time T211 to the time T212 and the energy E1 and is therefore constant.

Also in the example illustrated in FIG. 15, the system controlling function 441 needs to change the energy of the X-rays within the allowed period. For example, in the time period from the time T212 to the time T213, the system controlling function 441 switches the tube voltage value to be supplied to the X-ray tube 11 from the first tube voltage value V1 to the second tube voltage value V2. Further, in the time period from the time T214 to the time T215, the system controlling function 441 switches the tube voltage value to be supplied to the X-ray tube 11 from the second tube voltage value V2 to the first tube voltage value V1. Also, in the time period from the time T216 to the time T217, the system controlling function 441 switches the tube voltage value to be supplied to the X-ray tube 11 from the first tube voltage value V1 to the second tube voltage value V2. Furthermore, in the time period from the time T218 to the time T219, the system controlling function 441 switches the tube voltage value to be supplied to the X-ray tube 11 from the second tube voltage value V2 to the first tube voltage value V1.

As illustrated in FIGS. 14 and 15, when the dual-energy acquisition is performed by using the fast switching while employing the DASs 18 that use the sequential acquisition method, the allowed period is shorter than that in the situation where the dual-energy acquisition is performed by using the fast switching while employing the DASs 18a that use the simultaneous acquisition method. In other words, when the dual-energy acquisition is performed by using the fast switching while employing the DASs 18 that use the sequential acquisition method, there are time differences in the timing of the acquisition of the signals from the detecting elements, and the allowed period is shorter by the length corresponding to the time differences.

In this situation, the imaging conditions that can be set may be limited in some situations because of the shortened allowed period. For example, the larger the voltage difference is between the first tube voltage value V1 and the second tube voltage value V2, the longer time period it takes to switch between the tube voltage values. In other words, there may be some situations where the tube voltage values that can be set are limited because of the shortened allowed period.

Further, to lower the tube voltage value, it is necessary to allow electrons to flow out of the negative pole (the filament) of the X-ray tube. However, the smaller the X-ray tube current value (hereinafter, simply "tube current value") is, the more slowly the electrons move and the longer time period it takes to lower the tube voltage value. In other words, the lower limit for the tube current value that can be set may be limited, in some situations, because of the shortened allowed period. Further, to raise the tube voltage value, it is necessary to have electrons accumulated in the negative pole of the X-ray tube. However, the larger the tube current value is, the more electrons flow out of the negative pole, and the longer time period it takes to raise the tube voltage value. In other words, the upper limit for the tube current value that can be set may be limited, in some situations, because of the shortened allowed period.

Figure 16:
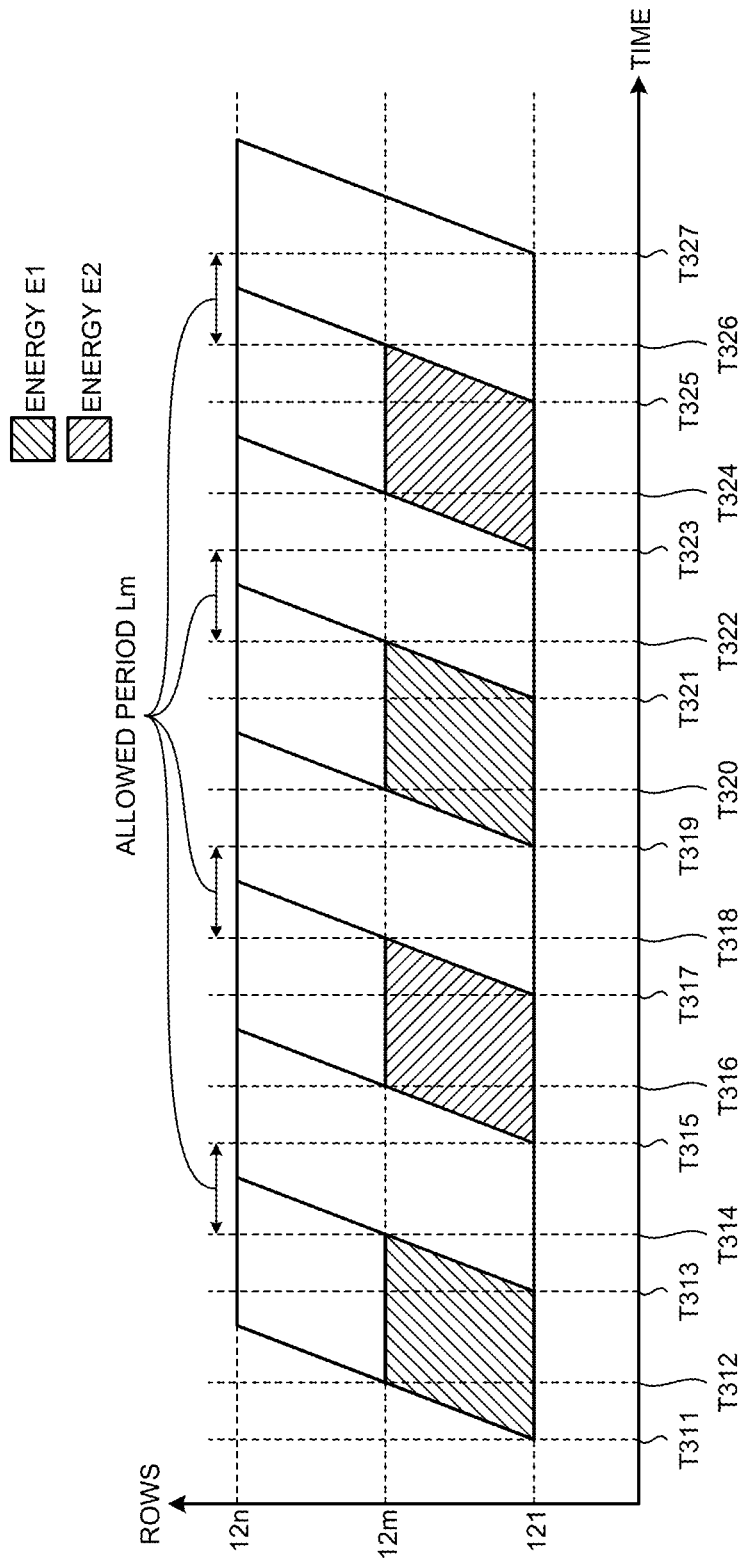
FIG. 16 is a chart illustrating an example of the dual-energy acquisition employing the DAS that uses the sequential acquisition method according to the fifth embodiment.

To cope with these situations, the adjusting function 445 is configured to control the allowed period by adjusting the number of rows in the family of detecting elements from which the DAS 18 using the sequential acquisition method acquires the signals and is further configured to enhance the degree of freedom of the imaging conditions. In the following sections, the control exercised over the allowed period by the adjusting function 445 will be explained, with reference to FIG. 16. FIG. 16 is a chart illustrating an example of the dual-energy acquisition employing the DAS 18 that uses the sequential acquisition method according to the fifth embodiment.

In the example illustrated in FIG. 16, at least in the time period from the time T311 to the time T314, the system controlling function 441 causes X-rays having the energy E1 to be generated by supplying the first tube voltage value V1 to the X-ray tube 11. Further, in the time period from the time T314 to the time T315, the system controlling function 441 switches the tube voltage value to be supplied to the X-ray tube 11 from the first tube voltage value V1 to the second tube voltage value V2.

Subsequently, at least in the time period from the time T315 to the time T318, the system controlling function 441 causes X-rays having the energy E2 to be generated by supplying the second tube voltage value V2 to the X-ray tube 11. Further, in the time period from the time T318 to the time T319, the system controlling function 441 switches the tube voltage value to be supplied to the X-ray tube 11 from the second tube voltage value V2 to the first tube voltage value V1.

After that, at least in the time period from the time T319 to the time T322, the system controlling function 441 causes X-rays having the energy E1 to be generated by supplying the first tube voltage value V1 to the X-ray tube 11. Further, in the time period from the time T322 to the time T323, the system controlling function 441 switches the tube voltage value to be supplied to the X-ray tube 11 from the first tube voltage value V1 to the second tube voltage value V2.

Subsequently, at least in the time period from the time T323 to the time T326, the system controlling function 441 causes X-rays having the energy E2 to be generated by supplying the second tube voltage value V2 to the X-ray tube 11. Further, in the time period from the time T326 to the time T327 the system controlling function 441 switches the tube voltage value to be supplied to the X-ray tube 11 from the second tube voltage value V2 to the first tube voltage value V1.

Further, as illustrated in FIG. 16, the adjusting function 445 adjusts the number of rows in the family of detecting elements from which the DAS 18 acquires the signals. In other words, the adjusting function 445 decreases the number of rows in the family of detecting elements from which the DAS 18 acquires the signals, from "n" to "m". Further, the DAS 18 sequentially acquires the signals of the X-rays from the family of detecting elements including m detecting elements.

More specifically, in the time period from the time T311 to the time T312, the DAS 18 sequentially acquires m signals from the family of detecting elements including the m detecting elements, namely the detecting elements 121 to 12m. Further, in the time period from the time T313 to the time T314, the DAS 18 sequentially acquires m signals from the family of detecting elements. After that, in the time period from the time T315 to the time T316, the DAS 18 sequentially acquires m signals from the family of detecting elements. Subsequently, in the time period from the T317 to the time T318, the DAS 18 sequentially acquires m signals from the family of detecting elements. Also, in the time period from the time T319 to the time T320, the DAS 18 sequentially acquires m signals from the family of detecting elements. After that, in the time period from the time T321 to the time T322, the DAS 18 sequentially acquires m signals from the family of detecting elements. In addition, in the time period from the time T323 to the time T324, the DAS 18 sequentially acquires m signals from the family of detecting elements. Furthermore, in the time period from the time T325 to the time T326, the DAS 18 sequentially acquires m signals from the family of detecting elements.

In FIG. 16, to ensure that the energy at the time of the generation of the X-rays detected by the detecting elements, namely the detecting elements 121 to 12m, is constant among the detecting elements, the system controlling function 441 needs to complete the switching of the tube voltage value between the first tube voltage value V1 and the second tube voltage value V2 within the allowed period. As illustrated in FIG. 16, the allowed period for sequentially acquiring the signals from the family of detecting elements including the m detecting elements may be referred to as an allowed period Lm.

More specifically, in the time period from the time T314 to the time T315, the system controlling function 441 needs to switch the tube voltage value to be supplied to the X-ray tube 11 from the first tube voltage value V1 to the second tube voltage value V2. Also, in the time period from the time T318 to the time T319, the system controlling function 441 needs to switch the tube voltage value to be supplied to the X-ray tube 11 from the second tube voltage value V2 to the first tube voltage value V1. Further, in the time period from the time T322 to the time T323, the system controlling function 441 needs to switch the tube voltage value to be supplied to the X-ray tube 11 from the first tube voltage value V1 to the second tube voltage value V2. In addition, in the time period from the time T326 to the time T327, the system controlling function 441 needs to switch the tube voltage value to be supplied to the X-ray tube 11 from the second tube voltage value V2 to the first tube voltage value V1.

In this situation, the allowed period Lm indicated in FIG. 16 is longer than the allowed period Ln indicated in FIG. 14. The reason is that, because the number of detecting elements from which the single DAS 18 sequentially acquires the signals was decreased from "n" to "m", the time differences in the timing of the acquisition of the signals from the detecting elements became smaller. More specifically, the allowed period Lm indicated in FIG. 16 is longer than the allowed period Ln indicated in FIG. 14, by the length of the time period it takes to sequentially acquire the signals from (n-m) detecting elements.

Accordingly, the smaller the value of "m" is, the longer the allowed period Lm is. In other words, by adjusting the number of rows in the family of detecting elements from which the DAS 18 acquires the signals, the adjusting function 445 is able to control the allowed period.

With reference to FIG. 16, the example was explained in which the adjusting function 445 adjusts the number of rows in the family of detecting elements to "m", whereas the DAS 18 sequentially acquires the signals of the X-rays from the m detecting elements, namely the detecting elements 121 to 12m. In other words, in the example in FIG. 16, the signals of the X-rays are sequentially acquired with respect to the m detecting elements starting with the detecting element 121 positioned closest to the DAS 18. However, possible embodiments are not limited to this example. For instance, the DAS 18 may sequentially acquire the signals of the X-rays with respect to m detecting elements starting with the detecting element 12n positioned farthest from the DAS 18.

Figure 17:
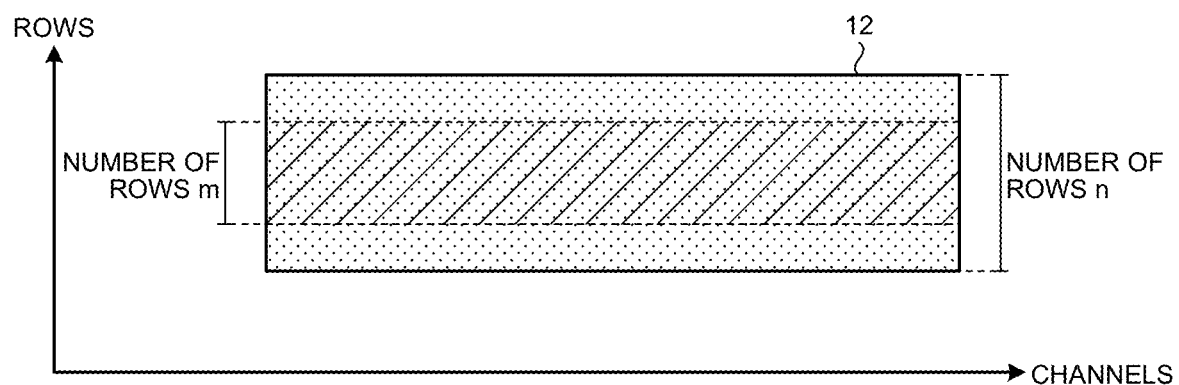
FIG. 17 is a chart for explaining adjusting the number of rows in a family of detecting elements according to the fifth embodiment.

Alternatively, for example, the DAS 18 may sequentially acquire the signals from m detecting elements positioned at the center of the X-ray detector 12. In one example, when "n" and "m" are each an even number, the DAS 18 may sequentially acquire the signals of the X-rays from m detecting elements, starting with the detecting element that is in the ((n−m)/2)-th closest position to the DAS 18 up to the detecting element that is in the ((n+m)/2)-th closest position to the DAS 18. In that situation, the plurality of DASs 18 included in the X-ray CT apparatus 1 sequentially acquire the signals of the X-rays from a central region (the region indicated with the hatching pattern in FIG. 17) corresponding to the m detecting elements, selected from the entire region (the region indicated with the dot pattern in FIG. 17) of the X-ray detector 12. In this situation, the system controlling function 441 may adjust the opening degree and the position of the collimator 17 so that the X-rays are radiated only onto such a region within the X-ray detector 12 that is indicated with the hatching pattern in FIG. 17. FIG. 17 is a chart for explaining the adjusting of the number of rows in the family of detecting elements according to the fifth embodiment.

As explained above, by adjusting the number of rows in the family of detecting elements from which the DAS 18 acquires the signals, the adjusting function 445 is able to control the allowed period for switching the tube voltage value. Further, on the basis of the allowed period resulting from the control exercised by the adjusting function 445, the setting function 446 is configured to set imaging conditions. In this situation, by controlling the allowed period, the adjusting function 445 is able to enhance the degree of freedom when the setting function 446 sets the imaging conditions.

Figure 18A:
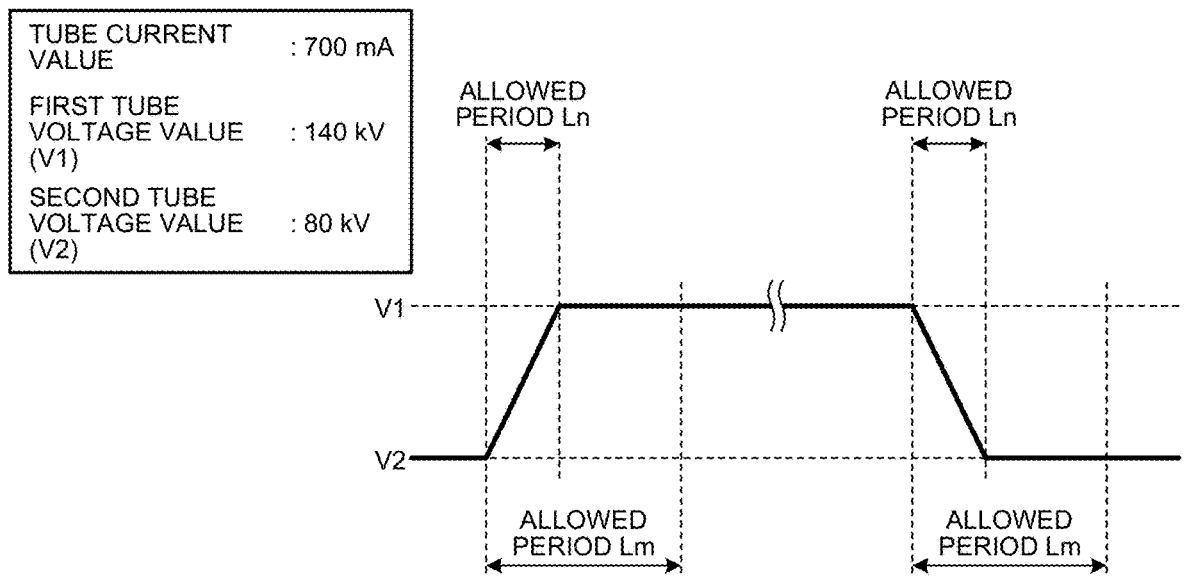
FIG. 18A is a chart for explaining a setting of an X-ray tube current value according to the fifth embodiment.
Figure 18B:
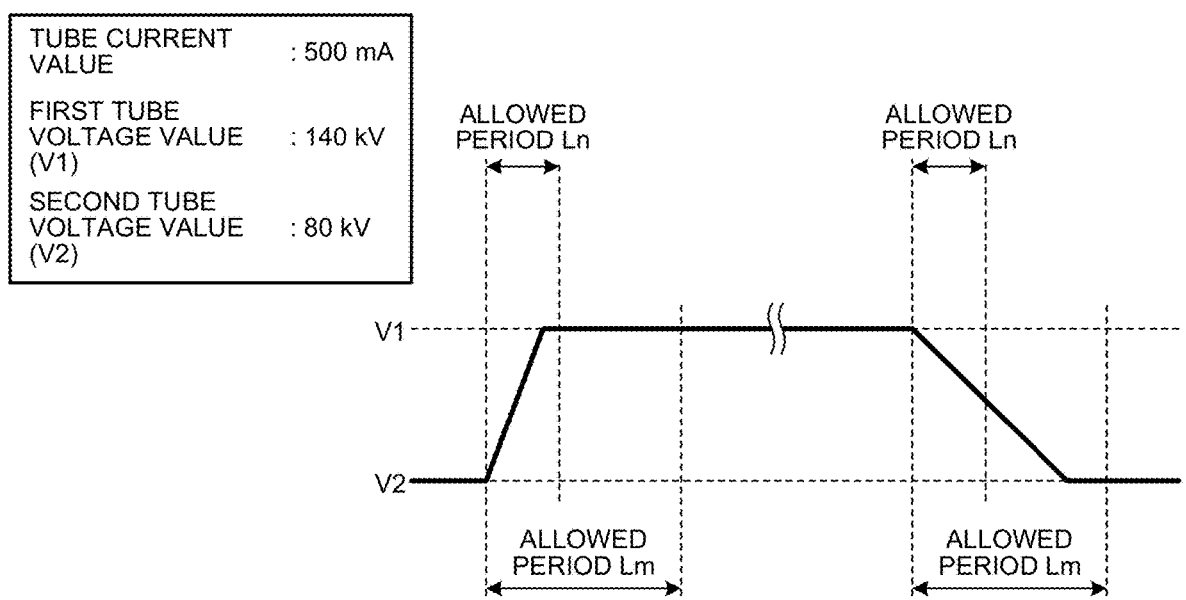
FIG. 18B is a chart for explaining another setting of an X-ray tube current value according to the fifth embodiment.
Figure 18C:
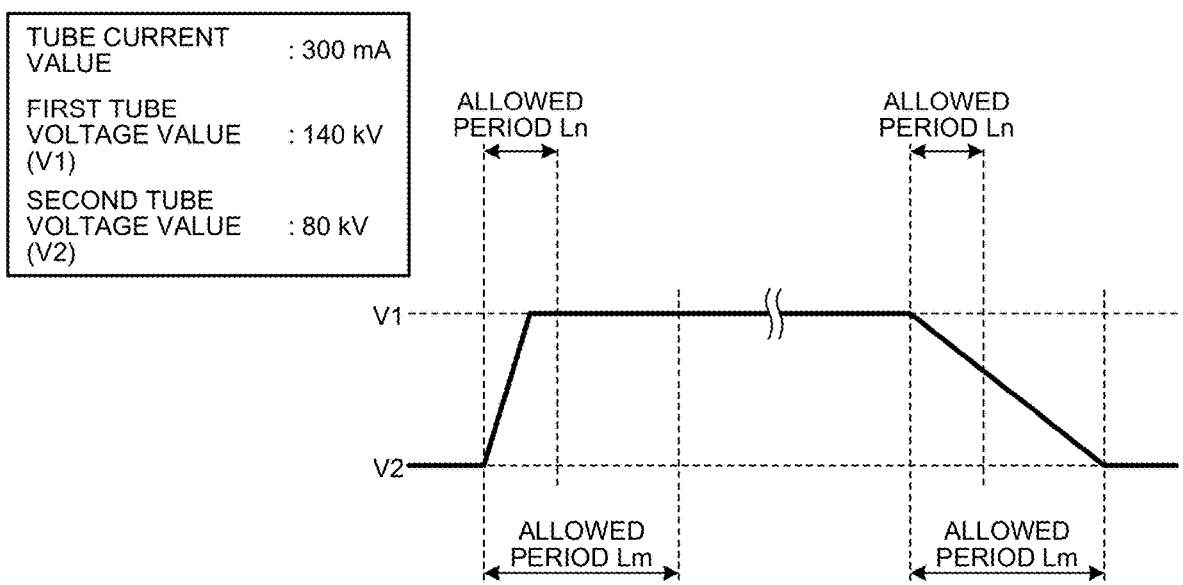
FIG. 18C is a chart for explaining yet another setting of an X-ray tube current value according to the fifth embodiment.

For example, on the basis of the allowed period resulting from the control exercised by the adjusting function 445, the setting function 446 sets the tube current value of the X-ray tube 11. In the following sections, an example of the settings of the tube current value will be explained, with reference to FIGS. 18A, 18B, and 18C. FIGS. 18A, 18B, and 18C are charts for explaining the settings of the tube current values according to the fifth embodiment. In FIGS. 18A, 18B, and 18C, the horizontal axis expresses time, whereas the vertical axis expresses tube voltage values.

First, FIG. 18A will be explained. FIG. 18A indicates the time required by raising and lowering of the tube voltage value, in the situation where the tube current value is "700 mA", while the first tube voltage value V1 is "140 kV", and the second tube voltage value V2 is "80 kV". In FIG. 18A, it is possible to raise the tube voltage value from the second tube voltage value V2 to the first tube voltage value V1 within the allowed period Ln corresponding to the number of rows in the family of detecting elements being "n". Further, in FIG. 18A, it is also possible to lower the tube voltage value from the first tube voltage value V1 to the second tube voltage value V2 within the allowed period Ln.

Further, FIG. 18B indicates the time required by raising and lowering of the tube voltage value, in the situation where the tube current value is "500 mA", while the first tube voltage value V1 is "140 kV", and the second tube voltage value V2 is "80 kV". In other words, FIG. 18B indicates the example in which the tube current value is smaller than that in FIG. 18A. Accordingly, in FIG. 18B, the time required by the raising of the tube voltage value is shorter, while the time required by the lowering of the tube voltage value is longer than those in the example in FIG. 18A.

In FIG. 18B, within the allowed period Ln corresponding to the number of rows in the family of detecting elements being "n", it is possible to raise the tube voltage value from the second tube voltage value V2 to the first tube voltage value V1. However, in FIG. 18B, it is not possible to lower the tube voltage value from the first tube voltage value V1 to the second tube voltage value V2 within the allowed period Ln.

Further, in FIG. 18B, within the allowed period Lm corresponding to the number of rows in the family of detecting element having been adjusted to "m", it is possible to raise the tube voltage value from the second tube voltage value V2 to the first tube voltage value V1. Further, in FIG. 18B, it is also possible to lower the tube voltage value from the first tube voltage value V1 to the second tube voltage value V2 within the allowed period Lm. In other words, as a result of the adjusting function 445 controlling the allowed period, the setting function 446 is able to select the tube current value "500 mA" as an imaging condition.

Further, FIG. 18C indicates the time required by raising and lowering of the tube voltage value, in the situation where the tube current value is "300 mA", while the first tube voltage value V1 is "140 kV", and the second tube voltage value V2 is "80 kV". In other words, FIG. 18C indicates the example in which the tube current value is even smaller than that in FIG. 18B. Accordingly, in FIG. 18C, the time required by the raising of the tube voltage value is even shorter, while the time required by the lowering of the tube voltage value is even longer than those in the example in FIG. 18B.

In FIG. 18C, within the allowed period Ln corresponding to the number of rows in the family of detecting elements being "n", it is possible to raise the tube voltage value from the second tube voltage value V2 to the first tube voltage value V1. However, in FIG. 18C, it is not possible to lower the tube voltage value from the first tube voltage value V1 to the second tube voltage value V2 within the allowed period Ln.

Further, in FIG. 18C, within the allowed period Lm corresponding to the number of rows in the family of detecting element having been adjusted to "m", it is possible to raise the tube voltage value from the second tube voltage value V2 to the first tube voltage value V1. Further, in FIG. 18C, it is also possible to lower the tube voltage value from the first tube voltage value V1 to the second tube voltage value V2 within the allowed period Lm. In other words, as a result of the adjusting function 445 controlling the allowed period, the setting function 446 is able to select the tube current value "300 mA" as an imaging condition.

Further, as indicated in FIG. 18C, when the tube current value is "300 mA", the time required by lowering the tube voltage value from the first tube voltage value V1 to the second tube voltage value V2 is substantially equal to the length of the allowed period Lm. In this situation, when the tube current value is further lowered from "300 mA", the time required by the lowering of the tube voltage value will be even longer. Accordingly, if the tube current value were further lowered from "300 mA", it would be impossible to lower the tube voltage value from the first tube voltage value V1 to the second tube voltage value V2 within the allowed period Lm.

To cope with this situation, the setting function 446 sets a value equal to or larger than "300 mA" as the tube current value. In other words, on the basis of the allowed period resulting from the control exercised by the adjusting function 445, the setting function 446 sets a lower limit for selectable tube current values and sets the tube current value of the X-ray tube 11 so as to exceed the set lower limit.

In this situation, the setting function 446 may set a new tube current value of the X-ray tube 11 or may set the tube current value by changing a pre-set condition that was set in advance. For example, when setting the new tube current value, the setting function 446 causes the display 42 to display the lower limit for the selectable tube current values and further receives an operation to input a tube current value from the operator. After that, when the operator has input the value exceeding the lower limit, the setting function 446 sets the input value as the tube current value of the X-ray tube 11.

Alternatively, for example, when setting the tube current value by changing the pre-set condition, the setting function 446 causes the display 42 to display the pre-set condition and further receives an operation to change the pre-set condition from the operator. In this situation, the setting function 446 receives the operation to change the pre-set condition in such a range that exceeds the lower limit for the selectable tube current values. Further, the setting function 446 sets the pre-set condition changed by the operator as the tube current value of the X-ray tube 11.

Similarly, when the tube current value becomes larger, the time required by the raising of the tube voltage value becomes longer. Accordingly, there is a possibility that it may be impossible to raise the tube voltage value from the second tube voltage value V2 to the first tube voltage value V1 within the allowed period Lm corresponding to the number of rows in the family of detecting elements having been adjusted to "m". To cope with this situation, on the basis of the allowed period resulting from the control exercised by the adjusting function 445, the setting function 446 may set an upper limit for selectable tube current values so as to set the tube current value of the X-ray tube 11 to be smaller than the set upper limit.

Figure 19A:
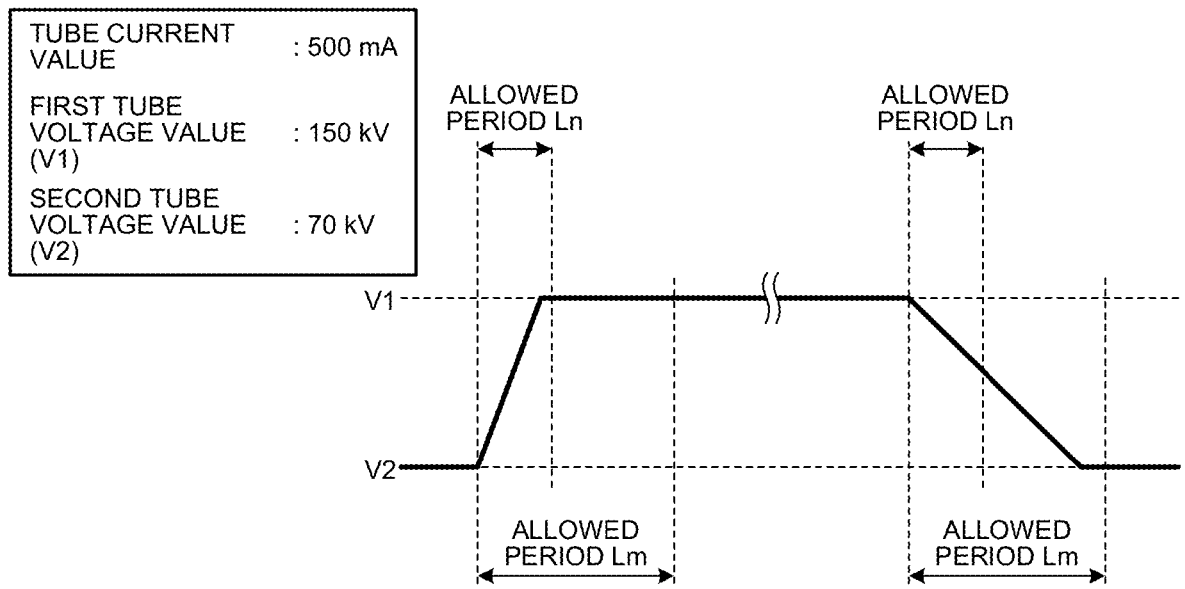
FIG. 19A is a chart for explaining a setting of an X-ray tube voltage value according to the fifth embodiment.
Figure 19B:
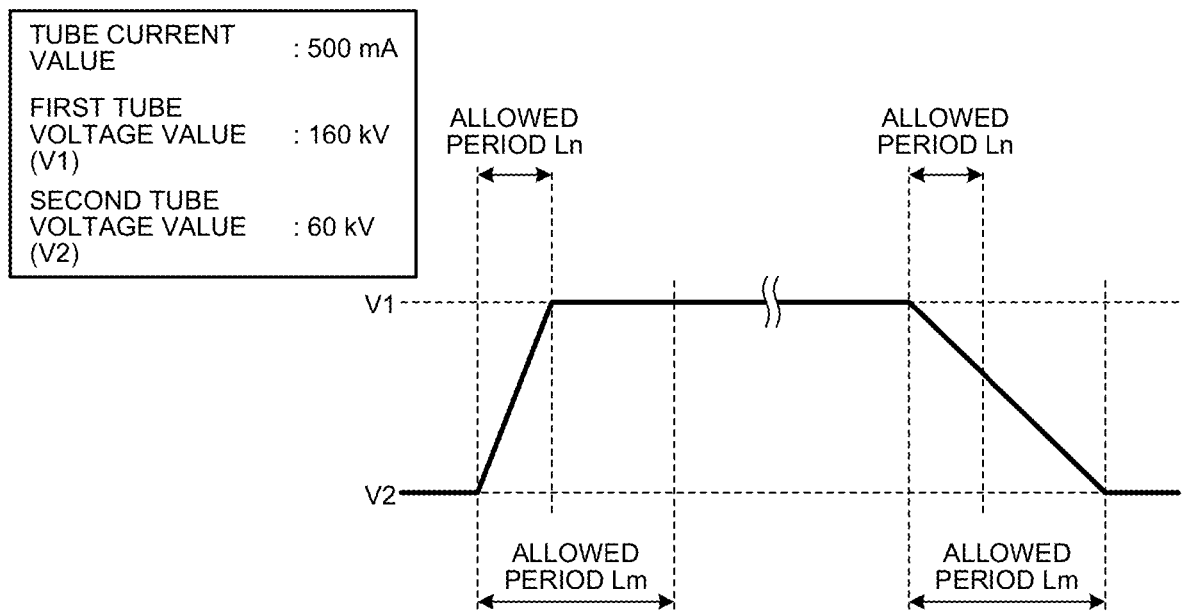
FIG. 19B is a chart for explaining another setting of an X-ray tube voltage value according to the fifth embodiment.

Next, an example in which the tube voltage value to be supplied to the X-ray tube 11 is set as an imaging condition will be explained with reference to FIGS. 19A and 19B. FIGS. 19A and 19B are charts for explaining settings of tube voltage values according to the fifth embodiment. In FIGS. 19A and 19B, the horizontal axis expresses time, whereas the vertical axis expresses tube voltage values.

First, FIG. 19A will be explained. FIG. 19A indicates the time required by raising and lowering of the tube voltage value, in the situation where the tube current value is "500 mA", while the first tube voltage value V1 is "150 kV", and the second tube voltage value V2 is "70 kV". In other words, FIG. 19A indicates the example in which the first tube voltage value V1 is larger while the second tube voltage value V2 is smaller than those in FIG. 18B.

In other words, FIG. 19A indicates the example in which the voltage difference between the first tube voltage value V1 and the second tube voltage value V2 is larger than that in FIG. 18B. More specifically, the voltage difference between the first tube voltage value V1 and the second tube voltage value V2 in FIG. 18B is "60 kV", whereas the voltage difference between the first tube voltage value V1 and the second tube voltage value V2 in FIG. 19A is "80 kV". Accordingly, in FIG. 19A, the time required by the raising of the tube voltage value and the time required by the lowering of the tube voltage value are both longer than those in FIG. 18B.

In FIG. 19A, within the allowed period Ln corresponding to the number of rows in the family of detecting elements being "n", it is possible to raise the tube voltage value from the second tube voltage value V2 to the first tube voltage value V1. However, in FIG. 19A, it is not possible to lower the tube voltage value from the first tube voltage value V1 to the second tube voltage value V2 within the allowed period Ln.

Further, in FIG. 19A, within the allowed period Lm corresponding to the number of rows in the family of detecting element having been adjusted to "m", it is possible to raise the tube voltage value from the second tube voltage value V2 to the first tube voltage value V1. Further, in FIG. 19A, it is also possible to lower the tube voltage value from the first tube voltage value V1 to the second tube voltage value V2 within the allowed period Lm. In other words, as a result of the adjusting function 445 controlling the allowed period, the setting function 446 is able to select "150 kV" as the first tube voltage value and to select "70 kV" as the second tube voltage value. In other words, as a result of the adjusting function 445 controlling the allowed period, the setting function 446 is able to select the set made up of "150 kV" and "70 kV" as the tube voltage values to be supplied to the X-ray tube 11.

Further, FIG. 19B indicates the time required by raising and lowering of the tube voltage value, in the situation where the tube current value is "500 mA", while the first tube voltage value V1 is "160 kV", and the second tube voltage value V2 is "60 kV". In other words, FIG. 19B indicates the example in which the first tube voltage value V1 is even larger while the second tube voltage value V2 is even smaller than those in FIG. 19A.

In other words, FIG. 19B indicates the example in which the voltage difference between the first tube voltage value V1 and the second tube voltage value V2 is even larger than that in FIG. 19A. More specifically, the voltage difference between the first tube voltage value V1 and the second tube voltage value V2 in FIG. 19B is "100 kV". Accordingly, in FIG. 19B, the time required by the raising of the tube voltage value and the time required by the lowering of the tube voltage value are both longer than those in FIG. 19A.

In FIG. 19B, within the allowed period Ln corresponding to the number of rows in the family of detecting elements being "n", it is possible to raise the tube voltage value from the second tube voltage value V2 to the first tube voltage value V1. However, in FIG. 19B, it is not possible to lower the tube voltage value from the first tube voltage value V1 to the second tube voltage value V2 within the allowed period Ln.

Further, in FIG. 19B, within the allowed period Lm corresponding to the number of rows in the family of detecting element having been adjusted to "m", it is possible to raise the tube voltage value from the second tube voltage value V2 to the first tube voltage value V1. Further, in FIG. 19B, it is also possible to lower the tube voltage value from the first tube voltage value V1 to the second tube voltage value V2 within the allowed period Lm. In other words, as a result of the adjusting function 445 controlling the allowed period, the setting function 446 is able to select "160 kV" as the first tube voltage value and to select "60 kV" as the second tube voltage value. In other words, as a result of the adjusting function 445 controlling the allowed period, the setting function 446 is able to select the set made up of "160 kV" and "60 kV" as the tube voltage values to be supplied to the X-ray tube 11.

Further, as indicated in FIG. 19B, when the first tube voltage value is "160 kV", while the second tube voltage value is "60 kV", the time required by lowering the tube voltage value from the first tube voltage value V1 to the second tube voltage value V2 is substantially equal to the length of the allowed period Lm. In this situation, when the voltage difference between the first tube voltage value V1 and the second tube voltage value V2 is further increased from "100 kV", the time required by the lowering of the tube voltage value will be even longer. Accordingly, if the voltage difference between the first tube voltage value V1 and the second tube voltage value V2 were further increased from "100 kV", it would be impossible to lower the tube voltage value from the first tube voltage value V1 to the second tube voltage value V2 within the allowed period Lm.

To cope with this situation, the setting function 446 sets the tube voltage value in such a range that the voltage difference between the first tube voltage value V1 and the second tube voltage value V2 does not exceed "100 kV". In other words, on the basis of the allowed period resulting from the control exercised by the adjusting function 445, the setting function 446 sets an upper limit for the voltage difference between the first tube voltage value V1 and the second tube voltage value V2 and further sets the first tube voltage value V1 and the second tube voltage value V2 so as not to exceed the set upper limit.

In this situation, the setting function 446 may set a new tube voltage value or may set the tube voltage value by changing a pre-set condition that was set in advance. For example, when setting the new tube voltage value, the setting function 446 causes the display 42 to display the upper limit for selectable voltage differences and further receives an operation to input a first tube voltage value V1 and a second tube voltage value V2 from the operator. After that, when the voltage difference between the first tube voltage value V1 and the second tube voltage value V2 having been input is smaller than the upper limit, the setting function 446 sets the input values as the tube voltage values to be supplied to the X-ray tube 11.

Alternatively, for example, when setting the tube voltage value by changing the pre-set condition, the setting function 446 causes the display 42 to display the pre-set condition and further receives an operation to change the pre-set condition from the operator. In this situation, the setting function 446 receives the operation to change the pre-set condition in such a range that does not to exceed the upper limit for the selectable voltage value differences. Further, the setting function 446 sets the pre-set condition changed by the operator as the tube voltage value of the X-ray tube 11.

Not only the voltage difference between the first tube voltage value V1 and the second tube voltage value V2, but also the magnitudes of the first tube voltage value V1 and the second tube voltage value V2 may affect the time required by the lowering of the tube voltage value. In one example, when the first tube voltage value V1 is "160 kV", and the second tube voltage value V2 is "60 kV" as indicated in FIG. 19B, the time required by lowering the tube voltage value from the first tube voltage value V1 to the second tube voltage value V2 is substantially equal to the length of the allowed period Lm. In this situation, for example, when the first tube voltage value V1 is "150 kV", and the second tube voltage value V2 is "50 kV", although the voltage difference between the first tube voltage value V1 and the second tube voltage value V2 remains to be "100 kV", because the magnitudes of the first tube voltage value V1 and the second tube voltage value V2 are smaller, the time required by the lowering of the tube voltage value will be longer.

Accordingly, when the first tube voltage value V1 is "150 kV", and the second tube voltage value V2 is "50 kV", there is a possibility that it may not be possible to lower the tube voltage value from the first tube voltage value V1 to the second tube voltage value V2 within the allowed period Lm.

To cope with this situation, the setting function 446 may be configured to set the tube voltage value to be supplied to the X-ray tube 11 on the basis of not only the voltage difference between the first tube voltage value V1 and the second tube voltage value V2, but also the magnitudes of the first tube voltage value V1 and the second tube voltage value V2. For example, the setting function 446 obtains, in advance, a table defining the time required by lowering the tube voltage value from the first tube voltage value V1 to the second tube voltage value V2 for each set made up of a first tube voltage value V1 and a second tube voltage value V2 and stores the obtained table into the memory 41. Further, on the basis of the allowed period resulting from the control exercised by the adjusting function 445 and the table stored in the memory 41, the setting function 446 sets the first tube voltage value V1 and the second tube voltage value V2 that make it possible to lower the tube voltage value from the first tube voltage value V1 to the second tube voltage value V2 within the allowed period.

After the imaging conditions have been set by the setting function 446, the system controlling function 441 performs an imaging process according to the set imaging conditions. For example, the system controlling function 441 causes X-rays to be generated by supplying high voltage to the X-ray tube 11 according to the set imaging conditions. In this situation, the system controlling function 441 changes the energy of the X-rays for each view, by switching the tube voltage value to be supplied to the X-ray tube 11 between the first tube voltage value V1 and the second tube voltage value V2. Further, by controlling the bed driving device 32, the system controlling function 441 moves the patient P to the inside of the opening of the gantry 10. Further, the system controlling function 441 adjusts the opening degree and the position of the collimator 17. Also, the system controlling function 441 rotates the rotating part by controlling the controlling device 15.

In this situation, the detecting elements included in the X-ray detector 12 are configured to detect the X-rays that have passed through the patient P.

Further, the plurality of DASs 18 included in the X-ray CT apparatus 1 are each configured to sequentially acquire the signals of the X-rays in correspondence with each family of detecting elements. For example, each of the plurality of DASs 18 is configured to sequentially acquire the signals of the X-rays from the family of detecting elements including the detecting elements of which the number of rows has been adjusted by the adjusting function 445.

For example, when the adjusting function 445 has adjusted the number of rows to "n", each of the DASs 18 sequentially acquires the signals of the X-rays from a family of detecting elements including the n detecting elements, namely the detecting elements 121 to 12n. In other words, when the number of rows is adjusted to "n", the plurality of DASs 18 included in the X-ray CT apparatus 1 are configured to sequentially acquire the signals of the X-rays from the entire region (e.g., the region indicated with the dot pattern in FIG. 17) of the X-ray detector 12.

Further, for example, when the adjusting function 445 has adjusted the number of rows to "m", each of the DASs 18 is configured to sequentially acquire the signals of the X-rays from a family of detecting elements including m detecting elements, namely the detecting elements 121 to 12m. In other words, when the number of rows has been adjusted to "m", the plurality of DASs 18 included in the X-ray CT apparatus 1 are configured to sequentially acquire the signals of the X-rays from a partial region (e.g., the region indicated with the hatching pattern in FIG. 17) of the X-ray detector 12.

Further, the pre-processing function 442 is configured to perform a pre-processing process on the detection data output from the DASs 18. Further, the generating function 443 is configured to generate CT image data on the basis of the projection data on which the pre-processing process has been performed and to also perform the process (hereinafter "discriminating process") of discriminating the types, the atomic numbers, the density levels, and the like of the substances included in the patient P, by using the notion that different substances have different X-ray absorption characteristics. Alternatively, the discriminating process may be performed by an external apparatus. For example, the output function 444 may output the projection data (either the detection data before the pre-processing process is performed or the raw data after the pre-processing process is performed) to the external apparatus connected to the X-ray CT apparatus 1 via a network so that the external apparatus performs the discriminating process. Further, the output function 444 is configured to output the CT image data generated by the generating function 443 and results of the discriminating process. For example, the output function 444 causes the display 42 to display a display-purpose CT image based on the CT image data or an image indicating the results of the discriminating process over a CT image. Further, for example, the output function 444 is configured to output various types of data such as the CT image data to an external apparatus.

The examples were explained above in which the DAS 18 is connected to the n detecting elements (the detecting elements 121 to 12n) arranged along the row direction of the X-ray detector 12; however, possible embodiments are not limited to these examples. For instance, when detecting elements (detecting elements 221 to 22j) of which the quantity is equal to j are arranged along the channel direction of the X-ray detector 12, the DAS 18 may be connected to the j detecting elements, namely the detecting elements 221 to 22j. In that situation, the X-ray CT apparatus 1 includes DASs 18 of which the quantity is equal to the number of rows in the X-ray detector 12, for example. Further, in that situation, the adjusting function 445 is configured, for example, to adjust the number of channels in the family of detecting elements from which the DASs 18 acquire the signals.

Figure 20:
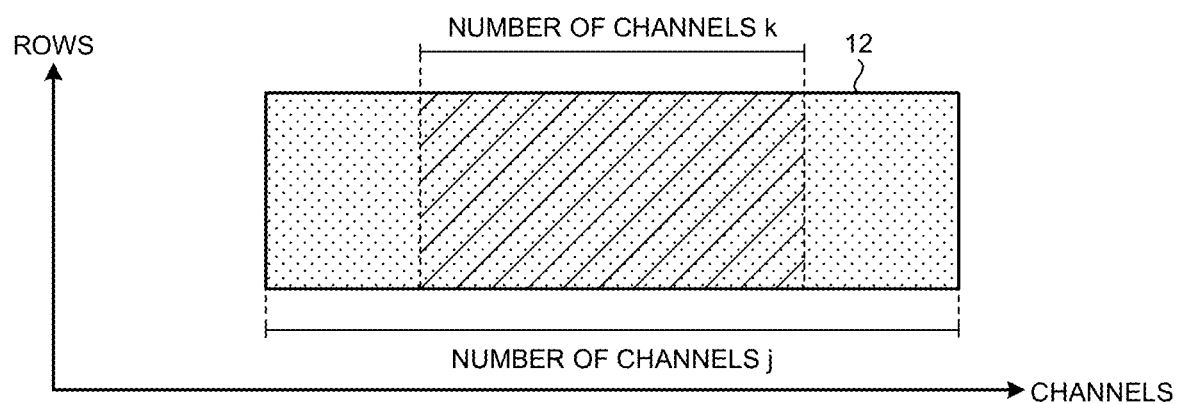
FIG. 20 is a chart for explaining adjusting the number of channels in a family of detecting elements according to the fifth embodiment.

For example, when the adjusting function 445 has adjusted the number of channels to "j", each of the DASs 18 is configured to sequentially acquire the signals of the X-rays from the family of detecting elements including the j detecting elements, namely, the detecting elements 22a to 22j. In other words, when the number of rows has been adjusted to "j", the plurality of DASs 18 included in the X-ray CT apparatus 1 are configured to sequentially acquire the signals of the X-rays from the entire region (e.g., the region indicated with the dot pattern in FIG. 20) of the X-ray detector 12. FIG. 20 is a chart for explaining the adjusting of the number of channels in the family of detecting elements according to the fifth embodiment.

Further, for example, when the number of channels has been adjusted to "k", which is smaller than "j", each of the DASs 18 is configured to sequentially acquire the signals of the X-rays from a family of detecting elements including k detecting elements. In other words, when the number of rows has been adjusted to "k", the plurality of DASs 18 included in the X-ray CT apparatus 1 are configured to sequentially acquire the signals of the X-rays from a partial region (e.g., the region indicated with the hatching pattern in FIG. 20) of the X-ray detector 12.

The examples were explained above in which each of the DASs 18 is configured to sequentially acquire the signals of the X-rays from the detecting elements in one row of the X-ray detector 12 and in which each of the DASs 18 is configured to sequentially acquire the signals of the X-rays from the detecting elements in one channel of the X-ray detector 12; however, possible embodiments are not limited to these examples. For instance, each of the DASs 18 may be configured to sequentially acquire the signals of the X-rays from detecting elements in two or more rows of the X-ray detector 12. In another example, each of the DASs 18 may be configured to sequentially acquire the signals of the X-rays from detecting elements in two or more channels of the X-ray detector 12. Alternatively, a single DAS 18 may be configured to sequentially acquire the signals of the X-rays from all of the detecting elements in the X-ray detector 12. Also, in that situation, the adjusting function 445 may be configured to adjust both the number of rows and the number of channels in the family of detecting elements from which the DAS 18 acquires the signals.

Further, the examples were explained above in which the energy of the X-rays is changed for each view; however, possible embodiments are not limited to these examples. In other words, the system controlling function 441 may be configured to change the energy of X-rays for every two or more views.

Figure 21:
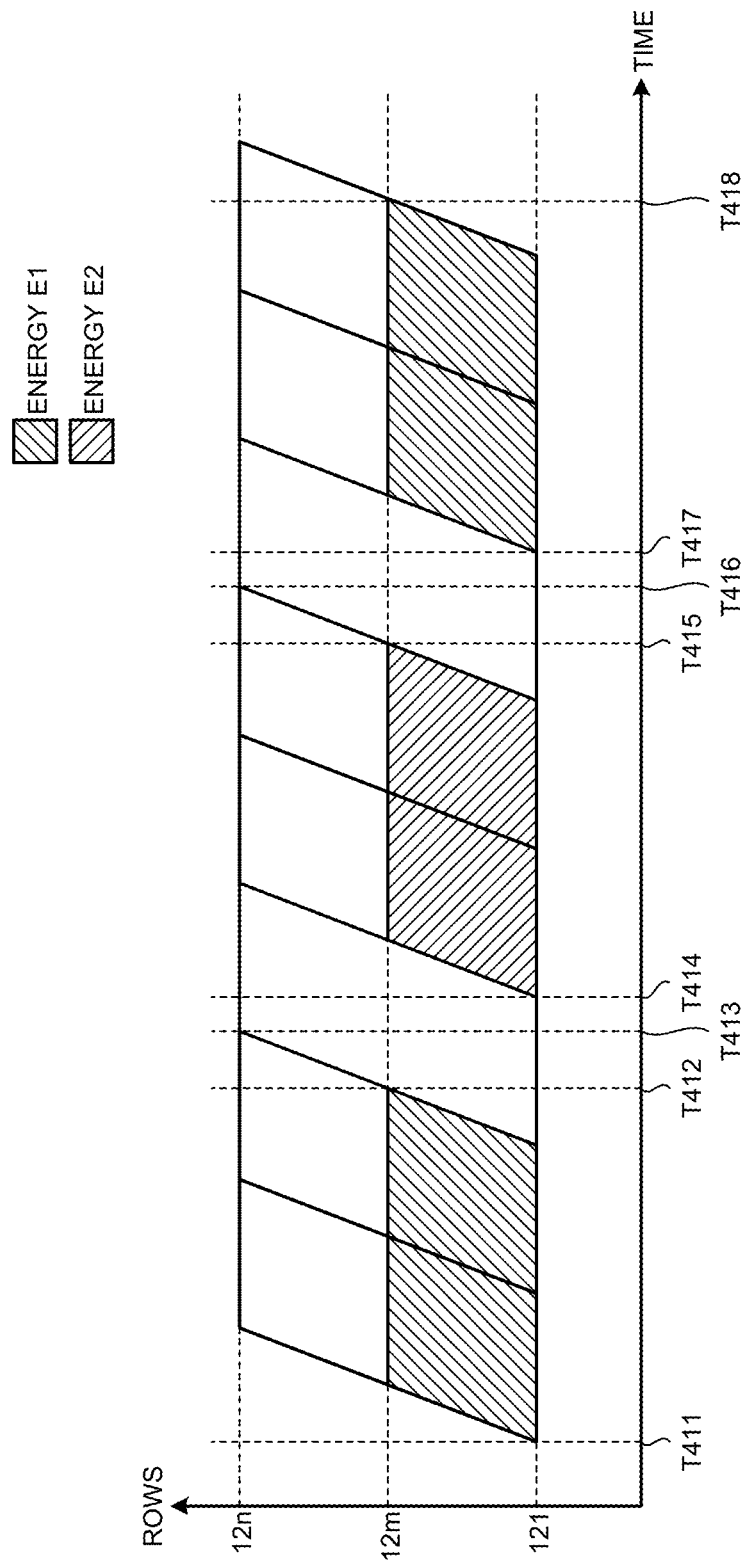
FIG. 21 is a chart illustrating another example of the dual-energy acquisition employing a DAS that uses the sequential acquisition method according to the fifth embodiment.

For example, as illustrated in FIG. 21, the system controlling function 441 may be configured to change the energy of the X-rays for every two or more views. More specifically, at least in the time period from the time T411 to the time T412, the system controlling function 441 causes X-rays having the energy E1 to be generated, by supplying the first tube voltage value V1 to the X-ray tube 11. In other words, the system controlling function 441 causes the X-rays having the energy E1 to be generated over the two views. FIG. 21 is a chart illustrating another example of the dual-energy acquisition employing a DAS 18 that uses the sequential acquisition method according to the fifth embodiment.

Subsequently, the system controlling function 441 switches the tube voltage value to be supplied to the X-ray tube 11 from the first tube voltage value V1 to the second tube voltage value V2. In this situation, when the number of rows in the family of detecting elements from which the DAS 18 acquires the signals is "n", the allowed period for switching the tube voltage value to be supplied to the X-ray tube 11 is the time period from the time T413 to the time T414. In contrast, when the adjusting function 445 has adjusted the number of rows in the family of detecting elements to "m", the allowed period for switching the tube voltage value to be supplied to the X-ray tube 11 is the time period from the time T412 to the time T414.

After that, at least in the time period from the time T414 to the time T415, the system controlling function 441 causes X-rays having the energy E2 to be generated by supplying the second tube voltage value V2 to the X-ray tube 11. Subsequently, the system controlling function 441 switches the tube voltage value to be supplied to the X-ray tube 11 from the second tube voltage value V2 to the first tube voltage value V1. In this situation, when the number of rows in the family of detecting elements from which the DAS 18 acquires the signals is "n", the allowed period for switching the tube voltage value to be supplied to the X-ray tube 11 is the time period from the time T416 to the time T417. In contrast, when the adjusting function 445 has adjusted the number of rows in the family of detecting elements to "m", the allowed period for switching the tube voltage value to be supplied to the X-ray tube 11 is the time period from the time T415 to the time T417. After that, at least in the time period from the time T417 to the time T418, the system controlling function 441 causes X-rays having the energy E1 to be generated, by supplying the first tube voltage value V1 to the X-ray tube 11.

As illustrated in FIG. 21, by decreasing the number of rows in the family of detecting elements from which the DAS 18 acquires the signals from "n" to "m", the adjusting function 445 prolongs the allowed period for switching the first tube voltage value V1 to the second tube voltage value V2, from "the time period from the time T413 to the time T414" to "the time period from the time T412 to the time T414". Further, by decreasing the number of rows from "n" to "m", the adjusting function 445 prolongs the allowed period for switching the second tube voltage value V2 to the first tube voltage value V1, from "the time period from the time T416 to the time T417" to "the time period from the time T415 to the time T417". In other words, even in the situation where the system controlling function 441 changes the energy of the X-rays for every two or more views, the adjusting function 445 is able to control the allowed period for switching the tube voltage value to be supplied to the X-ray tube 11, by adjusting the number of rows in the family of detecting elements from which the DAS 18 acquires the signals.

Further, the examples were explained above in which, as illustrated in FIGS. 17 and 20, one or both of the number of rows and the number of channels in the family of detecting elements from which the DAS 18 acquires the signals are adjusted by changing, within the X-ray detector 12, the region from which the signals of the X-rays are to be acquired; however, possible embodiments are not limited to these examples. For instance, the adjusting function 445 may be configured to adjust one or both of the number of rows and the number of channels in the family of detecting elements from which the DAS 18 acquires the signals, by adjusting a bundling condition used when the DAS 18 acquires the signals.

In one example, when the DAS 18 is connected to the n detecting elements (the detecting elements 12₁ to 12n) arranged along the row direction of the X-ray detector 12, the adjusting function 445 adjusts the bundling condition so that the signals are acquired as being bundled for each set made up of two detecting elements positioned adjacent to each other in the row direction. With this arrangement, the adjusting function 445 is able to decrease the number of rows in the family of detecting elements from which the DAS 18 acquires the signals, substantially down to "n/2".

Figure 22:
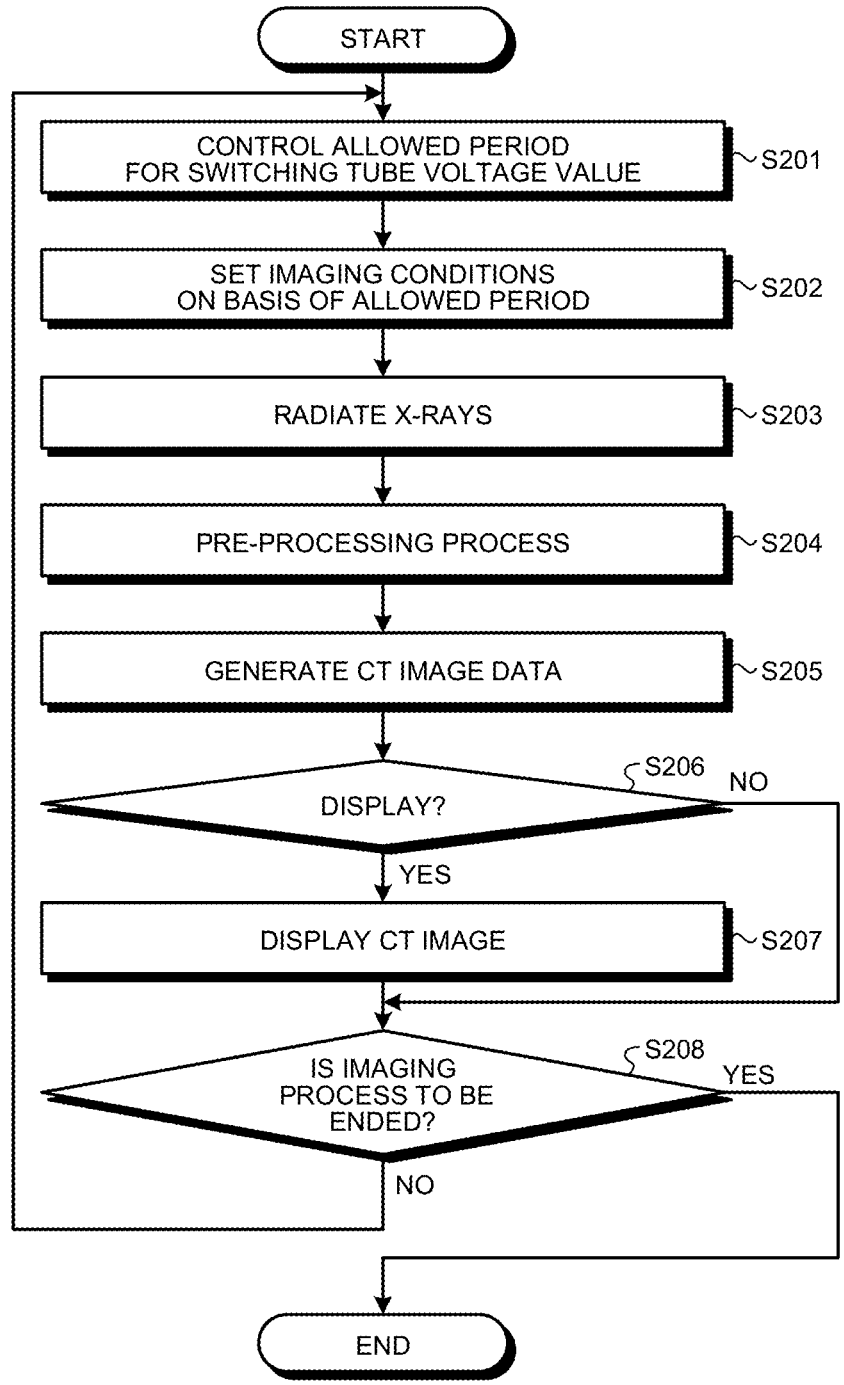
FIG. 22 is a flowchart for explaining a flow in a series of processes performed by the X-ray CT apparatus according to the fifth embodiment.

Next, an example of a procedure in processes performed by the X-ray CT apparatus 1 will be explained with reference to FIG. 22. FIG. 22 is a flowchart for explaining the flow in the series of processes performed by the X-ray CT apparatus 1 according to the fifth embodiment.

Step S201 is a step corresponding to the adjusting function 445. Step S202 is a step corresponding to the setting function 446. Steps S203 and S208 are steps corresponding to the system controlling function 441. Step S204 is a step corresponding to the pre-processing function 442. Step S205 is a step corresponding to the generating function 443. Steps S206 and S207 are steps corresponding to the output function 444.

First, the processing circuitry 44 controls the allowed period for switching the tube voltage value to be supplied to the X-ray tube 11, by adjusting one or both of the number of rows and the number of channels in the family of detecting elements from which the DAS 18 acquires the signals (step S201). Subsequently, on the basis of the allowed period resulting from the control, the processing circuitry 44 sets imaging conditions such as a tube current value, a tube voltage value, and the like (step S202).

After that, the processing circuitry 44 causes X-rays to be generated from the X-ray tube 11 according to the imaging conditions set at step S202 and causes the generated X-rays to be radiated onto the patient P (step S203). In that situation, the processing circuitry 44 changes the energy of the X-rays for every one or more views, by switching the tube voltage value to be supplied to the X-ray tube 11. Further, the DAS 18 generates detection data by sequentially acquiring the signals of the X-rays in correspondence with each family of detecting elements of which one or both of the number of rows and the number of channels were adjusted at step S201. Further, the processing circuitry 44 performs a pre-processing process on the detection data output from the DAS 18 (step S204). Further, the processing circuitry 44 generates CT image data on the basis of data (raw data) resulting from the pre-processing process (step S205).

In this situation, the processing circuitry 44 judges whether or not a CT image is to be displayed (step S206). When a CT image is to be displayed because, for example, a display instruction is received from the operator (step S206: Yes), the processing circuitry 44 generates a display-purpose CT image on the basis of the CT image data and causes the display 42 to display the generated CT image (step S207). On the contrary, when a CT image is not to be displayed (step S206: No), or after step S207 is performed, the processing circuitry 44 judges whether or not the imaging process is to be ended (step S208). When the imaging process is not to be ended because, for example, there is an additional imaging process to be performed (step S208: No), the processing circuitry 44 returns to step S201. On the contrary, when it is determined that the imaging process is to be ended (step S208: Yes), the processing circuitry 44 ends the process.

As explained above, according to the fifth embodiment, the X-ray tube 11 is configured to generate the X-rays. Further, the system controlling function 441 is configured to change the energy of the X-rays generated by the X-ray tube 11 for every one or more views, by switching the tube voltage value to be supplied to the X-ray tube 11. Further, the X-ray detector 12 includes the plurality of detecting elements configured to detect the X-rays that have passed through the patient P. Further, the DAS 18 is configured to sequentially acquire the signals of the X-rays, in correspondence with each family of detecting elements included in the X-ray detector 12. Further, the adjusting function 445 is configured to control the allowed period for switching the tube voltage value to be supplied to the X-ray tube 11, by adjusting one or both of the number of rows and the number of channels in the family of detecting elements from which the DAS 18 acquires the signals. Consequently, the X-ray CT apparatus 1 according to the fifth embodiment is able to enhance the degree of freedom of the imaging conditions, when performing the dual-energy acquisition by using the fast switching, while employing the DAS 18 that uses the sequential acquisition method.

Further, as explained above, according to the fifth embodiment, the setting function 446 is configured to set the tube current value of the X-ray tube 11, on the basis of the allowed period resulting from the control exercised by the adjusting function 445. For example, on the basis of the allowed period prolonged by the adjusting function 445, the setting function 446 sets a smaller tube current value. As a result, the X-ray CT apparatus 1 according to the fifth embodiment is able to make it possible to perform the imaging process under conditions that involve a smaller radiation dose. Further, for example, on the basis of the allowed period prolonged by the adjusting function 445, the setting function 446 sets a larger tube current value. Accordingly, the X-ray CT apparatus 1 according to the fifth embodiment is able to make it possible to perform the imaging process under conditions that yield higher image quality.

Further, as explained above, according to the fifth embodiment, the setting function 446 is configured to set the tube voltage value to be supplied to the X-ray tube 11, on the basis of the allowed period resulting from the control exercised by the adjusting function 445. For example, the setting function 446 sets a pair made up of a first tube voltage value and a second tube voltage value having a larger voltage difference, on the basis of the allowed period prolonged by the adjusting function 445. Consequently, the X-ray CT apparatus 1 according to the fifth embodiment is able to enhance the analysis capability of the discriminating process, by performing the dual-energy acquisition under the conditions involving the larger energy difference.

Further, by decreasing the number of rows in the family of detecting elements from which the DAS 18 acquires the signals, the adjusting function 445 is able to enhance the image quality of the CT image data reconstructed by the generating function 443. In other words, when the number of rows in the family of detecting elements is smaller, because the system controlling function 441 is able to perform the imaging process by using X-rays having a smaller cone angle, the image quality of the reconstructed CT image data is enhanced.

In the fifth embodiment above, the example is explained in which the imaging conditions are set on the basis of the allowed period resulting from the control exercised by the adjusting function 445. In contrast, as a sixth embodiment, an example will be explained in which the allowed period is controlled on the basis of imaging conditions set by the setting function 446.

The X-ray CT apparatus 1 according to the sixth embodiment has a configuration similar to that of the X-ray CT apparatus 1 illustrated in FIG. 12, while a part of the processes performed by the system controlling function 441 is different. In the following sections, some of the constituent elements having the same configurations as those explained in the fifth embodiment will be referred to by using the same reference characters as in FIG. 12, and the explanations thereof will be omitted.

At first, the setting function 446 sets imaging conditions such as a tube current value, a tube voltage value, and the like. For example, the setting function 446 sets the imaging conditions, by receiving an operation to input the imaging conditions from the operator via the input interface 43. Alternatively, for example, the setting function 446 may automatically set the imaging conditions, on the basis of position determining image data acquired in a position determining imaging process. In yet another example, the setting function 446 may set pre-set conditions that were set in advance, as the imaging conditions.

For example, when information from a dual-energy acquisition is important, the setting function 446 sets a pair made up of a first tube voltage value and a second tube voltage value having a large voltage difference. In another example, when it is desired that the radiation dose for the patient P be reduced, the setting function 446 sets a small tube current value. In yet another example, when it is desired that CT image data having high image quality be acquired, the setting function 446 sets a large tube current value.

Subsequently, on the basis of the imaging conditions set by the setting function 446, the adjusting function 445 controls the allowed period for switching the tube voltage value, by adjusting one or both of the number of rows and the number of channels in the family of detecting elements from which the DAS 18 acquires the signals of the X-rays. In the present embodiment, an example will be explained in which each of a plurality of DASs 18 is connected to the n detecting elements (the detecting elements 121 to 12n) arranged along the row direction of the X-ray detector 12.

For example, the setting function 446 sets, as a set of imaging conditions, a tube current value of "700 mA", a first tube voltage value V1 of "140 kV", and a second tube voltage value V2 of "80 kV". In that situation, as illustrated in FIG. 18A, it is possible to raise the tube voltage value from the second tube voltage value V2 to the first tube voltage value V1 within the allowed period Ln corresponding to the number of rows in the family of detecting elements from which the DAS 18 acquires the signals of the X-rays being "n". Further, as illustrated in FIG. 18A, it is also possible to lower the tube voltage value from the first tube voltage value V1 to the second tube voltage value V2 within the allowed period Ln. Accordingly, in this situation, the adjusting function 445 adjusts the number of rows in the family of detecting elements from which the DAS 18 acquires the signals of the X-rays to "n".

Further, for example, the setting function 446 sets, as another set of imaging conditions, a tube current value of "500 mA", a first tube voltage value V1 of "140 kV", and a second tube voltage value V2 of "80 kV". In that situation, as illustrated in FIG. 18B, it is possible to raise the tube voltage value from the second tube voltage value V2 to the first tube voltage value V1, within the allowed period Ln corresponding to the number of rows in the family of detecting elements from which the DAS 18 acquires the signals of the X-rays being "n".

However, as illustrated in FIG. 18B, when the tube current value is "500 mA", it is not possible to lower the tube voltage value from the first tube voltage value V1 to the second tube voltage value V2 within the allowed period Ln. Accordingly, in this situation, the adjusting function 445 adjusts the number of rows in the family of detecting elements from which the DAS 18 acquires the signals of the X-rays to a value smaller than "n". For example, the adjusting function 445 adjusts the number of rows in the family of detecting elements from which the DAS 18 acquires the signals of the X-rays to "n/2".

Further, for example, the setting function 446 sets, as yet another set of imaging conditions, a tube current value of "300 mA", a first tube voltage value V1 of "140 kV", and a second tube voltage value V2 of "80 kV". In that situation, as illustrated in FIG. 18C, it is possible to raise the tube voltage value from the second tube voltage value V2 to the first tube voltage value V1 within the allowed period Ln corresponding to the number of rows in the family of detecting elements from which the DAS 18 acquires the signals of the X-rays being "n".

However, as illustrated in FIG. 18C, when the tube current value is "300 mA", it is not possible to lower the tube voltage value from the first tube voltage value V1 to the second tube voltage value V2 within the allowed period Ln. Also, when the tube current value is "300 mA", lowering the tube voltage value from the first tube voltage value V1 to the second tube voltage value V2 takes a longer period of time than the situation where the tube current value is "500 mA". Accordingly, in this situation, the adjusting function 445 adjusts the number of rows in the family of detecting elements from which the DAS 18 acquires the signals of the X-rays to a value smaller than "n/2". For example, the adjusting function 445 adjusts the number of rows in the family of detecting elements from which the DAS 18 acquires the signals of the X-rays to "n/4".

Further, for example, the setting function 446 sets, as yet another set of imaging conditions, a tube current value of "500 mA", a first tube voltage value V1 of "150 kV", and a second tube voltage value V2 of "70 kV". In that situation, as illustrated in FIG. 19A, it is possible to raise the tube voltage value from the second tube voltage value V2 to the first tube voltage value V1 within the allowed period Ln corresponding to the number of rows in the family of detecting elements from which the DAS 18 acquires the signals of the X-rays being "n".

However, as illustrated in FIG. 19A, when the first tube voltage value V1 is "150 kV", whereas the second tube voltage value V2 is "70 kV", it is not possible to lower the tube voltage value from the first tube voltage value V1 to the second tube voltage value V2 within the allowed period Ln. Accordingly, in this situation, the adjusting function 445 adjusts the number of rows in the family of detecting elements from which the DAS 18 acquires the signals of the X-rays to a value smaller than "n". For example, the adjusting function 445 adjusts the number of rows in the family of detecting elements from which the DAS 18 acquires the signals of the X-rays to "n/2".

Further, for example, the setting function 446 sets, as yet another set of imaging conditions, a tube current value of "500 mA", a first tube voltage value V1 of "160 kV", and a second tube voltage value V2 of "60 kV". In that situation, as illustrated in FIG. 19B, it is possible to raise the tube voltage value from the second tube voltage value V2 to the first tube voltage value V1 within the allowed period Ln corresponding to the number of rows in the family of detecting elements from which the DAS 18 acquires the signals of the X-rays being "n".

However, as illustrated in FIG. 19B, when the first tube voltage value V1 is "160 kV", whereas the second tube voltage value V2 is "60 kV", it is not possible to lower the tube voltage value from the first tube voltage value V1 to the second tube voltage value V2 within the allowed period Ln. Also, when the voltage difference between the first tube voltage value V1 and the second tube voltage value V2 is "100 kV", changing the tube voltage value takes a longer period of time than the situation where the voltage difference is "80 kV". Accordingly, in this situation, the adjusting function 445 adjusts the number of rows in the family of detecting elements from which the DAS 18 acquires the signals of the X-rays to a value smaller than "n/2". For example, the adjusting function 445 adjusts the number of rows in the family of detecting elements from which the DAS 18 acquires the signals of the X-rays to "n/4".

As explained above, on the basis of the imaging conditions set by the setting function 446, the adjusting function 445 is able to adjust the number of rows in the family of detecting elements from which the DAS 18 acquires the signals of the X-rays. In one example, the adjusting function 445 adjusts the number of rows in the family of detecting elements, by comparing the imaging conditions set by the setting function 446 with a table defining a correspondence relationship between imaging conditions and the numbers of rows in the family of detecting elements.

For example, at first, the adjusting function 445 obtains, in advance, the table illustrated in FIG. 23, as the table defining the correspondence relationship between the imaging conditions and the numbers of rows in the family of detecting elements and further stores the obtained table into the memory 41. In the table in FIG. 23, the vertical axis expresses kV differences (voltage differences), whereas the horizontal axis expresses tube current values. Further, when the setting function 446 has set imaging conditions, the adjusting function 445 reads the table from the memory 41 and compares the table with the set imaging conditions. In this manner, the adjusting function 445 adjusts the number of rows in the family of detecting elements from which the DAS 18 acquires the signals of the X-rays. FIG. 23 is the table for explaining the example of the control over the allowed period according to the sixth embodiment.

For example, when a tube current value of "700 mA", a first tube voltage value V1 of "140 kV", and a second tube voltage value V2 of "80 kV" are set as imaging conditions, the adjusting function 445 at first calculates the voltage difference "60 kV". Subsequently, the adjusting function 445 obtains the number of rows "n", by referring to the tube current value "700 mA" and the voltage difference "60 kV" in the table in FIG. 23. Further, the adjusting function 445 controls the allowed period, by adjusting the number of rows in the family of detecting elements from which the DAS 18 acquires the signals of the X-rays, according to the obtained number of rows "n".

Similarly, when the tube current value is "700 mA", while the voltage difference is "80 kV", the adjusting function 445 obtains the number of rows "n/2" on the basis of the table in FIG. 23. In another example, when the tube current value is "700 mA", while the voltage difference is "100 kV", the adjusting function 445 obtains the number of rows "n/2" on the basis of the table in FIG. 23. In yet another example, when the tube current value is "500 mA", while the voltage difference is "60 kV", the adjusting function 445 obtains the number of rows "n/2" on the basis of the table in FIG. 23. In yet another example, when the tube current value is "500 mA", while the voltage difference is "80 kV", the adjusting function 445 obtains the number of rows "n/2" on the basis of the table in FIG. 23. In yet another example, when the tube current value is "500 mA", while the voltage difference is "100 kV", the adjusting function 445 obtains the number of rows "n/4" on the basis of the table in FIG. 23. In yet another example, when the tube current value is "300 mA", while the voltage difference is "60 kV", the adjusting function 445 obtains the number of rows "n/4" on the basis of the table in FIG. 23. In yet another example, when the tube current value is "300 mA", while the voltage difference is "80 kV", the adjusting function 445 obtains the number of rows "n/4" on the basis of the table in FIG. 23. In yet another example, when the tube current value is "300 mA", while the voltage difference is "100 kV", the adjusting function 445 obtains the number of rows "n/4" on the basis of the table in FIG. 23. Further, the adjusting function 445 controls the allowed period by adjusting the number of rows in the family of detecting elements from which the DAS 18 acquires the signals of the X-rays according to the obtained number of rows.

In another example, the adjusting function 445 calculates the number of rows in the family of detecting elements from the imaging conditions set by the setting function 446. For example, on the basis of the tube current value, the first tube voltage value V1, and the second tube voltage value V2 that have been set, the adjusting function 445 at first calculate the time required by lowering the tube voltage value from the first tube voltage value V1 to the second tube voltage value V2. After that, the adjusting function 445 adjusts the number of rows in the family of detecting elements from which the DAS 18 acquires the signals of the X-rays in such a manner that the allowed period is longer than the time required by lowering the tube voltage value from the first tube voltage value V1 to the second tube voltage value V2. For example, the adjusting function 445 maximizes the number of rows in the family of detecting elements from which the DAS 18 acquires the signals of the X-rays, in such a range that makes the allowed period longer than the time required by lowering the tube voltage value from the first tube voltage value V1 to the second tube voltage value V2.

Figure 24:
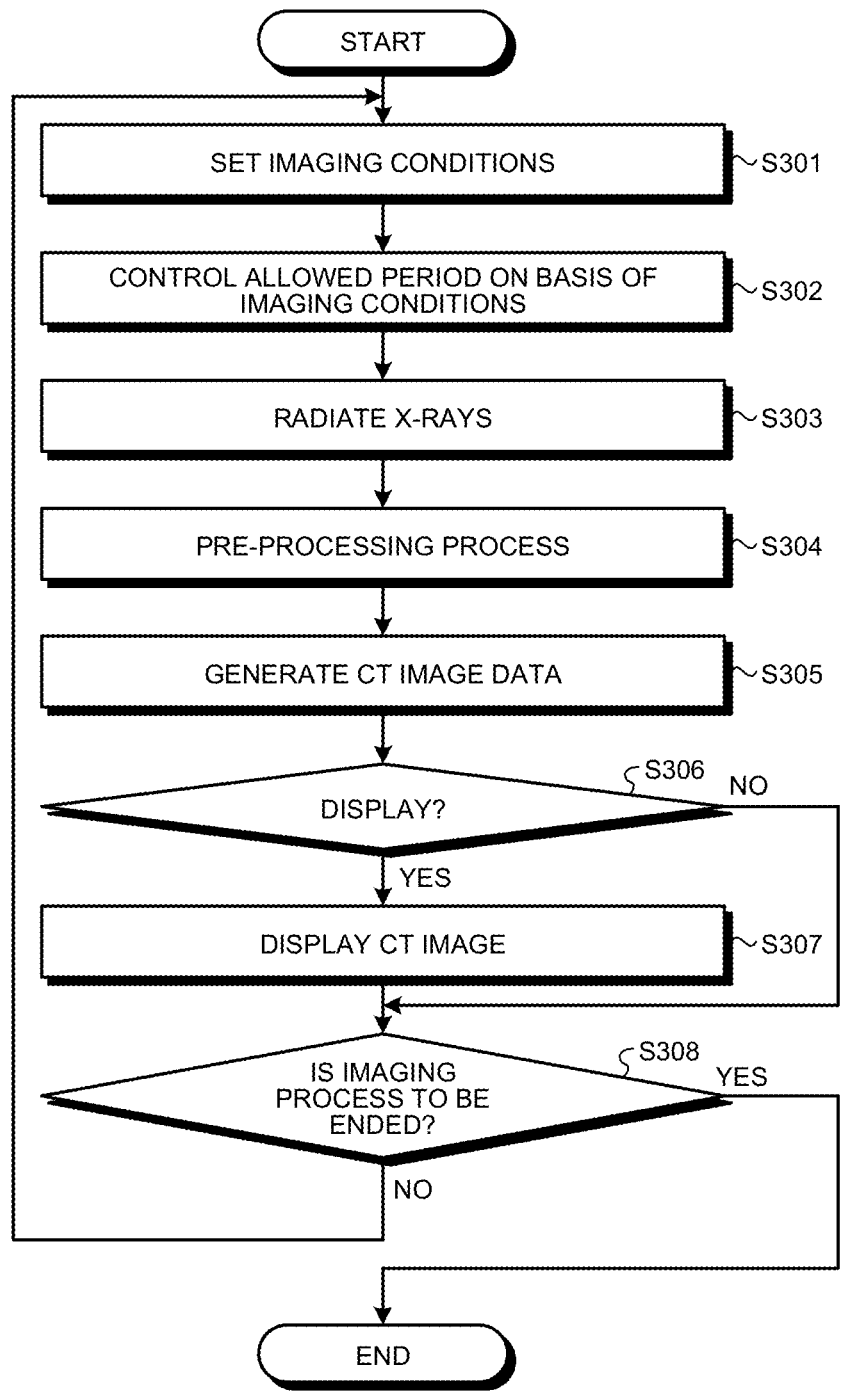
FIG. 24 is a flowchart for explaining a flow in a series of processes performed by an X-ray CT apparatus according to the sixth embodiment.

Next, an example of a procedure in processes performed by the X-ray CT apparatus 1 will be explained, with reference to FIG. 24. FIG. 24 is a flowchart for explaining the flow in the series of processes performed by the X-ray CT apparatus 1 according to the sixth embodiment.

Step S301 is a step corresponding to the setting function 446. Step S302 is a step corresponding to the adjusting function 445. Steps S303 and S308 are steps corresponding to the system controlling function 441. Step S304 is a step corresponding to the pre-processing function 442. Step S305 is a step corresponding to the generating function 443. Steps S306 and S307 are steps corresponding to the output function 444.

At first, the processing circuitry 44 sets imaging conditions (step S301). For example, the processing circuitry 44 sets imaging conditions desired by the operator, by receiving an operation to input imaging conditions from the operator via the input interface 43. Subsequently, on the basis of the set imaging conditions, the processing circuitry 44 controls the allowed period for switching the tube voltage value supplied to the X-ray tube 11, by adjusting one or both of the number of rows and the number of channels in the family of detecting elements from which the DAS 18 acquires the signals (step S302).

After that, the processing circuitry 44 causes X-rays to be generated from the X-ray tube 11 according to the imaging conditions set at step S301 and causes the generated X-rays to be radiated onto the patient P (step S303). In that situation, by switching the tube voltage value to be supplied to the X-ray tube 11, the processing circuitry 44 changes the energy of the X-rays for every one or more views. Further, the DAS 18 generates detection data by sequentially acquiring the signals of the X-rays, in correspondence with each family of detecting elements of which one or both of the number of rows and the number of channels were adjusted at step S302. Further, the processing circuitry 44 performs a pre-processing process on the detection data output from the DAS 18 (step S304). Further, the processing circuitry 44 generates CT image data on the basis of the data (raw data) resulting from the pre-processing process (step S305).

In this situation, the processing circuitry 44 judges whether or not a CT image is to be displayed (step S306). When a CT image is to be displayed because, for example, a display instruction is received from the operator (step S306: Yes), the processing circuitry 44 generates a display-purpose CT image on the basis of the CT image data and causes the display 42 to display the generated CT image (step S307). On the contrary, when a CT image is not to be displayed (step S306: No), or after step S307 is performed, the processing circuitry 44 judges whether or not the imaging process is to be ended (step S308). When the imaging process is not to be ended because, for example, there is an additional imaging process to be performed (step S308: No), the processing circuitry 44 returns to step S301. On the contrary, when it is determined that the imaging process is to be ended (step S308: Yes), the processing circuitry 44 ends the process.

As explained above, the setting function 446 according to the sixth embodiment is configured to set the imaging conditions. Further, on the basis of the imaging conditions set by the setting function 446, the adjusting function 445 is configured to control the allowed period by adjusting one or both of the number of rows and the number of channels in the family of detecting elements from which the DAS 18 acquires the signals of the X-rays. Consequently, the X-ray CT apparatus 1 according to the sixth embodiment is able to enhance the degree of freedom of the imaging conditions, when performing the dual-energy acquisition by using the fast switching while employing the DAS 18 that uses the sequential acquisition method. In other words, the X-ray CT apparatus 1 is able to enhance the degree of freedom of the imaging conditions, by setting the imaging conditions at first while exercising control so as to complete the switching of the tube voltage value within the allowed period.

In the fifth embodiment described above, the example was explained in which the imaging conditions were set on the basis of the allowed period resulting from the control exercised by the adjusting function 445. In contrast, as a seventh embodiment, an example will be explained in which the imaging conditions are set, while taking into consideration not only the allowed period but also the imaging time.

The X-ray CT apparatus 1 according to the seventh embodiment has a configuration similar to that of the X-ray CT apparatus 1 illustrated in FIG. 12, while a part of the processes performed by the system controlling function 441 is different. In the following sections, some of the constituent elements having the same configurations as those explained in the fifth embodiment will be referred to by using the same reference characters as in FIG. 12, and the explanations thereof will be omitted. In the present embodiment, an example will be explained in which each of a plurality of DASs 18 is connected to the n detecting elements (the detecting elements 121 to 12n) arranged along the row direction of the X-ray detector 12.

The adjusting function 445 at first obtains the imaging range of the imaging process to be performed on the patient P. For example, the adjusting function 445 obtains the imaging range by receiving an operation to input the imaging range from the operator via the input interface 43. Alternatively, for example, the adjusting function 445 may automatically obtain the imaging range on the basis of position determining image data acquired in the position determining imaging process. In another example, the adjusting function 445 may automatically obtain the imaging range from a system such as a Radiology Information System (RIS) or a Hospital Information System (HIS), via a network. For example, as the imaging range, the adjusting function 445 obtains the length in the body axis direction of the patient P.

Further, the adjusting function 445 obtains a predetermined imaging time of the imaging process to be performed on the patient P. In this situation, the predetermined imaging time is an upper limit value for the imaging time that can be set for the imaging process to be performed on the patient P. For example, in an imaging process performed on the chest or the abdomen of the patient P, the patient P holds his/her breath until the imaging process is completed. In that situation, as the predetermined imaging time, the adjusting function 445 obtains a time period (hereinafter, "breath holding time period") during which the patient P is able to hold his/her breath.

For example, the adjusting function 445 obtains the breath holding time period, by receiving an operation to input the breath holding time period corresponding to the patient P, from the operator. Alternatively, for example, the adjusting function 445 may obtain a pre-set value that was set in advance, as the breath holding time period. In another example, the adjusting function 445 may obtain patient information (e.g., his/her health condition, age, physique, etc.) of the patient P from a system such as the RIS or the HIS and may set the breath holding time period of the patient P on the basis of the patient information. For example, when the patient P has a disease in the lungs, the adjusting function 445 sets the breath holding time period to "5 seconds". When the patient P does not have a disease in the lungs, the adjusting function 445 sets the breath holding time period to "10 seconds".

Figures 25, 26:
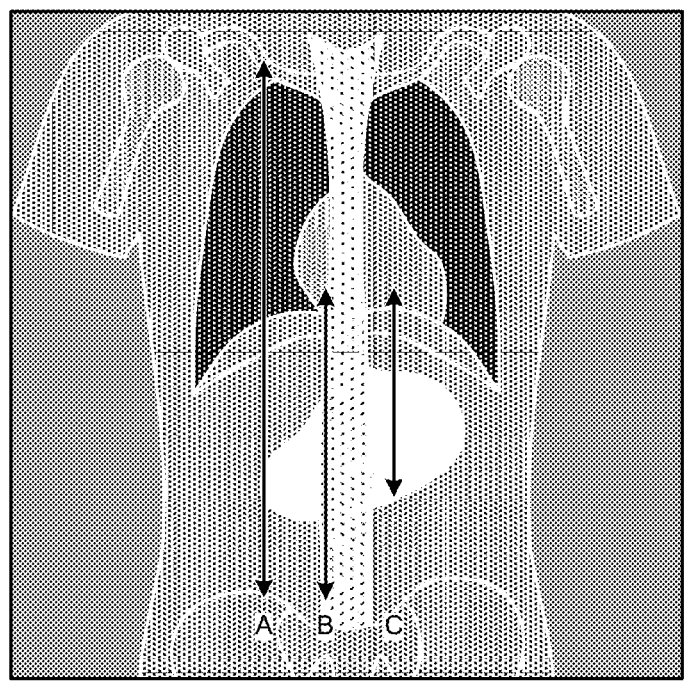
FIG. 25 is a table for explaining an example of control over an allowed time period according to a seventh embodiment.
FIG. 26 is a drawing for explaining an example of the control over the allowed time period according to the seventh embodiment.

Subsequently, on the basis of the imaging range, the adjusting function 445 adjusts one or both of the number of rows and the number of channels in the family of detecting elements from which the DAS 18 acquires the signals, so that the imaging process is to be completed within the predetermined imaging time. In the following sections, an example will be explained in which, as illustrated in FIG. 25, the imaging range is "500 mm", while the predetermined imaging time is "10 seconds". FIG. 25 is a table for explaining the example of the control over the allowed period according to the seventh embodiment.

For example, the adjusting function 445 obtains the length "500 mm" of a span A as the imaging range, by receiving an operation to set the span A illustrated in FIG. 26, from the operator who referenced the position determining image data. Further, because the span A contains the chest, the adjusting function 445 obtains the breath holding time period of the patient P as the predetermined imaging time.

FIG. 26 is a drawing for explaining the example of the control over the allowed period according to the seventh embodiment.

Subsequently, on the basis of the imaging range, the adjusting function 445 calculates an imaging time corresponding to the number of rows in the family of detecting elements from which the DAS 18 acquires the signals. For example, as illustrated in FIG. 25, on the basis of the imaging range "500 mm", the adjusting function 445 calculates an imaging time "6.25 seconds" corresponding to the number of rows "n". Further, on the basis of the imaging range "500 mm", the adjusting function 445 calculates another imaging time "12.5 seconds" corresponding to the number of rows "n/2". Also, on the basis of the imaging range "500 mm", the adjusting function 445 calculates another imaging time "25 seconds" corresponding to the number of rows "n/4".

In one example, the adjusting function 445 at first calculates the width in the row direction of an imaging target region of the patient P, in accordance with the number of rows in the family of detecting elements. After that, on the basis of the width in the row direction of the imaging target region and the beam pitch, the adjusting function 445 calculates a moving amount of the patient P with respect to the gantry 10, while the rotating part of the X-ray CT apparatus 1 makes one turn. In this situation, the beam pitch is a set value indicating a ratio between the moving amount of the patient P with respect to the gantry 10 while the rotating part makes one turn and the width in the row direction of the imaging target region of the patient P. Subsequently, the adjusting function 445 calculates the imaging time corresponding to the number of rows in the family of detecting elements, by dividing the imaging range by the product of the moving amount of the patient P with respect to the gantry 10 while the rotating part makes one turn and the rotating speed of the rotating part.

Subsequently, the adjusting function 445 identifies the number of rows that makes the imaging time corresponding to the number of rows shorter than the predetermined imaging time, by comparing the imaging time corresponding to the number of rows with the predetermined imaging time. In the following sections, the number of rows that makes the imaging time corresponding to the number of rows shorter than the predetermined imaging time will be referred to as a number-of-rows candidate. In other words, the adjusting function 445 identifies one or more number-of-rows candidates by comparing the imaging time corresponding to the number of rows with the predetermined imaging time.

For example, in FIG. 25, the imaging time corresponding to the number of rows "n/2" is "12.5 seconds", whereas the imaging time corresponding to the number of rows "n/4" is "25 seconds". In other words, the imaging time corresponding to the number of rows "n/2" and the imaging time corresponding to the number of rows "n/4" both exceed the predetermined imaging time "10 seconds". It means that, when the number of rows in the family of detecting elements is set to "n/2" or "n/4", it takes longer than the predetermined imaging time "10 seconds" to complete the imaging process. Accordingly, the adjusting function 445 will not identify "n/2" and "n/4" as the number-of-rows candidate.

Further, in FIG. 25, the imaging time corresponding to the number of rows "n" is "6.25 seconds". In other words, the imaging time corresponding to the number of rows "n" is shorter than the predetermined imaging time "10 seconds". It means that, when the number of rows in the family of detecting elements is set to "n", it is possible to complete the imaging process within the predetermined imaging time "10 seconds". Accordingly, the adjusting function 445 identifies "n" as a number-of-rows candidate.

When there is one number-of-rows candidate, the adjusting function 445 adjusts the number of rows in the family of detecting elements from which the DAS 18 acquires the signals, according to the number-of-rows candidate. For example, in the example in FIG. 25, the adjusting function 445 adjusts the number of rows in the family of detecting elements from which the DAS 18 acquires the signals to "n". In contrast, when there are two or more number-of-rows candidates, the adjusting function 445 receives an operation to select one of the candidates from the operator and adjusts the number of rows in the family of detecting elements from which the DAS 18 acquires the signals, according to the selected number-of-rows candidate.

As explained above, on the basis of the imaging range, the adjusting function 445 is configured to calculate the imaging time corresponding to the number of rows. Further, the adjusting function 445 is configured to identify the number of rows that makes the imaging time corresponding to the number of rows shorter than the predetermined imaging time, as the number-of-rows candidate. Further, the adjusting function 445 is configured to adjust the number of rows in the family of detecting elements from which the DAS 18 acquires the signals, on the basis of the number-of-rows candidate. In other words, the adjusting function 445 is configured to adjust the number of rows in the family of detecting elements from which the DAS 18 acquires the signals, so that the imaging process is to be completed within the predetermined imaging time. Further, by adjusting the number of rows in the family of detecting elements, the adjusting function 445 is configured to control the allowed period for switching the tube voltage value to be supplied to the X-ray tube 11 when the dual-energy acquisition using the fast switching is performed.

In the example in FIG. 25, when the predetermined imaging time is "5 seconds", or the like, the imaging time corresponding to the number of rows exceeds the predetermined imaging time "10 seconds", in all of the situations where the number of rows in the family of detecting elements is set to "n", the number of rows in the family of detecting elements is set to "n/2", and the number of rows in the family of detecting elements is set to "n/4". In other words, there may be some situations where the adjusting function 445 is not able to identify any number-of-rows candidate.

In those situations, the adjusting function 445 is configured to adjust the imaging pitch, for example. In the present example, the imaging pitch refers to a beam pitch or a helical pitch, for example. The beam pitch denotes the ratio between the moving amount of the patient P with respect to the gantry 10 while the rotating part of the X-ray CT apparatus 1 makes one turn and the width in the row direction of the imaging target region of the patient P. Further, the helical pitch denotes the ratio between the moving amount of the patient P with respect to the gantry 10 while the rotating part of the X-ray CT apparatus 1 makes one turn and the width (a collimation width) corresponding to one row of detecting elements in the imaging target region of the patient P. The moving amount of the patient P with respect to the gantry 10 while the rotating part of the X-ray CT apparatus 1 makes one turn can be adjusted, for example, with the moving speed of the tabletop 33 during the imaging process. In the present embodiment, an example in which the beam pitch is adjusted will be explained.

For example, when it is not possible to identify any number-of-rows candidates, the adjusting function 445 adjusts the moving speed of the tabletop or the like so as to increase the beam pitch. Further, on the basis of the adjusted beam pitch, the adjusting function 445 re-calculates an imaging time corresponding to the number of rows. In this situation, as a result of the beam pitch being increased, the adjusting function 445 is configured to re-calculate a shorter time period as the imaging time corresponding to the number of rows.

For example, as an imaging time corresponding to the number of rows "n", the adjusting function 445 calculates a time period shorter than "6.25 seconds". Further, as an imaging time corresponding to the number of rows "n/2", the adjusting function 445 calculates a time period shorter than "12.5 seconds". Further, as an imaging time corresponding to the number of rows "n/4", the adjusting function 445 calculates a time period shorter than "25 seconds". As a result, the adjusting function 445 is able to adjust the number of rows in the family of detecting elements from which the DAS 18 acquires the signals, by identifying at least one number-of-rows candidate, even when the predetermined imaging time is "5 seconds", or the like. In other words, the adjusting function 445 is configured to adjust the number of rows in the family of detecting elements from which the DAS 18 acquires the signals and the pitch for the imaging process, so that the imaging process is to be completed within the predetermined imaging time.

Further, on the basis of the allowed period resulting from the control exercised by the adjusting function 445, the setting function 446 is configured to set imaging conditions. For example, the setting function 446 obtains, in advance, a table defining, for each set made up of a tube current value, a first tube voltage value V1, and a second tube voltage value V2, the time required by lowering the tube voltage value from the first tube voltage value V1 to the second tube voltage value V2 and further stores the obtained table into the memory 41. Further, on the basis of the allowed period resulting from the control exercised by the adjusting function 445 and the table stored in the memory 41, the setting function 446 sets a tube current value, a first tube voltage value V1, and a second tube voltage value V2. More specifically, the setting function 446 sets the tube current value, the first tube voltage value V1, and the second tube voltage value V2, to make it possible to switch the tube voltage value to be supplied to the X-ray tube 11 between the first tube voltage value V1 and the second tube voltage value V2 within the allowed period resulting from the control exercised by the adjusting function 445.

For example, as illustrated in FIGS. 18B and 18C, while the first tube voltage value V1 is "140 kV", whereas the second tube voltage value V2 is "80 kV", when the tube current value is set to "500 mA" or "300 mA", it is not possible to lower the tube voltage value from the first tube voltage value V1 to the second tube voltage value V2 within the allowed period Ln corresponding to the number of rows in the family of detecting elements being "n". In contrast, as illustrated in FIG. 18A, when the tube current value is set to "700 mA", it is possible to lower the tube voltage value from the first tube voltage value V1 to the second tube voltage value V2 within the allowed period Ln. Accordingly, when the number of rows in the family of detecting elements has been adjusted to "n", the setting function 446 sets the tube current value of the X-ray tube to "700 mA".

The example was explained above in which the length "500 mm" of the span "A" illustrated in FIG. 26 is obtained as the imaging range. However, the adjusting function 445 is also capable of adjusting the number of rows in the family of detecting elements, similarly in the situation where the length of a span B or a span C is obtained as an imaging range.

For example, the adjusting function 445 receives an operation to set the span B illustrated in FIG. 26 from the operator who referenced the position determining image data and obtains the length "300 mm" of the span B as an imaging range. In this situation, as illustrated in FIG. 27, on the basis of the imaging range "300 mm", the adjusting function 445 adjusts the number of rows in the family of detecting elements from which the DAS 18 acquires the signals to "n/2", so that the imaging process is to be completed within the predetermined imaging time "10 seconds". FIG. 27 is a table for explaining the example of the control over the allowed period according to the seventh embodiment.

When the imaging range is "300 mm", the imaging time corresponding to the number of rows "n" is "3.75 seconds", which is a half of "7.5 seconds". In other words, when the imaging range is "300 mm", there are two numbers of rows (number-of-rows candidates), namely "n" and "n/2", that make the imaging time corresponding to the number of rows shorter than the predetermined imaging time. In this situation, the adjusting function 445 receives an operation to select one of the candidates from the operator. For example, when the operator prioritizes the degree of freedom of the imaging conditions, the operator selects "n/2". In contrast, when the operator prioritizes shortening the imaging time, the operator selects "n". FIG. 27 illustrates the example in which "n/2" is selected from between the two number-of-rows candidates.

Further, for example, the adjusting function 445 receives an operation to set the span C illustrated in FIG. 26 from the operator who referenced the position determining image data and obtains the length "200 mm" of the span C as an imaging range. In this situation, as illustrated in FIG. 27, on the basis of the imaging range "200 mm", the adjusting function 445 adjusts the number of rows in the family of detecting elements from which the DAS 18 acquires the signals to "n/4", so that the imaging process is to be completed within the predetermined imaging time "10 seconds".

When the imaging range is "200 mm", the imaging time corresponding to the number of rows "n/2" is "5 seconds", which is a half of "10 seconds", and the imaging time corresponding to the number of rows "n" is "2.5 seconds", which is a quarter of "10 seconds". In other words, when the imaging range is "200 mm", there are three numbers of rows (number-of-rows candidates), namely "n", "n/2", and "n/4", that make the imaging time corresponding to the number of rows shorter than the predetermined imaging time.

Accordingly, the adjusting function 445 receives an operation to select one of the candidates from the operator. FIG. 27 illustrates the example in which "n/4" is selected from among the three number-of-rows candidates.

Figure 28:
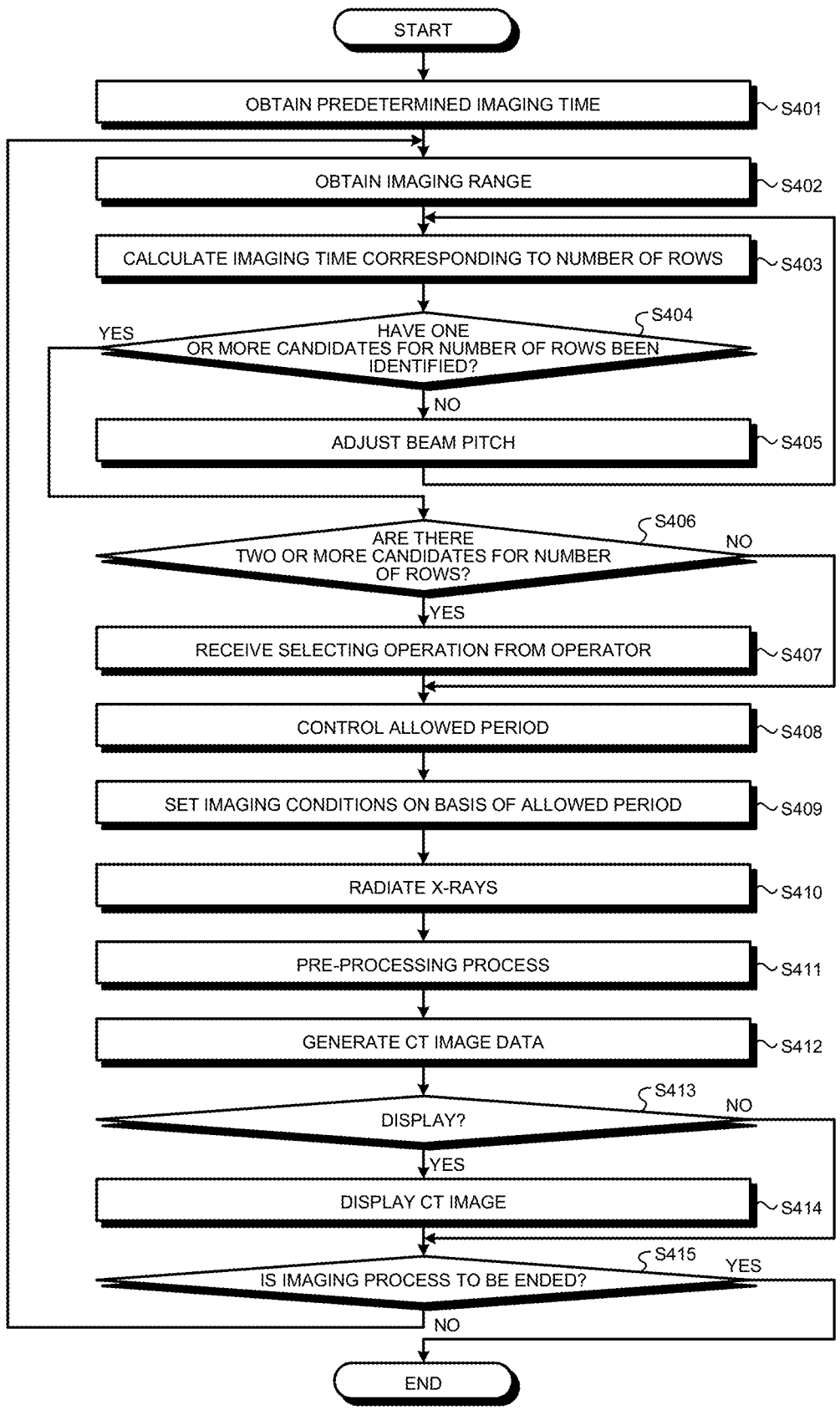
FIG. 28 is a flowchart for explaining a flow in a series of processes performed by an X-ray CT apparatus according to the seventh embodiment.

Next, an example of a procedure in processes performed by the X-ray CT apparatus 1 according to the seventh embodiment will be explained, with reference to FIG. 28. FIG. 28 is a flowchart for explaining the flow in the series of processes performed by the X-ray CT apparatus 1 according to the seventh embodiment.

Steps S401, S402, S403, S404, S405, S406, S407, and S408 are steps corresponding to the adjusting function 445. Step S409 is a step corresponding to the setting function 446. Steps S410 and S415 are steps corresponding to the system controlling function 441. Step S441 is a step corresponding to the pre-processing function 442. Step S412 is a step corresponding to the generating function 443. Steps S413 and S414 are steps corresponding to the output function 444.

First, the processing circuitry 44 obtains the predetermined imaging time (step S401). Further, the processing circuitry 44 obtains the imaging range (step S402). Subsequently, on the basis of the imaging range, the processing circuitry 44 calculates an imaging time corresponding to the number of rows in the family of detecting elements from which the DAS 18 acquires the signals (step S403). For example, the processing circuitry 44 calculates an imaging time required by completing the imaging process on the imaging range, with respect to each of the numbers of rows "n", "n/2", and "n/4".

In this situation, the processing circuitry 44 judges whether or not one or more number-of-rows candidates have been identified on the basis of the predetermined imaging time and the imaging times corresponding to the numbers of rows (step S404). When no number-of-rows candidate has been identified (step S404: No), the processing circuitry 44 adjusts the beam pitch (step S405) and returns to step S403.

On the contrary, when at least one number-of-rows candidate has been identified (step S404: Yes), the processing circuitry 44 judges whether there are two or more number-of-rows candidates (step S406). When there are two or more number-of-rows candidates (step S406: Yes), the processing circuitry 44 receives an operation to select one of the number-of-rows candidates from the operator (step S407).

In contrast, when there are not two or more number-of-rows candidates, for example, when the number of rows that makes it possible to complete the imaging process on the imaging range within the predetermined imaging time is only "n" (step S406: No), or after step S407 is performed, the processing circuitry 44 controls the allowed period for switching the tube voltage value to be supplied to the X-ray tube 11, by adjusting the number of rows in the family of detecting elements from which the DAS 18 acquires the signals (step S408). Further, on the basis of the allowed period resulting from the control, the processing circuitry 44 sets imaging conditions such as a tube current value, a tube voltage value, and the like (step S409).

Subsequently, the processing circuitry 44 causes X-rays to be generated from the X-ray tube 11 according to the imaging conditions set at step S409 and causes the generated X-rays to be radiated onto the patient P (step S410). In this situation, by switching the tube voltage value to be supplied to the X-ray tube 11, the processing circuitry 44 changes the energy of the X-rays for every one or more views. Further, the DAS 18 generates detection data by sequentially acquiring the signals of the X-rays in correspondence with each family of detecting elements in which the number of rows has been adjusted at step S408. Further, the processing circuitry 44 performs the pre-processing process on the detection data output from the DAS 18 (step S411). Further, on the basis of the data (the raw data) resulting from the pre-processing process, the processing circuitry 44 generates CT image data (step S412).

In this situation, the processing circuitry 44 judges whether or not a CT image is to be displayed (step S413). When a CT image is to be displayed because, for example, a display instruction is received from the operator (step S413: Yes), the processing circuitry 44 generates a display-purpose CT image on the basis of the CT image data and causes the display 42 to display the generated CT image (step S414). On the contrary, when a CT image is not to be displayed (step S413: No), or after step S414 is performed, the processing circuitry 44 judges whether or not the imaging process is to be ended (step S415). When the imaging process is not to be ended because, for example, there is an additional imaging process to be performed (step S415: No), the processing circuitry 44 returns to step S402. On the contrary, when it is determined that the imaging process is to be ended (step S415: Yes), the processing circuitry 44 ends the process.

Alternatively, when the imaging process is not to be ended (step S415: No), the processing circuitry 44 may return to step S401. In other words, the processing circuitry 44 may obtain a predetermined imaging time for each imaging process. Further, in that situation, step S401 may be performed at any arbitrary time before step S404.

As explained above, on the basis of the imaging range, the adjusting function 445 according to the seventh embodiment is configured to adjust the number of rows in the family of detecting elements from which the DAS 18 acquires the signals, so that the imaging process is to be completed within the predetermined imaging time. More specifically, the adjusting function 445 is configured to calculate, on the basis of the imaging range, the imaging time corresponding to the number of rows, to identify the number of rows that makes the imaging time corresponding to the number of rows shorter than the predetermined imaging time as the number-of-rows candidate, and to adjust the number of rows in the family of detecting elements from which the DAS 18 acquires signals on the basis of the number-of-rows candidate. Consequently, the X-ray CT apparatus 1 according to the seventh embodiment is able to enhance the degree of freedom of the imaging conditions and to also exercise control so that the switching of the tube voltage value is completed within the allowed period, and is further able to complete the imaging process within the predetermined imaging time.

Further, as explained above, when it is not possible to identify the number of rows (the number-of-rows candidate) that makes it possible to complete the imaging process on the imaging range within the predetermined imaging time, the adjusting function 445 is configured to adjust the pitch for the imaging process. In other words, the adjusting function 445 is configured to adjust the number of rows in the family of detecting elements from which the DAS 18 acquires the signals and the pitch for the imaging process, so that the imaging process is to be completed within the predetermined imaging time. Consequently, even when the imaging range is long, or the like, the X-ray CT apparatus 1 according to the seventh embodiment is able to complete the imaging process within the predetermined imaging time by adjusting the pitch for the imaging process.

In the sixth embodiment described above, the example is explained in which the allowed period is controlled by adjusting one or both of the number of rows and the number of channels in the family of detecting elements from which the DAS 18 acquires the signals of the X-rays, on the basis of the imaging conditions set by the setting function 446. In contrast, as an eighth embodiment, an example will be explained in which the allowed period is controlled while taking into consideration not only the imaging conditions but also the imaging time.

The X-ray CT apparatus 1 according to the eighth embodiment has a configuration similar to that of the X-ray CT apparatus 1 illustrated in FIG. 12, while a part of the processes performed by the system controlling function 441 is different. In the following sections, some of the constituent elements having the same configurations as those explained in the fifth embodiment will be referred to by using the same reference characters as in FIG. 12, and the explanations thereof will be omitted. In the present embodiment, an example will be explained in which each of a plurality of DASs 18 is connected to the n detecting elements (the detecting elements 121 to 12n) arranged along the row direction of the X-ray detector 12.

At first, the adjusting function 445 obtains the imaging range of the imaging process to be performed on the patient P. For example, the adjusting function 445 obtains the imaging range by receiving an operation to input the imaging range from the operator via the input interface 43. Alternatively, for example, the adjusting function 445 may automatically obtain the imaging range on the basis of the position determining image data acquired in the position determining imaging process. In another example, the adjusting function 445 may automatically obtain the imaging range from a system such as the RIS or the HIS via a network. In the following sections, as an example, the situation will be explained in which the imaging range is "500 mm", as illustrated in FIG. 29. FIG. 29 is a table for explaining the example of the control over the allowed period according to the eighth embodiment.

Further, the adjusting function 445 obtains the predetermined imaging time of the imaging process performed on the patient P. For example, the adjusting function 445 obtains the predetermined imaging time by receiving an operation to input the breath holding time period corresponding to the patient P, from the operator.

Alternatively, the adjusting function 445 may obtain a pre-set value that was set in advance, as the predetermined imaging time. In another example, the adjusting function 445 may obtain the breath holding time period of the patient P based on patient information, as the predetermined imaging time. In the following sections, as an example, the situation will be explained in which the predetermined imaging time is "10 seconds", as illustrated in FIG. 29.

Further, the setting function 446 sets imaging conditions such as a tube current value, a tube voltage value, and the like. For example, the setting function 446 sets the imaging conditions by receiving an operation to input the imaging conditions from the operator, via the input interface 43. Alternatively, the setting function 446 may automatically set imaging conditions on the basis of the position determining image data acquired in the position determining imaging process. In another example, the setting function 446 may set pre-set conditions that were set in advance as the imaging conditions. In the following sections, as an example, the situation will be explained in which a tube current value "500 mA", a first tube voltage value V1 "140 kV", and a second tube voltage value V2 "80 kV" are set as the imaging conditions, as illustrated in FIG. 29.

Subsequently, the adjusting function 445 identifies one or more numbers of rows that are selectable, on the basis of the imaging conditions set by the setting function 446. For example, at first, the adjusting function 445 obtains the allowed period corresponding to the number of rows in the family of detecting elements from which the DAS 18 acquires the signals of the X-rays being "n", the allowed period corresponding to the number of rows in the family of detecting elements being "n/2", and the allowed period corresponding to the number of rows in the family of detecting elements being "n/4". These allowed periods are measured in advance, for example, and stored in the memory 41 in correspondence with the numbers of rows in the family of detecting elements. After that, with respect to each of the obtained plurality of allowed periods, the adjusting function 445 judges whether or not it is possible to switch the tube voltage value between the first tube voltage value V1 and the second tube voltage value V2 within the allowed period.

In the following sections, let us assume that it is possible to switch the tube voltage value between the first tube voltage value V1 "140 kV" and the second tube voltage value V2 "80 kV" within the allowed period corresponding to the number of rows in the family of detecting elements being "n". Further, in the following sections, let us also assume that it is possible to switch the tube voltage value between the first tube voltage value V1 "140 kV" and the second tube voltage value V2 "80 kV" within the allowed period corresponding to the number of rows in the family of detecting elements being "n/2". Further, in the following sections, let us also assume that it is not possible to switch the tube voltage value between the first tube voltage value V1 "140 kV" and the second tube voltage value V2 "80 kV" within the allowed period corresponding to the number of rows in the family of detecting elements being "n/4". In this situation, the adjusting function 445 identifies "n" and "n/2" as the numbers of rows that are selectable, as illustrated in FIG. 29.

Subsequently, on the basis of the selectable numbers of rows and the imaging range, the adjusting function 445 calculates an imaging time corresponding to the number of rows in the family of detecting elements from which the DAS 18 acquires the signals. For example, as illustrated in FIG. 29, on the basis of the selectable number of rows "n" and the imaging range "500 mm", the adjusting function 445 calculates an imaging time "6.25 seconds" corresponding to the number of rows "n". Further, on the basis of the selectable number of rows "n/2" and the imaging range "500 mm", the adjusting function 445 calculates an imaging time "12.5 seconds" corresponding to the number of rows "n/2".

After that, the adjusting function 445 identifies number-of-rows candidates, by comparing the imaging times corresponding to the numbers of rows with the predetermined imaging time. For example, in the example in FIG. 29, the imaging time corresponding to the number of rows "n/2" is "12.5 seconds". In other words, the imaging time corresponding to the number of rows "n/2" exceeds the predetermined imaging time "10 seconds". Accordingly, the adjusting function 445 does not identify the number of rows "n/2" as a number-of-rows candidate.

Further, in the example in FIG. 29, the imaging time corresponding to the number of rows "n" is "6.25 seconds". In other words, the imaging time corresponding to the number of rows "n" is shorter than the predetermined imaging time "10 seconds". Accordingly, the adjusting function 445 identifies the number of rows "n" as a number-of-rows candidate. When there is one number-of-rows candidate, the adjusting function 445 adjusts the number of rows in the family of detecting elements from which the DAS 18 acquires the signals, according to the number-of-rows candidate. In another example, when there are two or more number-of-rows candidates, the adjusting function 445 receives an operation to select one of the candidates from the operator and further adjusts the number of rows in the family of detecting elements according to the selected number-of-rows candidate.

As explained above, the adjusting function 445 is configured to identify the one or more number-of-rows candidates on the basis of the predetermined imaging time and to adjust the number of rows in the family of detecting elements from which the DAS 18 acquires the signals. In other words, the adjusting function 445 is configured to adjust the number of rows in the family of detecting elements from which the DAS 18 acquires the signals, so that the imaging process is to be completed within the predetermined imaging time. Further, by adjusting the number of rows in the family of detecting elements, the adjusting function 445 is configured to control the allowed period for switching the tube voltage value to be supplied to the X-ray tube 11 when the dual-energy acquisition is performed by using the fast switching.

In the example in FIG. 29, when the predetermined imaging time is "5 seconds" or the like, in both of the situations where the number of rows in the family of detecting elements is "n" and where the number of rows in the family of detecting elements is "n/2", the imaging time corresponding to the number of rows exceeds the predetermined imaging time "10 seconds". In other words, there may be some situations where the adjusting function 445 is not able to identify any number-of-rows candidate. In those situations, the adjusting function 445 is configured to adjust the pitch (a beam pitch, a helical pitch, or the like) for the imaging process. In the present embodiment, an example in which the beam pitch is adjusted will be explained.

For example, when it is not possible to identify any number-of-rows candidate, the adjusting function 445 is configured to adjust the moving speed of the tabletop or the like so as to increase the beam pitch. Further, on the basis of the adjusted beam pitch, the adjusting function 445 is configured to re-calculate an imaging time corresponding to the number of rows. In this situation, as a result of the beam pitch being increased, the adjusting function 445 is able to re-calculate a shorter time period as the imaging time corresponding to the number of rows.

For example, as an imaging time corresponding to the number of rows "n", the adjusting function 445 calculates a time period shorter than "6.25 seconds". Further, as an imaging time corresponding to the number of rows "n/2", the adjusting function 445 calculates a time period shorter than "12.5". As a result, even when the predetermined imaging time is "5 seconds" or the like, the adjusting function 445 is able to identify at least one number-of-rows candidate and is thus able to adjust the number of rows in the family of detecting elements from which the DAS 18 acquires the signals. In other words, the adjusting function 445 is configured to adjust the number of rows in the family of detecting elements from which the DAS 18 acquires the signals and the pitch for the imaging process, so that the imaging process is to be completed within the predetermined imaging time.

As a result of increasing the pitch, there is a possibility that the image quality of the acquired CT image data may become degraded. Accordingly, when the image quality of the CT image data is important, the adjusting function 445 may avoid increasing the beam pitch by changing the imaging conditions, or the like. In contrast, when the imaging conditions that were set are important, e.g., when the information from the dual-energy acquisition is important or when reducing the radiation dose in the imaging process is important, the adjusting function 445 maintains the imaging conditions, by increasing the beam pitch.

Figure 30:
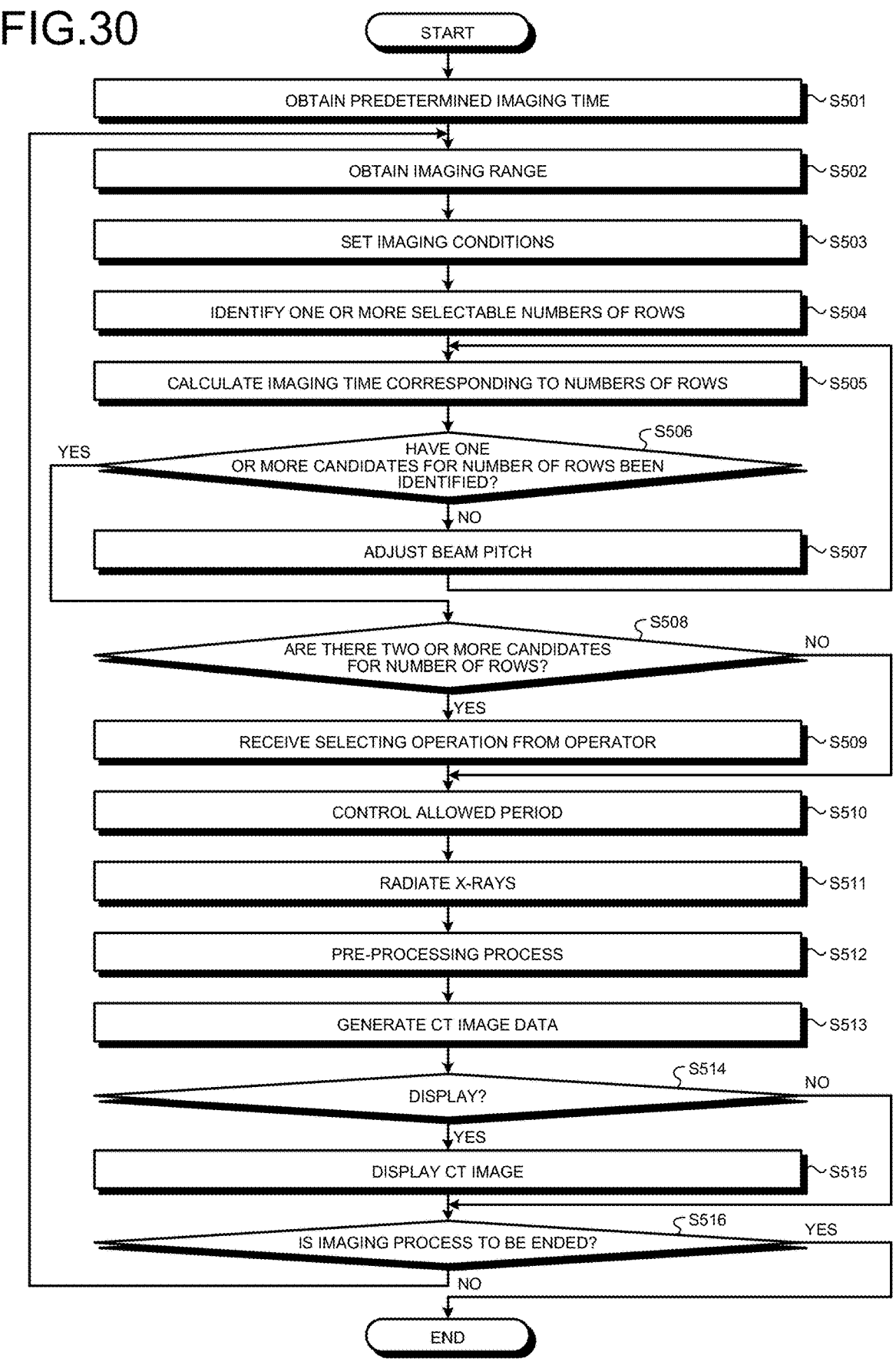
FIG. 30 is a flowchart for explaining a flow in a series of processes performed by an X-ray CT apparatus according to the eighth embodiment.

Next, an example of a procedure in processes performed by the X-ray CT apparatus 1 according to the eighth embodiment will be explained with reference to FIG. 30. FIG. 30 is a flowchart for explaining the flow in the series of processes performed by the X-ray CT apparatus 1 according to the eighth embodiment.

Steps S501, S502, S504, S505, S506, S507, S508, S509, and S510 are steps corresponding to the adjusting function 445. Step S503 is a step corresponding to the setting function 446. Steps S511 and S516 are steps corresponding to the system controlling function 441. Step S512 is a step corresponding to the pre-processing function 442. Step S513 is a step corresponding to the generating function 443. Steps S514 and S515 are steps corresponding to the output function 444.

At first, the processing circuitry 44 obtains the predetermined imaging process (step S501). Further, the processing circuitry 44 obtains the imaging range (step S502). Step S502 may be performed at any arbitrary time before step S505. Further, the processing circuitry 44 sets imaging conditions (step S503). For example, by receiving an operation to input the imaging conditions from the operator via the input interface 43, the processing circuitry 44 sets the imaging conditions desired by the operator.

Further, on the basis of the imaging conditions obtained at step S503, the processing circuitry 44 identifies one or more numbers of rows that are selectable (step S504). For example, on the basis of whether or not it is possible to switch the tube voltage value within the allowed period, the processing circuitry 44 identifies the numbers of rows "n" and "n/2" as the numbers of rows that are selectable.

Further, on the basis of the imaging range obtained at step S502, with respect to each of the identified numbers of rows, the processing circuitry 44 calculates an imaging time corresponding to the number of rows (step S505). For example, with respect to each of the numbers of rows "n" and "n/2", the processing circuitry 44 calculates the imaging time required by completing the imaging process on the imaging range.

In this situation, the processing circuitry 44 judges whether or not one or more number-of-rows candidates have been identified on the basis of the predetermined imaging time and the imaging time corresponding to the number of rows (step S506). When no number-of-rows candidate has been identified (step S506: No), the processing circuitry 44 adjusts the beam pitch (step S507) and returns to step S505.

On the contrary, when at least one number-of-rows candidate has been identified (step S506: Yes), the processing circuitry 44 judges whether there are two or more number-of-rows candidates (step S508). When there are two or more number-of-rows candidates (step S508: Yes), the processing circuitry 44 receives an operation to select one of the number-of-rows candidates from the operator (step S509).

In contrast, when there are not two or more number-of-rows candidates, for example, when the number of rows that makes it possible to complete the imaging process on the imaging range within the predetermined imaging time is only "n" (step S508: No), or after step S509 is performed, the processing circuitry 44 controls the allowed period for switching the tube voltage value to be supplied to the X-ray tube 11, by adjusting the number of rows in the family of detecting elements from which the DAS 18 acquires the signals (step S510).

Subsequently, the processing circuitry 44 causes X-rays to be generated from the X-ray tube 11 according to the imaging conditions set at step S503 and causes the generated X-rays to be radiated onto the patient P (step S511). In this situation, by switching the tube voltage value to be supplied to the X-ray tube 11, the processing circuitry 44 changes the energy of the X-rays for every one or more views. Further, the DAS 18 generates detection data by sequentially acquiring the signals of the X-rays in correspondence with each family of detecting elements in which the number of rows has been adjusted at step S510. Further, the processing circuitry 44 performs the pre-processing process on the detection data output from the DAS 18 (step S512). Further, on the basis of the data (the raw data) resulting from the pre-processing process, the processing circuitry 44 generates CT image data (step S513).

In this situation, the processing circuitry 44 judges whether or not a CT image is to be displayed (step S514). When a CT image is to be displayed because, for example, a display instruction is received from the operator (step S514: Yes), the processing circuitry 44 generates a display-purpose CT image on the basis of the CT image data and causes the display 42 to display the generated CT image (step S515). On the contrary, when a CT image is not to be displayed (step S514: No), or after step S515 is performed, the processing circuitry 44 judges whether or not the imaging process is to be ended (step S516). When the imaging process is not to be ended because, for example, there is an additional imaging process to be performed (step S516: No), the processing circuitry 44 returns to step S502. On the contrary, when it is determined that the imaging process is to be ended (step S516: Yes), the processing circuitry 44 ends the process.

Alternatively, when the imaging process is not to be ended (step S516: No), the processing circuitry 44 may return to step S501. In other words, the processing circuitry 44 may obtain a predetermined imaging time for each imaging process. Further, in that situation, step S501 may be performed at any arbitrary time before step S506.

As explained above, the X-ray CT apparatus 1 according to the eighth embodiment is configured to adjust, on the basis of the imaging range, the number of rows in the family of detecting elements from which the DAS 18 acquires the signals, so that the imaging process is to be completed within the predetermined imaging time. More specifically, the setting function 446 is configured to set the imaging conditions. Further, the adjusting function 445 is configured to identify one or more selectable numbers of rows on the basis of the imaging conditions set by the setting function 446, to calculate the imaging times corresponding to the numbers of rows on the basis of the identified numbers of rows and the imaging range, to identify the number of rows that makes the imaging time corresponding to the number of rows shorter than the predetermined imaging time as the number-of-rows candidate, and to adjust the number of rows in the family of detecting elements from which the DAS 18 acquires the signals, on the basis of the number-of-rows candidate. Consequently, by setting the imaging conditions at first, the X-ray CT apparatus 1 according to the eighth embodiment is able to enhance the degree of freedom of the imaging conditions and to also exercise control so that the switching of the tube voltage value is completed within the allowed period and is further able to complete the imaging process within the predetermined imaging time.

Further, as explained above, when it is not possible to identify the number of rows (the number-of-rows candidate) that makes it possible to complete the imaging process on the imaging range within the predetermined imaging time, the adjusting function 445 is configured to adjust the pitch for the imaging process. In other words, the adjusting function 445 is configured to adjust the number of rows in the family of detecting elements from which the DAS 18 acquires the signals and the pitch for the imaging process, so that the imaging process is to be completed within the predetermined imaging time. Consequently, even when the imaging range is long or when imaging conditions that tend to make the imaging time longer are set, or the like, the X-ray CT apparatus 1 according to the eighth embodiment is able to complete the imaging process within the predetermined imaging time, by adjusting the pitch for the imaging process.

The fifth to the eighth embodiments have thus been explained; however, it is possible to carry out the present disclosure in various different modes other than those described above in the fifth to the eighth embodiments.

In the fifth to the eighth embodiments above, the example is explained in which the processing circuitry 44 in the X-ray CT apparatus 1 includes the adjusting function 445. However, possible embodiments are not limited to this example. For instance, an external apparatus connected to the X-ray CT apparatus 1 via a network may have a function corresponding to the adjusting function 445.

Figure 31:
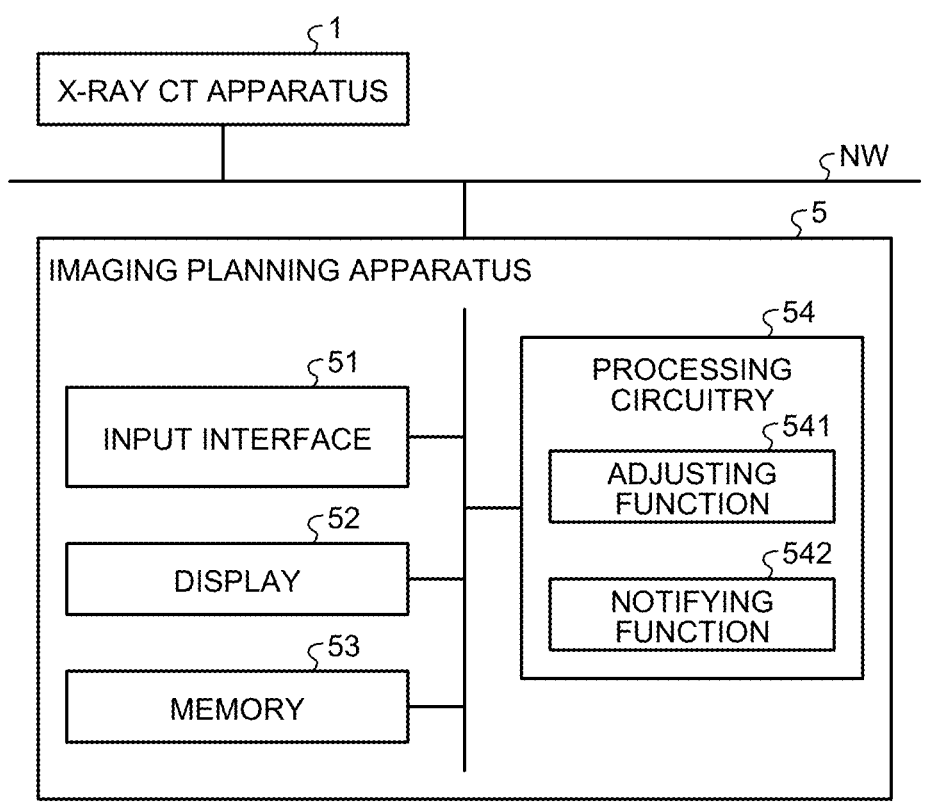
FIG. 31 is a block diagram illustrating an exemplary configuration of an imaging planning apparatus according to a ninth embodiment.

For example, as illustrated in FIG. 31, the X-ray CT apparatus 1 may be connected to an imaging planning apparatus 5 via a network NW. For example, the imaging planning apparatus 5 is realized by using a computer device such as a workstation. FIG. 31 is a block diagram illustrating an exemplary configuration of the imaging planning apparatus 5 according to a ninth embodiment.

As long as the connection via the network NW is possible, the X-ray CT apparatus 1 and the imaging planning apparatus 5 may be installed in any arbitrary locations. For example, the imaging planning apparatus 5 may be installed in a hospital different from the hospital in which the X-ray CT apparatus 1 is installed. In other words, the network NW may be a local network enclosed in a hospital or may be a network routed through the Internet. Further, although FIG. 31 illustrates the single X-ray CT apparatus 1, the imaging planning apparatus 5 may be connected to two or more X-ray CT apparatuses 1.

As illustrated in FIG. 31, the imaging planning apparatus 5 includes an input interface 51, a display 52, a memory 53, and processing circuitry 54.

The input interface 51 is configured to receive various types of input operations from an operator, to convert the received input operations into electric signals, and to output the electric signals to the processing circuitry 54. For example, the input interface 51 is realized by using a mouse, a keyboard, a trackball, a switch, a button, a joystick, a touchpad on which an input operation can be performed by touching the operation surface thereof, a touch screen in which a display screen and a touchpad are integrally formed, a contactless input circuit using an optical sensor, an audio input circuit, and/or the like. Alternatively, the input interface 51 may be configured by using a tablet terminal or the like capable of wirelessly communicating with the main body of the imaging planning apparatus 5. Further, the input interface 51 does not necessarily have to include one or more physical operation component parts such as a mouse and a keyboard. For instance, possible examples of the input interface 51 include an electric signal processing circuit configured to receive an electric signal corresponding to an input operation from an external input device provided separately from the imaging planning apparatus 5 and to output the electric signal to the processing circuitry 54.

The display 52 is configured to display various types of information. For example, the display 52 is configured to display a GUI used for receiving various types of instructions, various types of settings, and the like from the operator via the input interface 51. For example, the display 52 may be a liquid crystal display monitor or a CRT display monitor. The display 52 may be of a desktop type or may be configured with a tablet terminal or the like capable of wirelessly communicating with the main body of the imaging planning apparatus 5.

The memory 53 is realized by using, for example, a semiconductor memory element such as a RAM or a flash memory, or a hard disk, an optical disk, or the like. For example, the memory 53 is configured to store therein a program that enables circuits included in the imaging planning apparatus 5 to realize the functions thereof. Alternatively, the memory 53 may be realized with a group of servers (a cloud) connected to the imaging planning apparatus 5 via the network NW.

The processing circuitry 54 is configured to control operations of the entirety of the imaging planning apparatus 5 by executing an adjusting function 541 and a notifying function 542. In this situation, the adjusting function 541 is an example of an adjusting unit. The notifying function 542 is an example of a notifying unit.

In the imaging planning apparatus 5 illustrated in FIG. 31, the processing functions are stored in the memory 53 in the form of computer-executable programs. The processing circuitry 54 is a processor configured to realize the functions corresponding to the programs, by reading and executing the programs from the memory 53. In other words, the processing circuitry 54 that has read the programs has the functions corresponding to the read programs.

Although FIG. 31 illustrates the example in which the processing functions, namely the adjusting function 541 and the notifying function 542, are realized by the single processing circuit (i.e., the processing circuitry 54), possible embodiments are not limited to this example. For instance, the processing circuitry 54 may be structured by combining together a plurality of independent processors so that the processing functions are realized as a result of the processors executing the programs. Further, the processing functions included in the processing circuitry 54 may be realized as being distributed among, or integrated together into, one or more processing circuits, as appropriate.

For example, the processing circuitry 54 is configured to control the allowed period for switching the tube voltage value to be supplied to the X-ray tube 11, by adjusting one or both of the number of rows and the number of channels in the family of detecting elements from which the DAS 18 included in the X-ray CT apparatus 1 acquires the signals, by reading and executing the program corresponding to the adjusting function 541 from the memory 53. Further, the processing circuitry 54 is configured to notify the X-ray CT apparatus 1 of an adjustment result obtained by the adjusting function 541, by reading and executing the program corresponding to the notifying function 542 from the memory 53. In the example illustrated in FIG. 31, the X-ray CT apparatus 1 does not necessarily have to include the adjusting function 445.

For example, the adjusting function 541 is configured to control the allowed period for the switching of the tube voltage value to be supplied to the X-ray tube 11, by adjusting one or both of the number of rows and the number of channels in the family of detecting elements from which the DAS 18 acquires the signals. The notifying function 542 is configured to notify the X-ray CT apparatus 1 of the adjustment result obtained by the adjusting function 541. For example, the notifying function 542 is configured to notify the X-ray CT apparatus 1 of the allowed period resulting from the control exercised by the adjusting function 541. In that situation, the setting function 446 of the X-ray CT apparatus 1 sets imaging conditions on the basis of the allowed period indicated in the notification. Alternatively, the adjusting function 541 may be configured to set imaging conditions on the basis of the allowed period resulting from the control. In that situation, the notifying function 542 is configured to notify the X-ray CT apparatus 1 of the imaging conditions set by the adjusting function 541.

In other words, as the adjustment result obtained by the adjusting function 541, the notifying function 542 notifies the X-ray CT apparatus 1 of either the allowed period or the imaging conditions resulting from the control exercised by the adjusting function 541. When the adjusting function 541 is configured to set the imaging conditions, the X-ray CT apparatus 1 does not necessarily have to include the setting function 446.

In another example, the adjusting function 541 may be configured to obtain, via the network NW, the imaging conditions set by the setting function 446 included in the X-ray CT apparatus 1. Alternatively, the adjusting function 541 may be configured to set the imaging conditions. Subsequently, the adjusting function 541 controls the allowed period for the switching of the tube voltage value to be supplied to the X-ray tube 11, by adjusting one or both of the number of rows and the number of channels in the family of detecting elements from which the DAS 18 acquires the signals, on the basis of the imaging conditions. After that, the notifying function 542 notifies the X-ray CT apparatus 1 of the adjustment result obtained by the adjusting function 541. In this situation, when the imaging conditions were set by the setting function 446, the notifying function 542 notifies the X-ray CT apparatus 1 of the allowed period resulting from the control exercised by the adjusting function 541. In contrast, when the imaging conditions were set by the adjusting function 541, the notifying function 542 notifies the X-ray CT apparatus 1 of the allowed period resulting from the control exercised by the adjusting function 541 and the set imaging conditions.

In other words, as the adjustment result obtained by the adjusting function 541, the notifying function 542 is configured to notify the X-ray CT apparatus 1 of either the allowed period resulting from the control exercised by the adjusting function 541 or the allowed period and the imaging conditions resulting from the control exercised by the adjusting function 541. When the adjusting function 541 is configured to set the imaging conditions, the X-ray CT apparatus 1 does not necessarily have to include the setting function 446.

Further, in the fifth to the eighth embodiments above, the example is explained in which the dual-energy acquisition is performed; however, another example is also acceptable in which a multi-energy acquisition is performed by using X-rays having three or more mutually-different types of energy. For example, the system controlling function 441 may be configured to change the energy of the X-rays for every one or more views, by switching the tube voltage value to be supplied to the X-ray tube 11 among the first tube voltage value V1, the second tube voltage value V2, and a third tube voltage value V3 smaller than the second tube voltage value V2. Further, either the adjusting function 445 or the adjusting function 541 is configured to control the allowed period for switching the tube voltage value between the first tube voltage value V1 and the second tube voltage value V2 and the allowed period for switching the tube voltage value between the second tube voltage value V2 and the third tube voltage value V3, by adjusting one or both of the number of rows and the number of channels in the family of detecting elements from which the DAS 18 acquires the signals.

Further, in the fifth to the eighth embodiments above, the X-ray CT apparatus of a single-tube type was explained as an example of the X-ray CT apparatus 1; however, possible embodiments are not limited to this example. The X-ray CT apparatus 1 may be an X-ray CT apparatus of a so-called multi-tube type in which a plurality of pairs each made up of an X-ray tube and an X-ray detector are installed on a rotating ring.

For example, the X-ray CT apparatus 1 may include a pair made up of a first X-ray tube and a first X-ray detector and another pair made up of a second X-ray tube and a second X-ray detector. Further, the X-ray CT apparatus 1 includes: a first DAS configured to sequentially acquire signals of X-rays in correspondence with each family of detecting elements included in the first X-ray detector; and a second DAS configured to sequentially acquire signals of X-rays in correspondence with each family of detecting elements included in the second X-ray detector.

In this situation, for example, the system controlling function 441 is configured to change the energy of the X-rays for every one or more views, by switching the tube voltage value to be supplied to the first X-ray tube between a first tube voltage value V11 and a second tube voltage value V12. Further, either the adjusting function 445 or the adjusting function 541 is configured to control the allowed period for switching the tube voltage value between the first tube voltage value V11 and the second tube voltage value V12, by adjusting one or both of the number of rows and the number of channels in the family of detecting elements from which the first DAS acquires the signals. Further, the system controlling function 441 is configured to change the energy of the X-rays for every one or more views, by switching the tube voltage value to be supplied to the second X-ray tube between a first tube voltage value V21 and a second tube voltage value V22. Further, either the adjusting function 445 or the adjusting function 541 is configured to control the allowed period for switching the tube voltage value between the first tube voltage value V21 and the second tube voltage value V22 by adjusting one or both of the number of rows and the number of channels in the family of detecting elements from which the second DAS acquires the signals. With these arrangements, the system controlling function 441 is able to perform the multi-energy acquisition by using the fast switching, while using the X-rays having the four types of mutually-different energy.

The term "processor" used in the above explanations denotes, for example, a CPU, a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 41 or the memory 53.

With reference to FIGS. 1 and 12, the example was explained in which the single memory (i.e., the memory 41) stores therein the programs corresponding to the processing functions. Further, with reference to FIG. 31, the example was explained in which the single memory (i.e., the memory 53) stores therein the programs corresponding to the processing functions; however, possible embodiments are not limited to these examples. For instance, another configuration is also acceptable in which two or more memories 41 are provided in a distributed manner, so that the processing circuitry 44 reads a corresponding program from each of the individual memories 41. Further, for example, yet another configuration is also acceptable in which two or more memories 53 are provided in a distributed manner, so that the processing circuitry 54 reads a corresponding program from each of the individual memories 53. Further, instead of saving the programs in either the memory 41 or the memory 53, it is also acceptable to directly incorporate the programs into the circuit of a processor. In that situation, the processor realizes the functions by reading and executing the programs incorporated in the circuit thereof.

Further, the processing circuitry 44 and the processing circuitry 54 may be configured to realize the functions by using a processor of an external apparatus connected via a network. For example, the processing circuitry 44 may realize the functions illustrated in FIGS. 1 and 12 by reading and executing the programs corresponding to the functions from the memory 41 and using an external workstation or cloud connected to the X-ray CT apparatus 1 via the network NW as a computation resource. Further, for example, the processing circuitry 54 may realize the functions illustrated in FIG. 31 by reading and executing the programs corresponding to the functions from the memory 53 and using an external workstation or cloud connected to the imaging planning apparatus 5 via the network NW as a computation resource.

The constituent elements of the apparatuses and the devices described in the embodiments above are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

It is possible to realize the controlling method described in any of the embodiments above by causing a computer such as a personal computer or a workstation to execute a control program prepared in advance. It is possible to distribute the control program via a network such as the Internet. Further, it is also possible to record the control program onto a computer-readable recording medium such as a hard disk, a flexible disk (FD), a Compact Disk Read-Only Memory (CD-ROM), a Magneto Optical (MO) disk, a Digital Versatile Disk (DVD), or the like, so as to be executed as being read from the recording medium by a computer.

According to at least one aspect of the embodiments described above, it is possible to perform the dual-energy acquisition or the multi-energy acquisition by using the fast switching method, while employing the one or more DASs that use the sequential acquisition method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
an X-ray generator configured to generate X-rays;
an X-ray detector configured to detect X-rays that have passed through a patient and including first to n-th groups of detecting elements configured to store therein electric charges generated from the detection (where n is an integer of 2 or larger);
a Data Acquisition System (DAS) configured to acquire detection data for each view by repeatedly performing a process of sequentially reading the electric charges stored in the first to the n-th groups of detecting elements in units of groups starting with the first group of detecting elements; and
processing circuitry configured to:
periodically change energy of X-rays radiated onto the patient, a period of the changing the energy of the X-rays corresponding to a time it takes for the DAS to complete reading the electric charges stored in the first to the n-th groups of detecting elements, and
control the X-ray generator so that, while the detection data related to one view or a plurality of consecutive views is acquired, an average energy level of the X-rays radiated onto the patient is substantially equal among the groups of detecting elements.

2. The X-ray CT apparatus according to claim 1, wherein the processing circuitry periodically changes the energy of the X-rays radiated onto the patient, and
the processing circuitry controls the X-ray generator so that the energy of the X-rays radiated onto the patient is constant in a time period defined while using, as a reference, timing with which the storing of the electric charges is started by the n-th group of detecting elements during a detection data acquisition period for a first view and timing with which the storing of the electric charges is ended by the first group of detecting elements during the detection data acquisition period for the first view.

3. The X-ray CT apparatus according to claim 1, wherein the processing circuitry periodically changes the energy of the X-rays radiated onto the patient, and
the processing circuitry controls the X-ray generator so that the energy of the X-rays radiated onto the patient is constant in a time period defined while using, as a reference, timing with which the storing of the electric charges is started by the n-th group of detecting elements during a detection data acquisition period for a first view and timing with which the storing of the electric charges is ended by the first group of detecting elements during a detection data acquisition period for a second view.

4. The X-ray CT apparatus according to claim 1, wherein the processing circuitry periodically changes the energy of the X-rays radiated onto the patient, and
the processing circuitry controls the X-ray generator so that the energy of the X-rays radiated onto the patient is constant in a time period defined while using, as a reference, timing with which the storing of the electric charges is started by the first group of detecting elements during a detection data acquisition period for a first view and timing with which the storing of the electric charges is ended by the n-th group of detecting elements during either the detection data acquisition period for the first view or a detection data acquisition period for a second view.

5. The X-ray CT apparatus according to claim 1, wherein for each of the views, the processing circuitry stops the radiation of the X-rays onto the X-ray detector at least while the DAS is acquiring the signals.

6. The X-ray CT apparatus according to claim 5, wherein for each of the views, the processing circuitry causes the X-rays to be generated in a pulse form while the DAS is not acquiring the signals.

7. The X-ray CT apparatus according to claim 5, wherein, when stopping the radiation of the X-rays onto the X-ray detector, the processing circuitry further obtains a length of time during which a residual component from the X-rays becoming incident is detected by the plurality of detecting element and stops the radiation of the X-rays onto the X-ray detector during a time period from a point in time earlier, by the obtained length of time or longer, than a time when the DAS starts acquiring the signals to the time when the DAS starts acquiring the signals.

8. The X-ray CT apparatus according to claim 1, wherein for each of the views, the processing circuitry stops the radiation of the X-rays onto the X-ray detector or maintains the energy of the X-rays to be constant at least while the DAS is acquiring the signals.

9. The X-ray CT apparatus according to claim 1, wherein the processing circuitry changes the energy of the X-rays in a time period after the DAS finishes acquiring the signals for a first view and before the DAS starts acquiring the signals for a second view that is later than the first view.

10. The X-ray CT apparatus according to claim 9, wherein the processing circuitry maintains the energy of the X-rays to be constant at least while the DAS is acquiring the signals for two or more views from the second view to a third view that is later than the second view.

11. The X-ray CT apparatus according to claim 1, wherein the processing circuitry changes the energy of the X-rays from a first energy level to a second energy level in a time period after the DAS finishes acquiring the signals for a first view and before the DAS starts acquiring the signals for a second view that is later than the first view, and subsequently, changes the energy of the X-rays from the second energy level to the first energy level.

12. The X-ray CT apparatus according to claim 1, wherein the processing circuitry changes the energy of the X-rays by controlling X-ray tube voltage supplied to the X-ray generator.

13. The X-ray CT apparatus according to claim 1, wherein
the X-ray generator generates the X-rays having the energy corresponding to X-ray tube voltage being applied thereto, and
the processing circuitry periodically switches the X-ray tube voltage and switches the X-ray tube voltage within a time period corresponding to the n.

14. The X-ray CT apparatus according to claim 13, wherein the processing circuitry further controls an allowed time period for switching the X-ray tube voltage by adjusting one or both of a quantity of rows and a quantity of channels in a family of detecting elements from which the DAS acquires the signals.

15. The X-ray CT apparatus according to claim 14, wherein the processing circuitry further sets an imaging condition on a basis of the allowed time period.

16. The X-ray CT apparatus according to claim 15, wherein the processing circuitry sets the imaging condition by changing a pre-set condition set in advance.

17. The X-ray CT apparatus according to claim 15, wherein the processing circuitry newly sets the imaging condition.

18. The X-ray CT apparatus according to claim 15, wherein the processing circuitry sets an X-ray tube current value of the X-ray generator as the imaging condition.

19. The X-ray CT apparatus according to claim 18, wherein the processing circuitry sets a lower limit for selectable X-ray tube current values on a basis of the allowed time period and sets the X-ray tube current value of the X-ray generator so as to exceed the lower limit.

20. The X-ray CT apparatus according to claim 15, wherein the processing circuitry sets the X-ray tube voltage to be supplied to the X-ray generator as the imaging condition.

21. The X-ray CT apparatus according to claim 20, wherein
the processing circuitry sets first X-ray tube voltage and second X-ray tube voltage as the X-ray tube voltage to be supplied to the X-ray generator, and
the processing circuitry changes the energy of the X-rays for every one or more views, by switching the X-ray tube voltage to be supplied to the X-ray generator between the first X-ray tube voltage and the second X-ray tube voltage.

22. The X-ray CT apparatus according to claim 14, wherein
the processing circuitry further sets an imaging condition, and
the processing circuitry controls the allowed time period by adjusting the one or both of the quantity of rows and the quantity of channels on a basis of the set imaging condition.

23. The X-ray CT apparatus according to claim 14, wherein, on a basis of an imaging range, the processing circuitry adjusts the one or both of the quantity of rows and the quantity of channels so that an imaging process is to be completed within a predetermined imaging time.

24. The X-ray CT apparatus according to claim 23, wherein the processing circuitry:
calculates an imaging time corresponding to a quantity of rows on the basis of the imaging range,
identifies a quantity of rows that makes the calculated imaging time shorter than the predetermined imaging time as a quantity-of-rows candidate, and
adjusts the quantity of rows in the family of detecting elements from which the DAS acquires the signals on the basis of the quantity-of-rows candidate.

25. The X-ray CT apparatus according to claim 23, wherein the processing circuitry:
sets an imaging condition,
identifies a selectable quantity of rows on a basis of the set imaging condition,
calculates an imaging time corresponding to the quantity of rows on a basis of the identified quantity of rows and the imaging range,
identifies a quantity of rows that makes the calculated imaging time shorter than the predetermined imaging time as a quantity-of-rows candidate, and
adjusts the quantity of rows in the family of detecting elements from which the DAS acquires the signals on a basis of the quantity-of-rows candidate.

26. The X-ray CT apparatus according to claim 23, wherein the processing circuitry adjusts the one or both of the quantity of rows and the quantity of channels and a pitch for the imaging process so that the imaging process is to be completed within the predetermined imaging time.

27. The X-ray CT apparatus according to claim 23, wherein the predetermined imaging time is a time period during which the patient is able to hold his/her breath.

28. The X-ray CT apparatus according to claim 14, wherein the processing circuitry adjusts the one or both of the quantity of rows and the quantity of channels by adjusting a bundling condition used when the DAS acquires the signals.

29. An imaging planning apparatus comprising:
first processing circuitry configured to:
control an allowed time period for switching an X-ray tube voltage by adjusting one or both of a quantity of rows and a quantity of channels in a family of detecting elements from which a Data Acquisition System (DAS) acquires signals with regard to an X-ray CT apparatus including an X-ray generator configured to generate X-rays having energy corresponding to the X-ray tube voltage applied thereto, an X-ray detector configured to detect X-rays that have passed through a patient and including first to n-th groups of detecting elements configured to store therein electric charges generated from the detection (where n is an integer of 2 or larger), the DAS configured to acquire detection data for each view by repeatedly performing a process of sequentially reading the electric charges stored in the first to the n-th groups of detecting elements in units of groups starting with the first group of detecting elements, and second processing circuitry configured to periodically change energy of X-rays radiated onto the patient and control the X-ray generator so that, while the detection data related to one view or a plurality of consecutive views is acquired, an average energy level of the X-rays radiated onto the patient is substantially equal among the groups of detecting elements; and
notify the X-ray CT apparatus of an adjustment result regarding the one or both of the quantity of rows and the quantity of channels.

30. An X-ray CT apparatus comprising:
an X-ray generator configured to generate X-rays having an energy corresponding to X-ray tube voltage being applied thereto;
an X-ray detector configured to detect X-rays that have passed through a patient and including first to n-th groups of detecting elements configured to store therein electric charges generated from the detection (where n is an integer of 2 or larger);
a Data Acquisition System (DAS) configured to acquire detection data for each view by repeatedly performing a process of sequentially reading the electric charges stored in the first to the n-th groups of detecting elements in units of groups starting with the first group of detecting elements; and
processing circuitry configured to periodically switch the X-ray tube voltage and switch the X-ray tube voltage within a time period corresponding to the n.

\* \* \* \* \*